United States Patent [19]

Hartman et al.

[11] Patent Number: 5,162,217

[45] Date of Patent: * Nov. 10, 1992

[54] PLASMIDS FOR EXPRESSION OF HUMAN SUPEROXIDE DISMUTASE (SOD) ANALOGS CONTAINING LAMBDA PL PROMOTER WITH ENGINEERED RESTRICTION SITE FOR SUBSTITUTING RIBOSOMAL BINDING SITES AND METHODS OF USE THEREOF

[75] Inventors: Jacob R. Hartman, Holon; Amos B. Oppenheim, Jerusalem; Marian Gorecki; Haim Aviv, both of Rehovot; Rachel Oren, Rehovot, all of Israel

[73] Assignee: Bio-Technology General Corp., New York, N.Y.

[*] Notice: The portion of the term of this patent subsequent to Sep. 1, 2009 has been disclaimed.

[21] Appl. No.: 449,125

[22] Filed: Dec. 8, 1989

Related U.S. Application Data

[63] Continuation of Ser. No. 202,238, Jun. 3, 1988, abandoned, which is a continuation of Ser. No. 897,056, Aug. 14, 1986, abandoned, which is a continuation-in-part of Ser. No. 767,143, Aug. 19, 1985, abandoned, which is a continuation-in-part of Ser. No. 644,245, Aug. 27, 1984, abandoned.

[30] Foreign Application Priority Data

Aug. 15, 1985 [CA] Canada ........................... 488832

[51] Int. Cl.$^5$ ..................... C12N 9/02; C12N 15/70
[52] U.S. Cl. ........................ 435/189; 435/320.1; 435/252.33
[58] Field of Search ............... 435/320.1, 252.33, 189; 536/27

[56] References Cited

U.S. PATENT DOCUMENTS 4,512,922  4/1985  Jones et al. ............... 530/408
4,578,355  3/1986  Rosenberg ............... 435/317
4,637,980  1/1987  Auerbach et al. ............ 435/69.1

FOREIGN PATENT DOCUMENTS 0041767  12/1981  European Pat. Off.
0049619  4/1982   European Pat. Off.
0131843  1/1985   European Pat. Off.
0138111  4/1985   European Pat. Off.

OTHER PUBLICATIONS

Maniatis et al. in *Molecular Cloning, a Laboratory Manual*, Cold Spring Harbor, 1982, pp. 411–413 and 418, 419.

(List continued on next page.)

Primary Examiner—Richard A. Schwartz
Assistant Examiner—S. L. Nolan
Attorney, Agent, or Firm—John P. White

[57] ABSTRACT

An improved plasmid for the production of superoxide dismutase which upon introduction into a host containing the thermolabile repressor $C_I$ renders the host capable of effecting expression of a gene encoding superoxide dismutase. The plasmid which includes in 5' to 3' order the following: the promoter and operator $P_L O_L$ from lambda bacteriophage; the N utilization site; a first restriction enzyme site permitting replacement of the ribosomal binding site which follows thereafter; a ribosomal binding site; an ATG initiation codon; a second restriction enzyme site; a gene encoding superoxide dismutase; an origin of replication and a gene associated with a selectable or identifiable phenotypic trait manifested when the plasmid is present in the host. The distance between the 3' end of $P_L O_L$ and the 5' end of the N utilization site is less than about 80 base pairs. The distance between the 3' end of the N utilization site and the 5' end of the ribosomal binding site is less than about 300 base pairs.

Host vector systems have been constructed from these plasmids and used to produce human superoxide dismutase and analogs thereof. Such SOD or analogs may be used to catalyze the reduction of superoxide radicals, reduce reperfusion injury, prolong the survival time of isolated organs and reduce spinal cord injury.

20 Claims, 31 Drawing Sheets

OTHER PUBLICATIONS

Lieman-Hurwitz et al. *Proc. Natl. Acad. Sci. (USA)* 79:2808–2811, 1982 (May).
Bernard, H. U., et al., Gene 5:59–76 (1979).
Cheysen, D., et al., Gene 17:55–63 (1982).
Hedgpeth, J., et al., Molec. Gen. Genet. 163:197–203 (1978).
Remaut, E., et al., Gene 15:81–93 (1981).
Derynck, R., et al., Nature 287:193–197 (1980).
Oppenheim, A. B., et al., J. Mol. Biol. 158:327–346 (1982).
Courtney, M., et al., Proc. Natl. Acad. Sci. U.S.A. 81:669–673 (1984).
Lautenberger, J. A., et al., Gene 23:75–84 (1983).
Lautenberger, J. A., et al., Science 221:858–860 (1983).
Shatzman, A. R., et al., 14 Miami Winter Symposium, Abstract p. 98 (1982).
McCord, J. M., et al., Can. J. Physiol. Pharmacol. 60:1346–1352 (1982).
Alvarez, J. G., et al., Biol. Reprod. 28:1129–1136 (1983).
Tolmasoff, J. M., et al., Proc. Natl. Acad. Sci. U.S.A. 77:2777–2781 (1980).
Rosenberg, J., et al. in "Methods in Enzymology", vol. 101 (Colowick and Kaplan, eds.), pp. 123–138 (1983).
Zabeau, M., et al., EMBO Journal 1(10):1217–1224 (1982).
Backman, K., et al., Cell 13:65–71 (1978).
Guarente, L., et al., Science 209:1428–1430 (1980).
Guarente, L., et al., Cell 20:543–553 (1980).
Derom, C., et al., Gene 17:45–54 (1982).
Shimatake, H., et al., Nature 292:128–132 (1981).

Figure 11
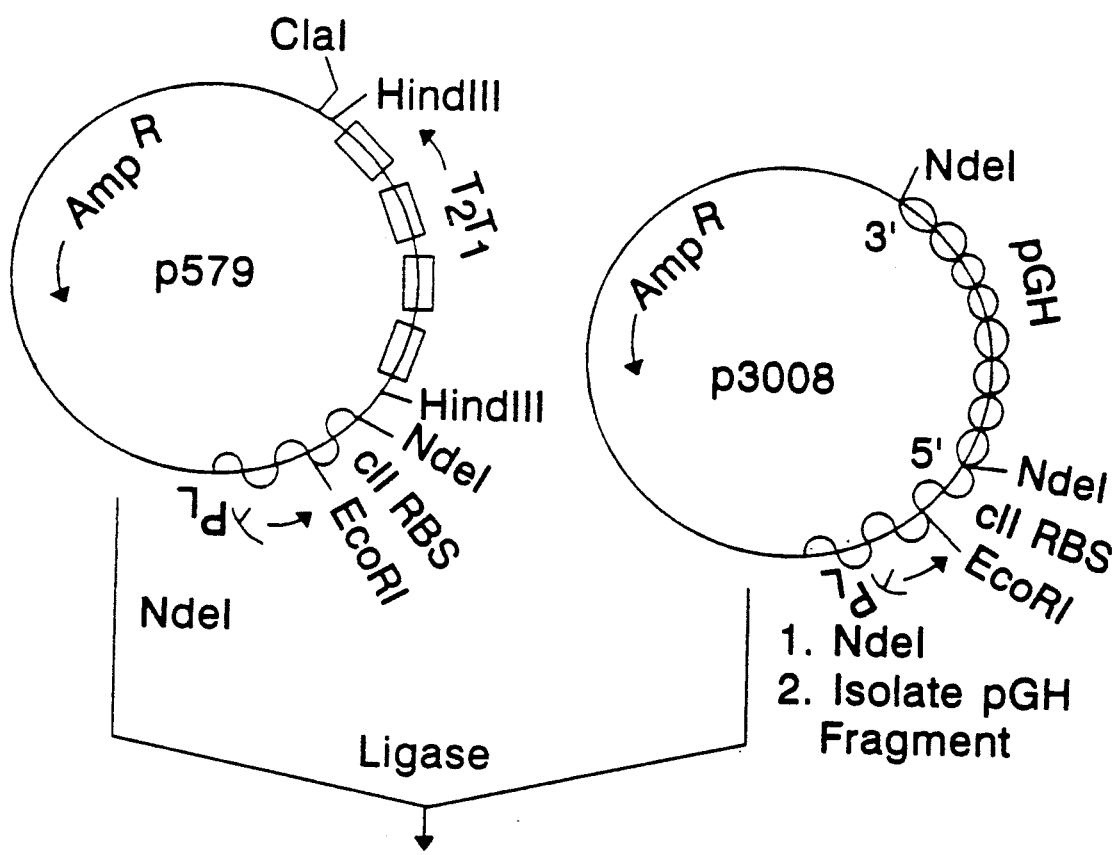
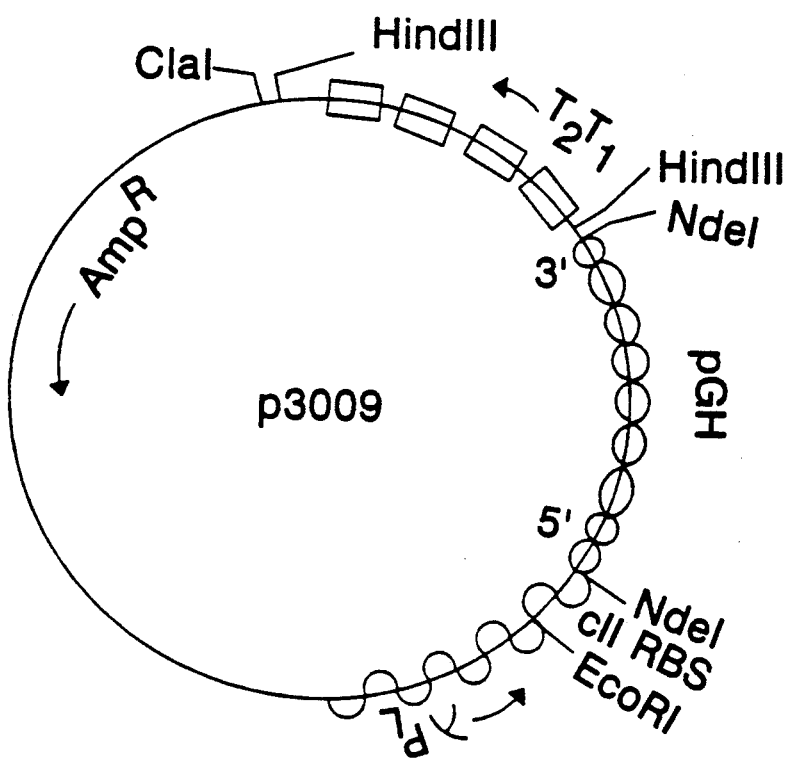

Figure 19
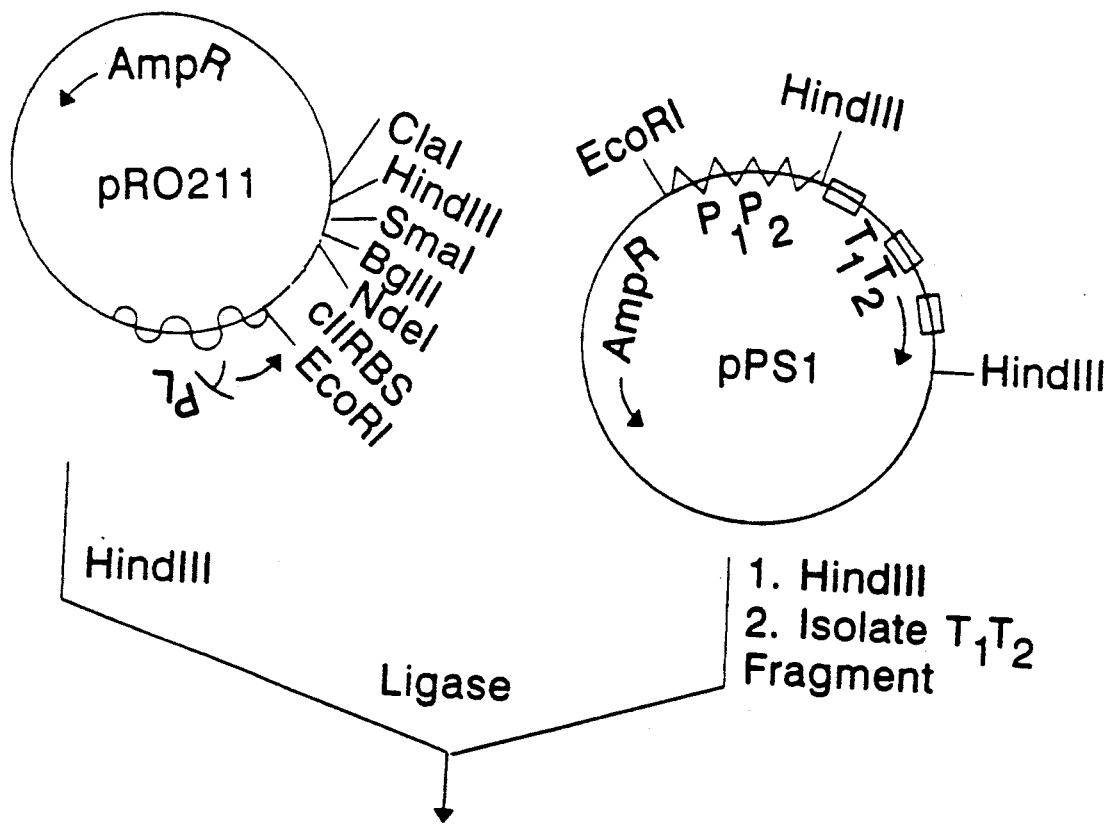
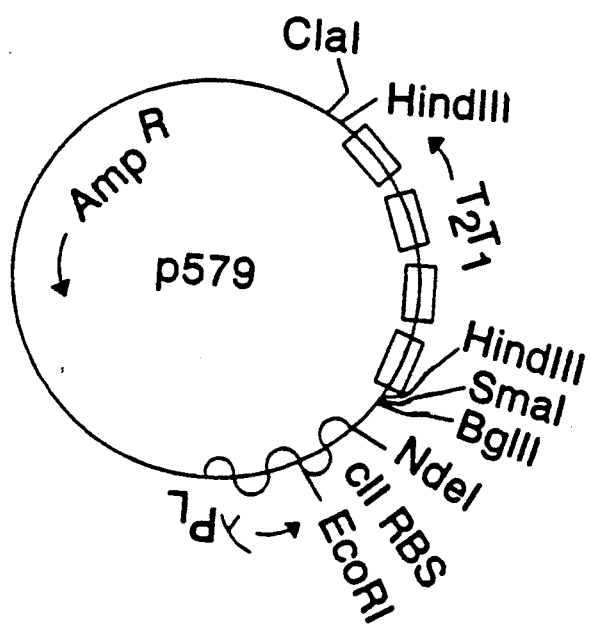

Figure 21
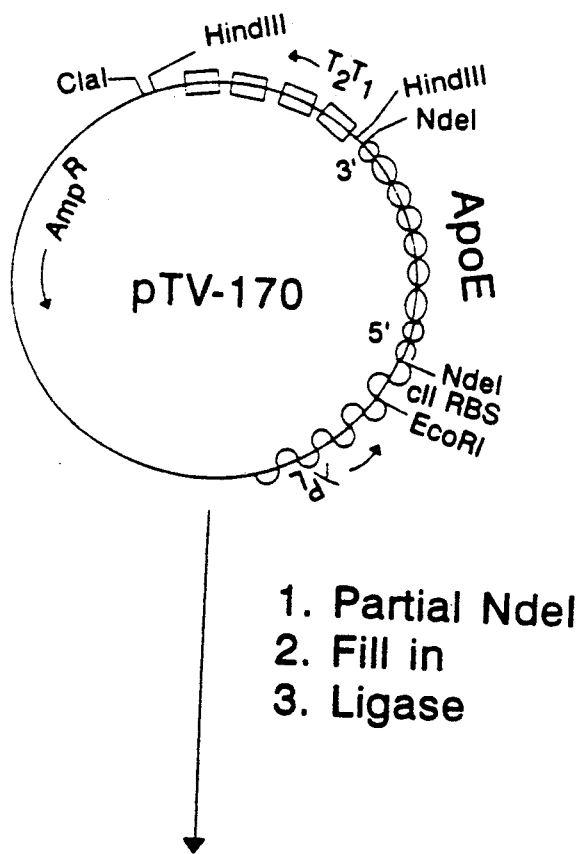
1. Partial NdeI
2. Fill in
3. Ligase
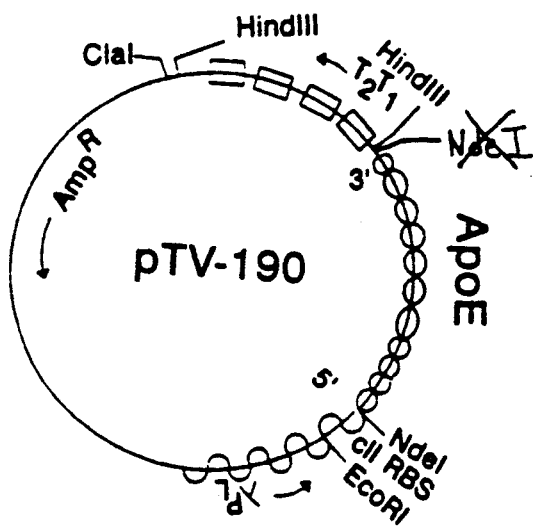

Figure 26
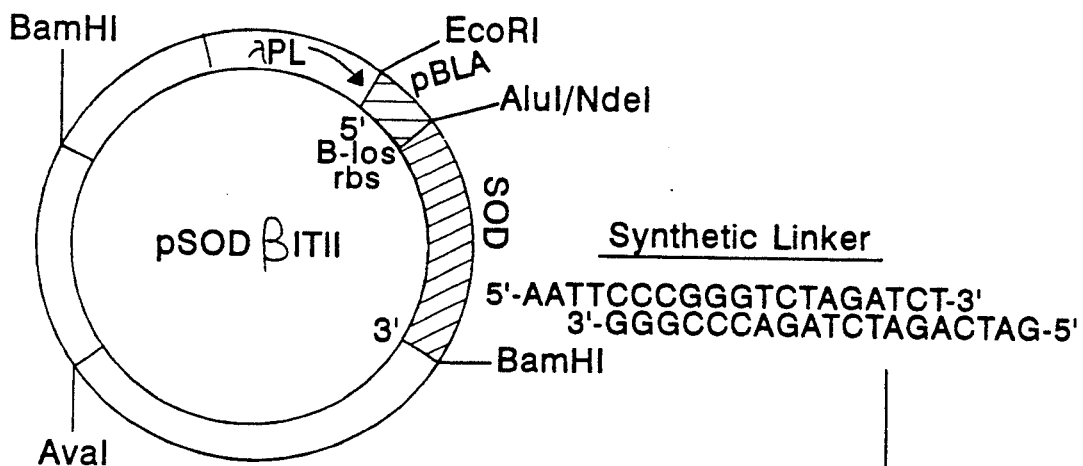
1. EcoRI
2. Partial BamHI
3. Isolate large EcoRI-BamHI Fragment
1. Kinase
2. Anneal
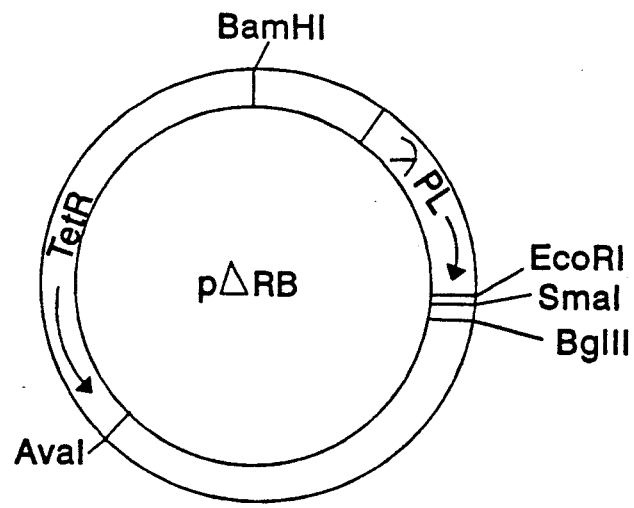

Figure 28
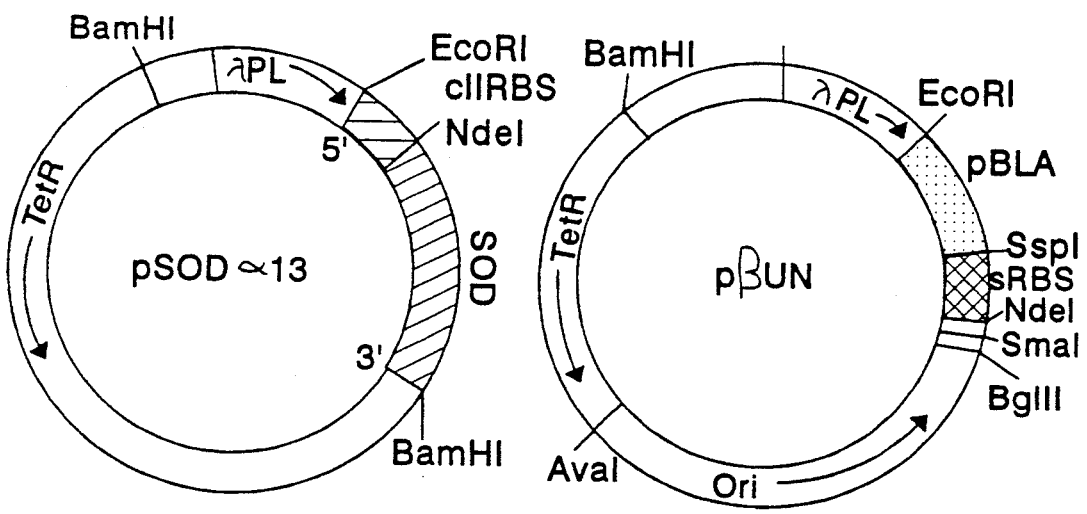
1. NdeI + BamHI
2. Isolate SOD NdeI-BamHI Fragment
1. NdeI + BglII
2. Isolate Large Fragment
T4 DNA Ligase
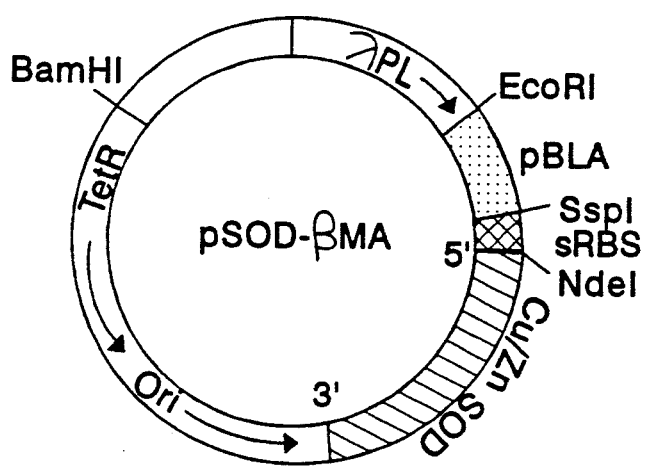

Figure 30
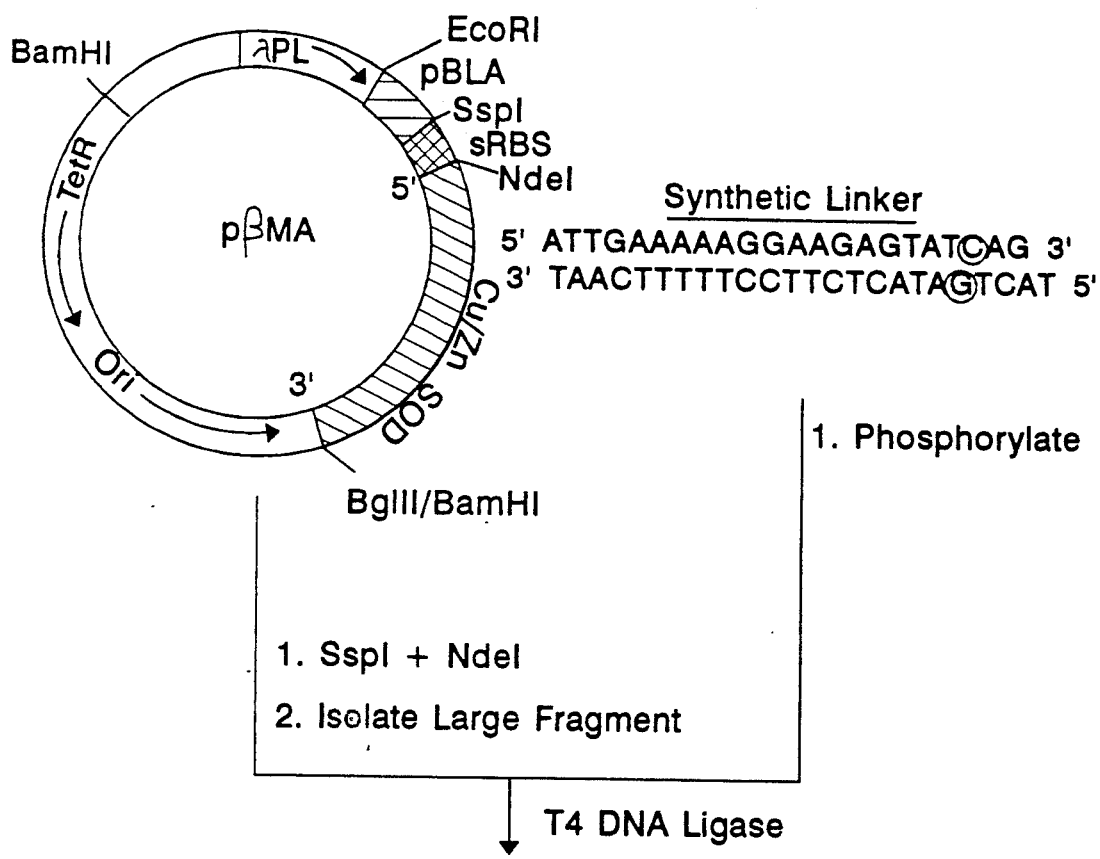
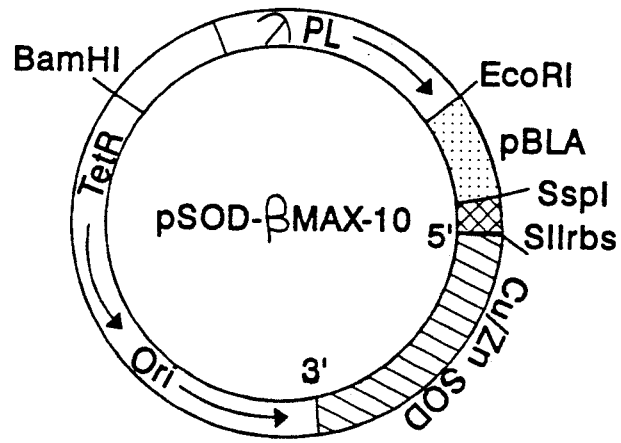

PLASMIDS FOR EXPRESSION OF HUMAN SUPEROXIDE DISMUTASE (SOD) ANALOGS CONTAINING LAMBDA PL PROMOTER WITH ENGINEERED RESTRICTION SITE FOR SUBSTITUTING RIBOSOMAL BINDING SITES AND METHODS OF USE THEREOF

This is a continuation of Ser. No. 202,238, filed Jun. 3, 1988, now abandoned, which is a continuation of application U.S. Ser. No. 897,056, filed August, 1986, now abandoned, which is a continuation-in-part of application U.S. Ser. No. 767,143, filed Aug. 19, 1985 which in turn is a continuation-in-part of U.S. Ser. No. 644,245, filed Aug. 27, 1984 both now abandoned.

BACKGROUND OF THE INVENTION

One aspect of genetic engineering involves the insertion of foreign DNA sequences derived from eucaryotic sources into *Escherichia coli* or other microorganisms. A further refinement of genetic engineering concerns inducing the resulting microorganism to produce polypeptides encoded by the foreign DNA. Production of polypeptides can be considered a two-step process, with each step including numerous substeps. The two steps are transcription and translation. To produce a polypeptide efficiently and in quantity both steps of the process must be efficient. Transcription is the production of mRNA from the gene (DNA). Translation is the production of polypeptide from the mRNA.

A critical substep of the transcription process is initiation, that is, the binding of RNA polymerase to a promoter-operator region. The sequence of deoxyribonucleotide bases which make up the promoter region may vary and thereby affect the relative efficiency of the promoter. The efficiency depends on the affinity of the RNA polymerase for the promoter.

The efficiency of translation is affected by the stability of the mMRA. Increased stability of the mRNA permits improved translation. Although the exact determinants of mRNA stability are not precisely known, it is known that mRNA secondary structure as determined by the sequence of its bases has a role in stability.

The initial substep of translation involves binding of the ribosome to a base sequence on the mRNA known as the Shine-Dalgarno sequence or the ribosomal binding site (RBS). The synthesis of polypeptides begins when the ribosome migrates along the mRNA to the AUG start codon for translation. Generally these codons are found approximately 10 bases "downstream" from the Shine-Dalgarno site. Factors which increase the efficiency of translation include those which enhance binding of the ribosomes to the Shine-Dalgarno site. It has been shown that the structure of the mRNA in the region of the Shine-Dalgarno sequence and the AUG codon and the distance between the Shine-Dalgarno sequence and the AUG codon each play a critical role in determining the efficiency of translation. Other factors which affect the efficiency of translation are premature termination and attenuation. Efficiency of translation can be improved by removing the attenuation sites.

A difficulty encountered in attmpts to produce high amounts of eucaryotic polypeptides in bacterial cells nvolves the inability of cells producing large amounts of mRNA to grow efficiencly. This difficulty can be eliminated by preventing trranscription by a process known as repression. In repression, genes are switched off due to the action of a protein inhibitor (repressor protein) which prevents transcription by binding to the operator region. After microorganisms have grown to desired cell densities, the repressed genes are activated by destruction of the repressor or by addition of molecules known as inducers which overcome the effect of the repressor.

Numerous reports may be found in the literature concerning the cloning of eucaryotic genes in plasmids containing the $P_L$ promoter from λ bacteriophage. (Bernard, H. V. et al., Gene (1979) 5, 59; Derom, C., et al., Gene (1982) 17, 45; Gheysen, D., et al., Gene (1982) 17, 55; Hedgpeth, J., et al., Mol. Gen. Genet. (1978) 163, 197; Remaut, E., et al., (1981) Gene 15, 81 and Derynck, R., et al., Nature (1980) 287, 193. In addition, European Patent Application No. 041,767, published Dec. 16, 1981, describes expression vectors containing the $P_L$ promoter from bacteriophage. However, none of these references describe the use of the $C_{II}$ ribosomal binding site.

The use of a vector containing the $P_L$ promoter from λ bacteriophage and the $C_{II}$ ribosomal binding site has been described. (Oppenheim, A. B., et al., J. Mol. Biol. (1982) 158, 327 and Shimatake, H. and Rosenberg, M., Nature (1981) 292, 128.) These publications describe the production of increased levels of $C_{II}$ protein but do not involve or describe the production of eucaryotic proteins.

Other vectors which contain the $P_L$ promoter and the $C_{II}$ ribosomal binding site have also been described (Courtney, M., et al., PNAS (1984) 81: 669–673; Lautenberger, J. A., et al., Gene (1983) 23: 75–84 and Lautenberger, J. A., et al., Science (1983) 221: 858–860). However, all of these vectors lead to the production of fused proteins which contain the amino terminal portion of the $C_{II}$ protein.

In 1982 Shatzman and Rosenberg presented a poster at the 14th Miami Winter Symposium (Shatzman, A. R. and Rosenberg, M., 14 Miami Winter Symposium, abstract p98 [1982]). This abstract provides a non-enabling disclosure of the use of a vector containing $P_L$ from λ bacteriophage, Nut and the $C_{II}$ ribosomal binding site to synthesize a "eucaryotic" polypeptide (SV40 small T antigen is actually not a eucaryotic polypeptide but a viral protein) in an amount greater than 5% of the cell protein in an unnamed bacterial host. The operator used is not defined. Neither an origin of replication nor a gene for a selectable phenotype is identified. This system with which the vector is used is described as including certain host lysogens into which the vector can be stably transformed.

Applicants are aware of the existence of a pending U.S. patent application in the name of M. Rosenberg filed under Ser. No. 457,352 by the National Institutes of Health, Dept. of Health and Human Services, U.S.A. Portions of this application have been obtained from the National Technical Information Service, U.S. Dept. of Commerce. However, the claims are not available and are maintained in confidence. The available portions of the application have been reviewed. This disclosure is not enabling. It indicates that the host is important (p8, line 17) but fails to identify any suitable host. It further depends upon the use of a λ mutant which is not specified (p4, line 20). it indicates that the host contains lysogens (p8, line 18) unlike the present invention in which the host is not lysogenic. It mentions cloning and expression of a eucaryotic gene, monkey metallothionein gene, (p7, line 18) but does not provide details. It specifies that neither the sequence nor the position of any nucleotide in the $C_{II}$ ribosomal binding region has been altered (p8, line 27).

Pending, co-assigned U.S. patent application Ser. No. 514,188, filed Jul. 15, 1983, describes novel vectors useful for the expression of polypeptides in bacteria.

These vectors include λ $P_LO_L$, the N utilization site for binding antiterminator N protein, a ribosomal binding site, an ATG codon, a restriction enzyme site for inserting a gene encoding a desired polypeptide, an origin of replication and a selectable marker. In these rectors the distance between the N utilization site and the ribosomal binding site is greater than about 300 base pairs. In addition, each of these vectors contains a specific ribosomal binding site which cannot be readily replaced. These vectors are not equally useful for expression of different polypeptides.

U.S. Ser. No. 514,188 also discloses a method of producing the polypeptide encoded in the vector by growing a host containing the vector, inducing polypeptide expression and recovering the polypeptide.

Superoxide dismutase (SOD) and analogs thereof are some of several polypeptides which may be produced using the vector and methods disclosed in Ser. No. 514,188.

The present invention relates to expression plasmids which unexpectedly provide enhanced expression of superoxide dismutase and analogs thereof. By employing different ribosomal binding sites in the plasmids of this invention it is possible to achieve enhanced expression levels of superoxide dismutase or analog thereof relative to the levels achieved with the previous vectors. In addition, using the same ribosomal binding sites as in the previous vectors, it is possible to achieve enhanced expression of superoxide dismutase or the analog.

The present invention also relates to a method for enhanced production of SOD and analogs thereof in bacteria, including prototrophic and lytic bacteria, utilizing these plasmids.

The present invention also provides for plasmids and methods which exclusively produce the non-acetylated analog of human CuZn superoxide dismutase having an amino acid sequence identical to that of natural human CuZn superoxide dismutase.

Superoxide dismutase is of considerable interest because of its pharmacological properties. Bovine-derived, naturally-occurring superoxide dismutase (orgotein) has been recognized to possess anti-inflammatory properties and is currently marketed in certain European countries, e.g., West Germany, for use in the treatment of inflammation. It is also sold in a number of countries including the United States as a veterinary product for treating inflammation, particularly for treating inflamed tendons in horses.

Additionally, the scientific literature suggests that SOD may be useful in a wide range of clinical applications. These include prevention of oncogenesis and tumor promotion and reduction of cytotoxic and cardiotoxic effects of anti-cancer drugs (Oberley, L. W. and Buettner, G. R., Cancer Research 39, 1141-1149 (1979)); protection of ischemic tissues (McCord, J. M. and Roy, R. S., Can. J. Physiol. Pharma. 60, 1346-1352 (1982)), and protection of spermatozoa (Alvarez, J. G. and Storey, B. T., Biol. Reprod. 28, 1129-1136 (1983)). In addition, there is a great interest in studying the effect of SOD on the aging process (Talmasoff, J. M., Ono, T. and Cutler, R. G., Proc. Natl. Acad. Sci. USA 77, 2777-2782 (1980)).

The present invention also relates to using human superoxide dismutase analogs to catalyze the reduction of superoxide radicals in the presence of $H^+$, to hydrogen peroxide and molecular oxygen. In particular, the present invention concerns using hSOD analogs to reduce reperfusion injury following ischemia and prolong the survival period of excised isolated organs. It also concerns the use of hSOD or analogs thereof to reduce injury on reperfusion following organ transplantation and spinal cord ischemia. These analogs may also be used for bronchial pulmonary dysplasia.

The human CuZn superoxide dismutase and analogs thereof of the present invention are commercially advantageous in that they are less toxic than orgotein and have enhanced stability to lyophilization while retaining their enzymatic activity.

SUMMARY OF THE INVENTION

A plasmid for the production of superoxide dismutase or analog thereof which upon introduction into a suitable bacterial host cell containing the thermolabile repressor $C_I$ renders the host cell capable, upon increasing the temperature of the host cell to a temperature at which the repressor is inactivated of effecting expression of DNA encoding superoxide dismutase or the analog and production of superoxide dismutase or the analog comprising:

a double-stranded DNA molecule which includes in 5' to 3' order the following:

a DNA sequence which contains the promoter and operator $P_LO_L$ from lambda bacteriophage;

the N utilization site for binding antiterminator N protein produced by the host cell;

a first restriction enzyme site permitting replacement of the DNA sequence containing the ribosomal binding site which follows thereafter;

a DNA sequence which contains a ribosomal binding site for rendering the mRNA of the gene encoding superoxide dismutase or analog thereof capable of binding to ribosomes within the host cell;

an ATG initiation codon;

a second restriction enzyme site;

a gene encoding superoxide dismutase or the analog thereof in phase with the ATG initiation codon;

and which additionally includes a DNA sequence which contains an origin of replication from a bacterial plasmid capable of autonomous replication capable of autonomous replication in the host cell and a DNA sequence which contains a gene associated with a selectable or identifiable phenotypic trait which is manifested when the plasmid is present in the host cell, the distance between the 3' end of the $P_LO_L$ promoter and operator sequence and the 5' end of the N utilization site being less than about 80 base pairs and the distance between the 3' end of the N utilization site and the 5' end of the ribosomal binding site being less than about 300 base pairs.

The plasmids of the invention can be introduced into suitable hosts where the gene for superoxide dismutase or SOD analog can be expressed and the superoxide dismutase or analogs thereof produced. The presently preferred plasmids for human superoxide dismutase are: pSOD $β_1T_{11}$, pSOD $βMAX_{10}$ and pSOD$βMAX_{12}$. Preferred hosts include *Escherichia coli*, in particular, autotrophic *E. coli* A1645; prototrophic *E. coli* A4200 and A4255, and lytic *E. coli* A4048.

A1637 was obtained from C600 by inserting transposon containing tetracycline resistance gene within the galactose operon as well as the lambda system for expression which is close to galactose operon. C600 is available from the American Type Culture Collection, as ATCC Accession No. 23724.

A1645 was obtained from A1637 by selection for Gal+ (ability to ferment galactose) as well as loss of tetracycline resistance. It still contains the lambda expression system but part of the transposon has been removed by selection. Its phenotype is C600 r⁻m⁺ gal⁺ thr⁻ leu⁻ lacZ⁻ b1 (λcI857 ΔH1 ΔBamH1 N+).

A1645 is presently a more preferred strain for expression of genes encoding superoxide dismutase or analogs thereof. It has been deposited with the American Type Culture Collection in Rockville, Md., U.S.A. containing various plasmids as described more fully hereinafter. All deposits were made pursuant to the Budapest Treaty on the International Recognition of the Deposit of Microorganisms except that pBR322 and pBRM are fully available from the American Type Culture Collection as ATCC Accession Nos. 37017 and 37283, respectively, the D4 was deposited under ATCC Accession No. 31826 in connection with the filing of a U.S. patent application.

Prototrophic strains of *Escherichia coli* which enable high level polypeptide expression even when grown in a minimal media may also be used as hosts for the vectors of this invention. Preferred prototrophic strains include A4200 and A4255. Strain A4255 containing the plasmid p9200 has been deposited with the ATCC under Accession No. 53215. Even more preferred are biotin independent prototrophic strains such as A4346 containing the plasmid pGH44 which has been deposited with the ATCC under Accession No. 53218.

Lytic strains of *Escherichia coli* may also be used as hosts for the vectors of this invention. Suitable lytic strains include those which produce, at the temperature at which the polypeptide is produced but at a rate slower than that at which the polypeptide is produced, a substance e.g., an enzyme like endolysin which will cause the cell to lyse.

This permits the cell to produce relatively large amounts of the desired polypeptide before the amount of the lysing substance produced reaches the level which causes cell lysis. Examples of suitable lytic strains include those containing PlcI$^{ts}$ plasmid such as strain A4048 containing pGH44 which has been deposited with the ATCC under Accession No. 53217.

The resulting host vector systems can be employed to manufacture superoxide dismutase or superoxide dismutase analogs. Host cells containing the plasmids are grown under suitable conditions permitting production of superoxide dismutase or the analog and the resulting superoxide dismutase or analog is recovered. Using the host vector systems, analogs of human superoxide dismutase have been prepared. Veterinary and pharmaceutical compositions containing these SOD analogs and suitable carriers have also been prepared. These superoxide dismutase analogs have been used to catalyze the following reaction:

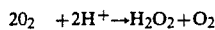

More particularly, these analogs have been used to reduce injury caused by reperfusion following ischemia or organ transplantation, reduce cardiac infarct size, increase the survival time of excised isolated organs, and reduce spinal cord injury.

DESCRIPTION OF THE FIGURES

The restriction maps for each of the plasmids shown in FIGS. 1-31 do not identify all restriction sites present on each plasmid. In some cases restriction sites are shown in one figure but not in another. However, in all cases those restriction sites necessary for a complete understanding of the invention are shown.

Construction of pAL500

Figure 1:
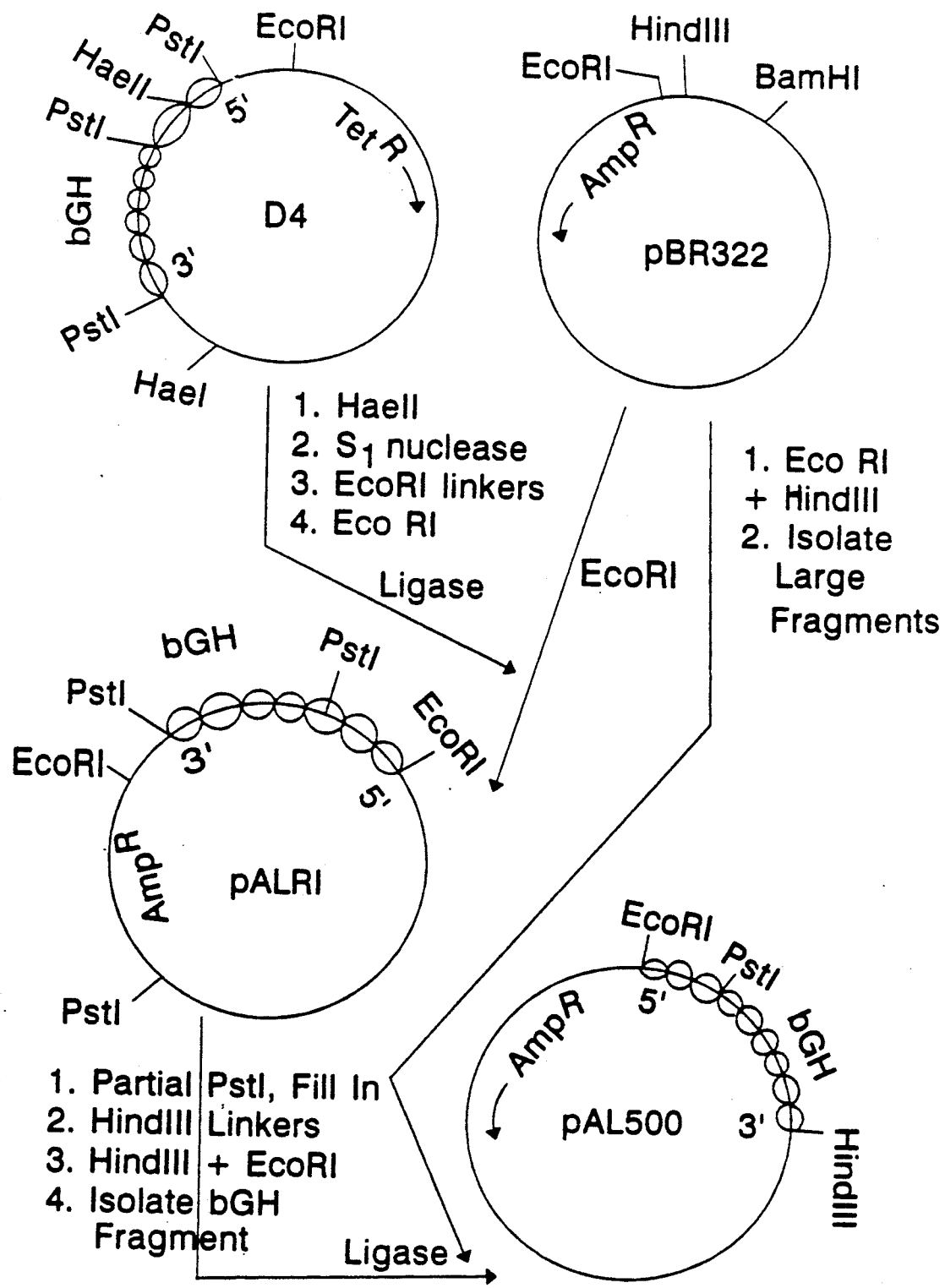
FIG. 1

A plasmid containing bGH cDNA, D4 (ATCC No. 31826), was digested with HaeII. The resulting 1600 base pair large fragment was purified and digested at 37° C. for 5 minutes with S1 exonuclease. A synthetic EcoRI linker with the sequence:

```
GGAATTCC
CCTTAAGG
``` was attached to the ends of the resulting fragments by ligation. The ligation mixture was cleaved with EcoRI and inserted into pBR322 (ATCC No. 37017) which had been cleaved with EcoRI. A clone, pALRI, was obtained which upon cleavage with EcoRI released a 1200 base pair fragment with the sequence:

```
AATTCCCAGCCATG ...
    GGGTCGGTAC ...
``` at the 5' end. This sequence demonstrates that pALRI contains an EcoRI restriction site which includes the TTC codon for residue number 1 (phenylalanine) of natural bGH. pALRI was subjected to a partial cleavage with PstI. The digest was treated with DNA polymerase I large fragment (Klenow) and HindIII linkers with the sequence:

```
GAAGCTTC
CTTCGAAG
``` were attached by ligation. The ligation mixture was cleaved with EcoRI and HindIII. The fragment containing bGH cDNA was isolated and subcloned into pBR322 between the EcoRI and HindIII restriction sites to give pAL500 (ATCC No. 39782).

FIG. 2

Construction of pRO211 and pRO12

The plasmid pJH200 (ATCC No. 39783) was partially digested with NdeI, treated with DNA polymerase I (Klenow) to fill in the ends and the resulting ends were religated to form the expression vector pRO211. The expression vector pRO211 was digested with NdeI and HindIII, the large fragment isolated and ligated to an NdeI-HindIII bGH fragment isolated from pAL500 (ATCC No. 39782) to give pRO12. (The NdeI-HindIII fragment was produced from pAL500 by digesting it with EcoRI and ligating to the ends of the digestion product synthetic linkers with the sequence:

```
TATGGATC
  ACCTAGTTAA
```

The ligation mixture was digested with NdeI and HindIII and the resulting NdeI-HindIII bGH fragment isolated.)

FIG. 3

Construction of pSAL 5200-6 pRO12 (FIG. 2) was partially digested with PvuII followed by digestion with NdeI to eliminate a 72 base pair fragment. A synthetic DNA fragment coding for the first 24 amino acids of the N-terminus of authentic bGH was ligated to the digested pRO12.

The synthetic DNA fragment was constructed by annealing two phosphorylated synthetic single-stranded DNAs of the sequence:

CCATATGTTCCCAGCCATGTCCTTGTCCGGCCTGTTTGCCAACGCTGTGCTC-3'
3'-      GCGACACGAGGCCCGAGTCGTGGACGTGGTCGACG.

The annealed fragment was treated with DNA polymerase I (Klenow) in the presence of all four deoxyribonucleoside triphosphates in order to form the full length double-stranded DNA. The fragment was digested with PvuII and NdeI before ligation to pRO12 to form pSAL 5200-6.

FIG. 4

Construction of p3008 p3008 (ATCC No.39804) was constructed by ligating NdeI-digested pRO211 (FIG. 2) with the pGH fragment isolated from an NdeI digest of the plasmid ppGH-NdeI/RI.

ppGH-NdeI/RI contains full length pGH cDNA to both ends of which NdeI sites have been added by means of synthetic linkers.

FIG. 5

Construction of p5002 p5002 was constructed by tripartite ligation of a dimerized synthetic linker and the 2 cGH fragments isolated from an NdeI and BanII digest of the plasmid pcGH-NdeI/RI. The ligation mixture was digested with NdeI and then ligated to the expression vector pRO211 (FIG. 2) after it had been restricted with NdeI. A colony containing the plasmid p5002 was isolated.

The synthetic linker was constructed from two single-stranded synthetic DNAs of the sequence:

TATGTTCCCTGCCATGCCCCTCTCCAACCTGTTTGCCAACGCTGTGCTGAGGGCT
  ACAAGGGACGGTACGGGGAGAGGTTGGACAAACGGTTGCGACACGACTC

The linker was phosphorylated before ligation. The linker codes for the first 18 amino acids of the N-terminus of the authentic cGH.

The plasmid pcGH-NdeI/RI contains full length cGH cDNA at the 5' end of which there is an EcoRI restriction site and at the 3' end of which there is an NdeI restriction site. These restriction sites were added by means of synthetic linkers.

FIG. 6

Construction of pGH44 and pGH50 pRO12 (FIG. 2) was digested with HindIII. The linear form DNA (form III) was purified from agarose gel and ligated to a HindIII-HindIII fragment of about 1200 base pairs which contains the rRNA operon transcription termination sequences $T_1T_2$. The $T_1T_2$ HindIII-HindIII fragment was isolated from plasmid pPS1 (ATCC No. 39807) which had been digested with HindIII. The resulting plasmid pHG44 (ATCC No. 39806) contains the $T_1T_2$ sequences at the 3' end of the recombinant (rec) bGH sequence.

The plasmid pSK434 (ATCC No. 39784) containing the $\lambda cI^{434}$ repressor sequences was digested with HpaII. The $\lambda cI^{434}$ HpaII-HpaII fragment was isolated and ligated to pHG44 which had been digested with ClaI. The resulting plasmid pHG50 (ATCC No. 39805) contains the $T_1T_2$ transcription termination sequences and the $\lambda cI^{434}$ repressor sequence.

FIG. 7

Construction of p8300-10A

The plasmid p8300-10A (ATCC No. 39785) which expresses an analog of the natural phenylalanine form of bGH having methionine at the N-terminus (met-phe bGH) was prepared as follows. The plasmid p7200-22 contains the $\lambda P_L$ promoter and ribosomal binding site derived from pJH200 (ATCC No. 39783), DNA encoding met-phe bGH and the $T_1T_2$ rRNA termination sequences. The ClaI-ClaI fragment containing the $\lambda P_L$ promoter, the $C_{II}$ ribosomal binding site, the met-phe bGH gene and the $T_1T_2$ transcription termination sequences was inserted into the unique ClaI site of plasmid pOP1Δ6, a constitutive high copy number plasmid, to form p8300-10A.

FIG. 8

Construction of pSAL-130/5 and pSAL-170/10

The plasmid pGH44 (ATCC No. 39806) expressing met-asp-gln bGH protein was digested with NdeI and HindIII. The resulting NdeI-HindIII bGH fragment was isolated and ligated to a fragment from p8300-10A (ATCC No. 39785) prepared by partial digestion with both NdeI and HindIII. Such a ligation replaces the met-phe bGH gene fragment with the met-asp-gln bGH gene fragment. The plasmid so obtained, pSAL-130/5, expresses rec bGH. pSAL-170/10 was obtained by treating the EcoRI-AvaI fragment containing the $Tet^R$ gene of pBR322 plasmid (ATCC No. 37017) with DNA polymerase I (Klenow) and inserting it into pSAL-130/5 which had been digested with BamHI and filled in with DNA polymerase I (Klenow).

FIG. 9

Construction of pSAL-210/4

Linear form DNA (form III) was prepared by partial ClaI digestion of pSAL-170/10. It was purified from an agarose gel and ligated to a HpaII-HpaII $cI^{434}$ gene fragment with was isolated from a HpaII digest of the plasmid pSK434 (ATCC No. 39784).

FIG. 10

Construction of pSAL 5600-1 pSAL 5200-6 (FIG. 3) was digested with HindIII. The linear form DNA (form III) was purified from an agarose gel and ligated to a HindIII-HindIII fragment of about 1200 base pairs which contains the rRNA operon transcription termination sequences, $T_1T_2$. The $T_1T_2$ HindIII-HindIII fragment was isolated from the plasmid pPS1 (ATCC No. 39807) which was digested with HindIII. The resulting plasmid pSAL 5600-1 contains the $T_1T_2$ sequences at the 3' end of the met-asp-gln bGH sequence.

FIG. 11

Construction of p3009

Figure 4:
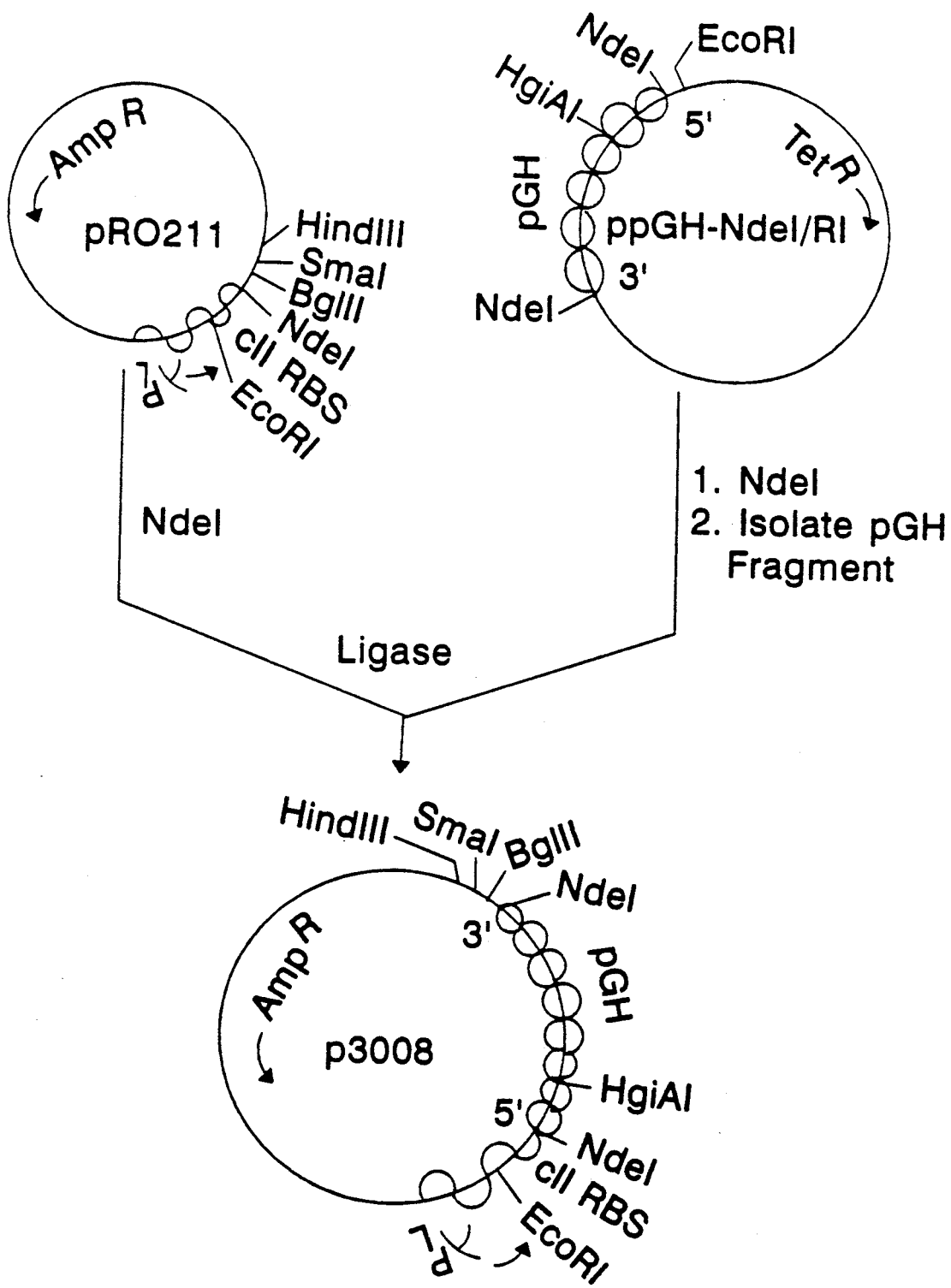

The NdeI-NdeI pGH fragment was isolated from plasmid p3008 (ATCC No. 39804) (FIG. 4). The fragment was inserted into the unique NdeI site of the expression vector p579 (FIG. 19) which had been digested with NdeI. The resulting plasmid p3009 expresses an analog of natural porcine growth hormone protein having a methionine residue added at the N-terminus.

FIG. 12

Construction of p5003

The NdeI-NdeI cGH fragment was isolated from plasmid p5002. The fragment was inserted into the unique NdeI site of the expression vector p579 (FIG. 19) which had been digested with NdeI. The resulting plasmid p5003 (ATCC No. 39792) expresses an analog of natural chicken growth hormone protein having a methionine residue added at the N-terminus.

FIG. 13

Construction of pSODα2

The pJH200 (ATCC No. 39783) expression vector was digested with NdeI. The 550 base pair NdeI fragment containing the $\lambda P_L$ promoter and $C_{II}$ ribosomal binding site was isolated and inserted into the unique NdeI site of plasmid pSOD NH-10 which had been digested with NdeI. (Plasmid pSOD NH-10 is derived from a cDNA clone of human SOD [Lieman-Hurwitz, J., et al., PNAS (1982) 79: 2808]) The resulting plasmid pSOD NH-550 was digested with AluI. (Only the relevant AluI site is shown in the figure.) The large AluI fragment containing the $\lambda P_L$ promoter and the SOD gene was isolated. BamHI linkers were attached and the resulting fragment was digested with BamHI. The BamHI digestion product was inserted into the unique BamHI site of pBRM (ATCC No. 37283) to form pSODα2 (ATCC No. 39786).

FIG. 14

Construction of pSODα13 and pSODβ1

The plasmid pSODα2 (ATCC No. 39786) was partially digested with EcoRI and the resulting linear form DNA was isolated from an agarose gel. The purified DNA was filled in which DNA polymerase I (Klenow) and religated. The resulting clone pSODα13 contains one EcoRI site located at the 5' end of the ribosomal binding site. A fragment containing the β-lactamase promoter and ribosomal binding site was isolated from plasmid pBLA11 (ATCC No. 39788) which had been digested with EcoRI and AluI. The 200 base pair fragment was ligated to the large fragment isolated from pSODα13 which had been digested with NdeI, filled in with DNA polymerase I (Klenow) and then digested with EcoRI. The resulting plasmid pSODβ1 contains the ribosomal binding site of the β-lactamase gene and the $\lambda P_L$ promoter.

FIG. 15

Construction pSODβ1T$_{11}$

Plasmid pBR322 (ATCC No. 37017) was digested with EcoRI and AvaI. The resulting DNA was filled in with DNA polymerase I (Klenow). The Tet$^R$ gene fragment was then isolated and ligated to the large fragment isolated from pSODβ1 (FIG. 14) plasmid which had been digested with PstI followed by a partial BAMHI digest and then filled in with DNA polymerase I (Klenow). The resulting plasmid pSODβ1T$_{11}$ (ATCC Accession No. 53468) contains the TET$^R$ gene.

FIG. 16

Construction of pSODβ$_1$TT-1

The rRNA $T_1T_2$ transcription termination fragment was isolated from plasmid pPS1 (ATCC No. 39807) which had been digested with HindIII and filled in with DNA polymerase I (Klenow). The fragment was ligated to plasmid pSODβ$_1$T$_{11}$ (FIG. 15) which had been partially digested with BamHI and filled in with DNA polymerase I (Klenow).

FIG. 17

Construction of pSODβ$_1$-BA2

A synthetic DNA fragment with the sequence:

```
5'-AATTCAATAATATTGAAAAAGGAAGAG-3'
   GTTATTATAACTTTTTCCTTCTCAT
``` which is similar to the sequence of the natural β-lactamase ribosomal binding site, was phosphorylated and ligated to the large fragment of pSODα13 plasmid (FIG. 14) which had been digested with NdeI and EcoRI.

FIG. 18

Construction of pTV-188

Plasmid pApoE-EX2 (ATCC No. 39787) was digested with NdeI and then fragments filled in with DNA polymerase I (Klenow). The resulting ApoE gene fragment was isolated and inserted into the unique blunt end StuI site of the pSOD⊕$_1$T$_{11}$ plasmid (FIG. 15) The resulting plasmid pTV-188 expresses an ApoE fused protein.

FIG. 19

Construction of p579

The rRNA operon $T_1T_2$ transcription termination fragment was isolated from plasmid pPS1 (ATCC No. 39807) which had been digested with HindIII. The $T_1T_2$ fragment was inserted into the unique HindIII site of pRO211 (FIG. 2) which had been digested with HindIII. The resulting expression vector, p579, contains the $\lambda P_L$ promoter, the $C_{II}$ ribosomal binding site, followed by the $T_1T_2$ transcription termination signals.

FIG. 20

Construction of pTV-170

The NdeI-NdeI ApoE fragment was isolated from plasmid pApoE-EX2 (ATCC No. 39787) and inserted into the unique NdeI site of the expression vector p579 (FIG. 19) which had been digested with NdeI. The resulting plasmid pTV-170 expresses an analog of natural human ApoE protein having a methionine residue added at the N-terminus.

FIG. 21

Construction of pTV-190

The plasmid pTV-170 (FIG. 20) was partially digested with NdeI and filled in with DNA polymerase I (Klenow). The isolated linear form DNA was religated to yield the plasmid pTV-190 which was analyzed and found to have only one NdeI site at the 5' end of the ApoE gene.

FIG. 22

Construction of pTV-194

The β-lactamase promoter and ribosomal binding site fragment was isolated from plasmid pBLA11 (ATCC No. 39788) after digestion with EcoRI and AluI. This fragment was ligated to the large fragment of pTV-170 (FIG. 20) plasmid which had been digested with NdeI, filled in with DNA polymerase I (Klenow) and then digested with EcoRI.

FIG. 23

Construction of pSAL 160-5

An AvaI-AvaI fragment containing the ApoE DNA sequence was isolated from pTV-170 (FIG. 21) which was digested with AvaI. The fragment was filled in with DNA polymerase I (Klenow) and isolated on agarose gel. The purified ApoE fragment was inserted into the PstI site of the pTV 104(2) plasmid (ATCC No. 39384) which was partially digested with PstI and filled in with DNA Polymerase I (Klenow). The resulting plasmid is designated pSAL 160-5.

FIG. 24

Construction of pTV-214

A synthetic fragment containing the first 14 amino acids of human growth hormone with the sequence:

```
TATGTTCCCAACCATTCCATTATCCCGTCTGTTCGACAACGC
 ACAAGGGTTGGTAAGGTAATAGGGCAGACAAGCTGTTGCGAT
``` was phosphorylated using $\gamma$-$^{32}$p-ATP and polynucleotide kinase. The phosphorylated linker was inserted into the unique NdeI site of pTV-190 plasmid which had been digested with NdeI.

FIG. 25

DNA Sequence of the Cloned hCuZnSOD in pSODβ$_1$T$_{11}$

Figure 15:
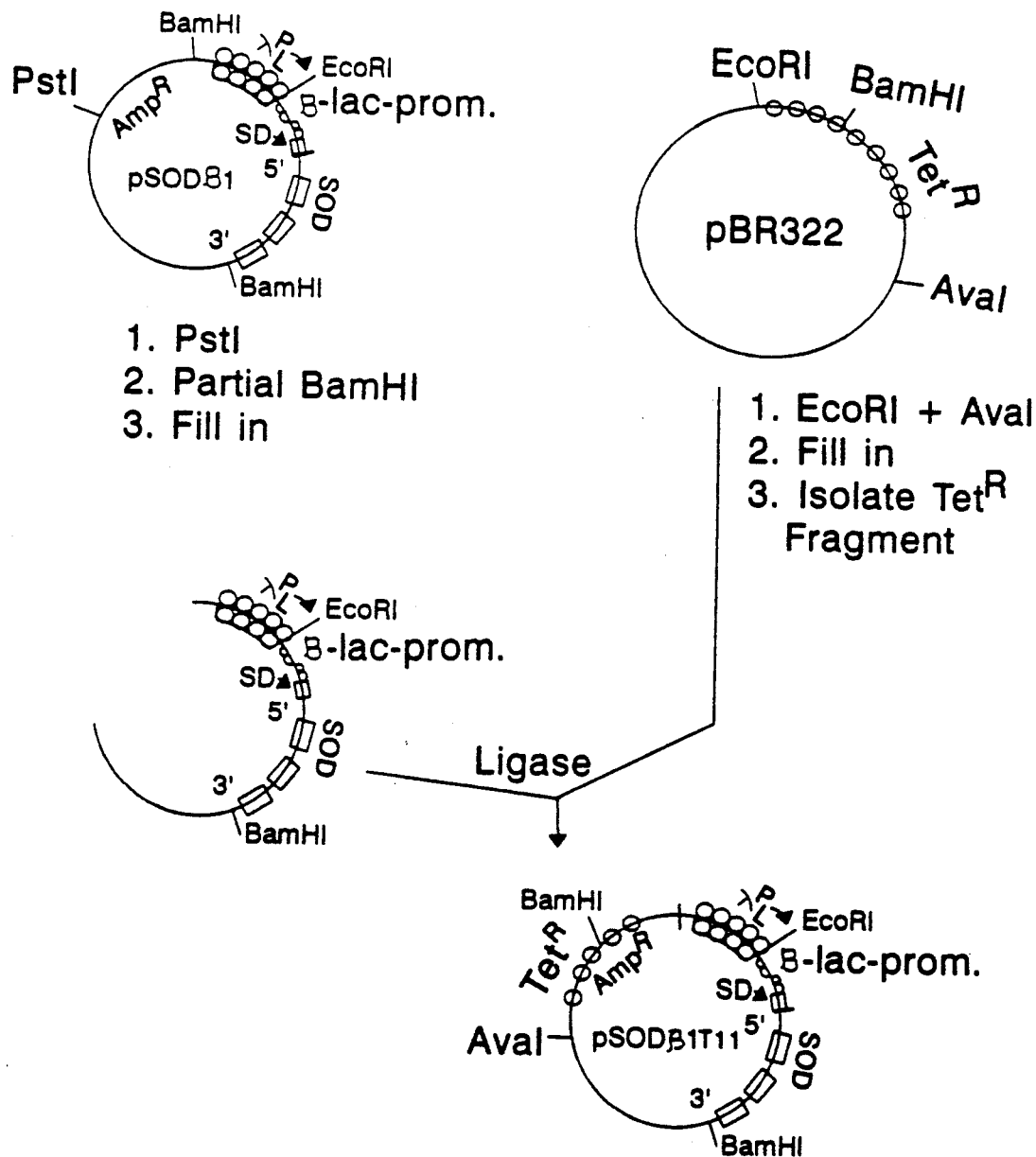
Figure 16:
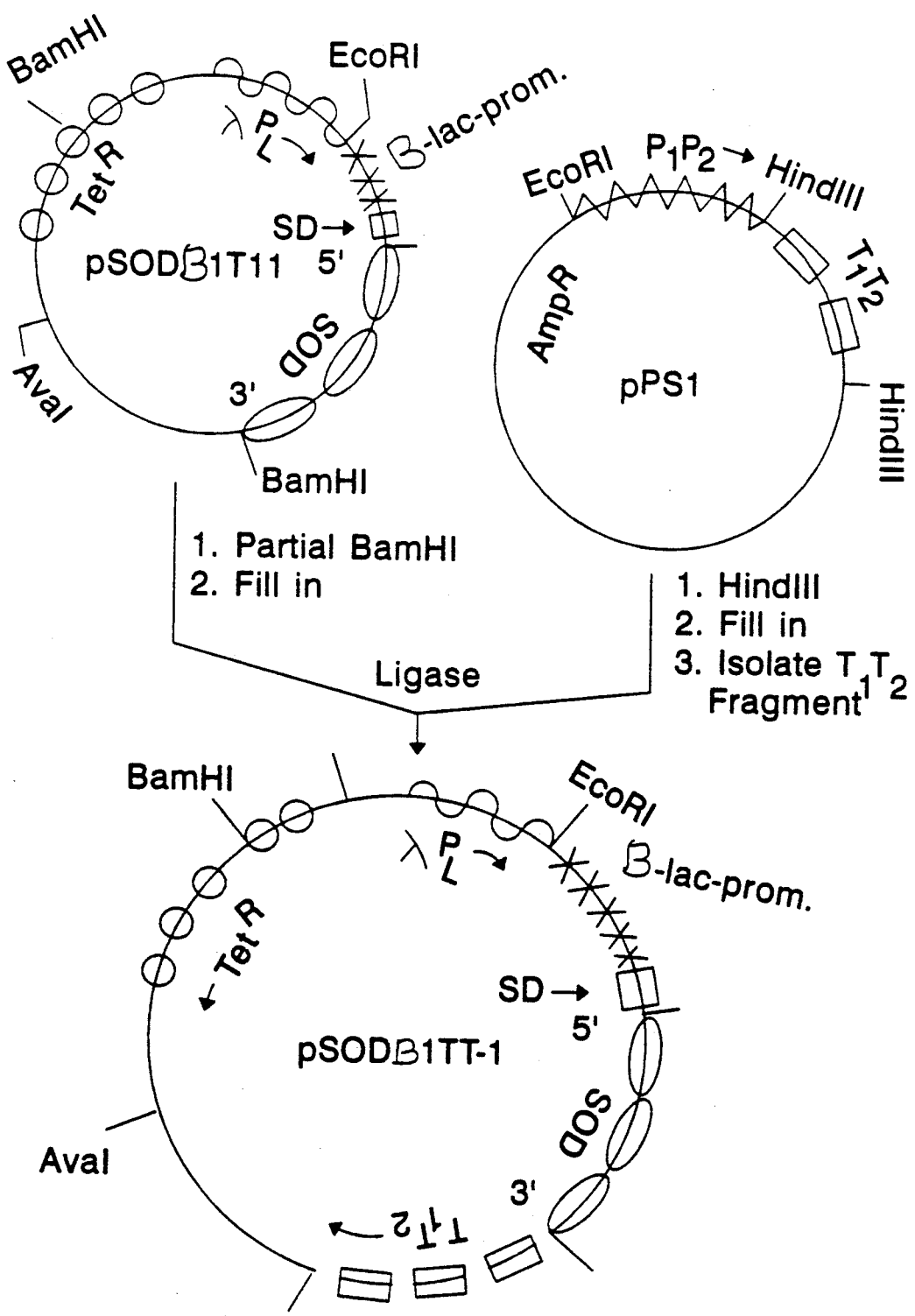

FIG. 50 shows the presence and location of two ATG codons located at the 5' end of the cloned human CuZn SOD gene in pSODβ$_1$T$_{11}$ (ATCC Accession No. 53468) which was constructed as shown in FIG. 15.

FIG. 26

Construction of pΔRB Plasmid

Tet$^R$ expression vector, pΔRB, was generated from pSODβ$_1$T$_{11}$ (ATCC Accession No. 53468) by complete digestion with EcoRI followed by partial cleavage with BamHI restriction enzymes. The digested plasmid was ligated with synthetic oligomer

```
5'-AATTCCCGGGTCTAGATCT-3'
3'-    GGGCCCAGATCTAGACTAG-5'
``` resulting in pΔRB containing the λ PL promoter. pΔRB contains unique restriction sites for insertion of ribosomal binding sites and genes downstream of the P$_L$ promoter.

FIG. 27

Construction of pβUN

Figure 27:
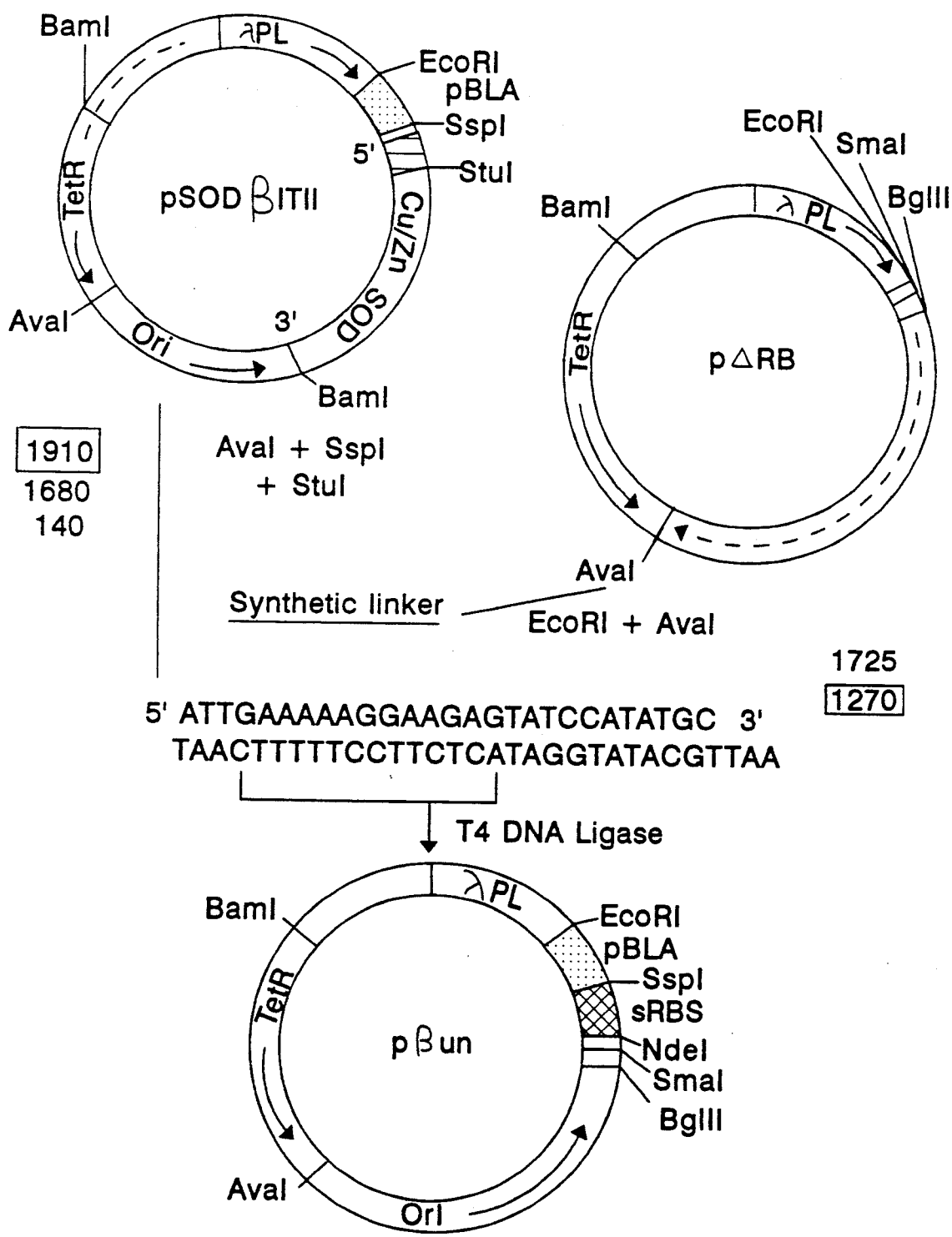
Figure 29:
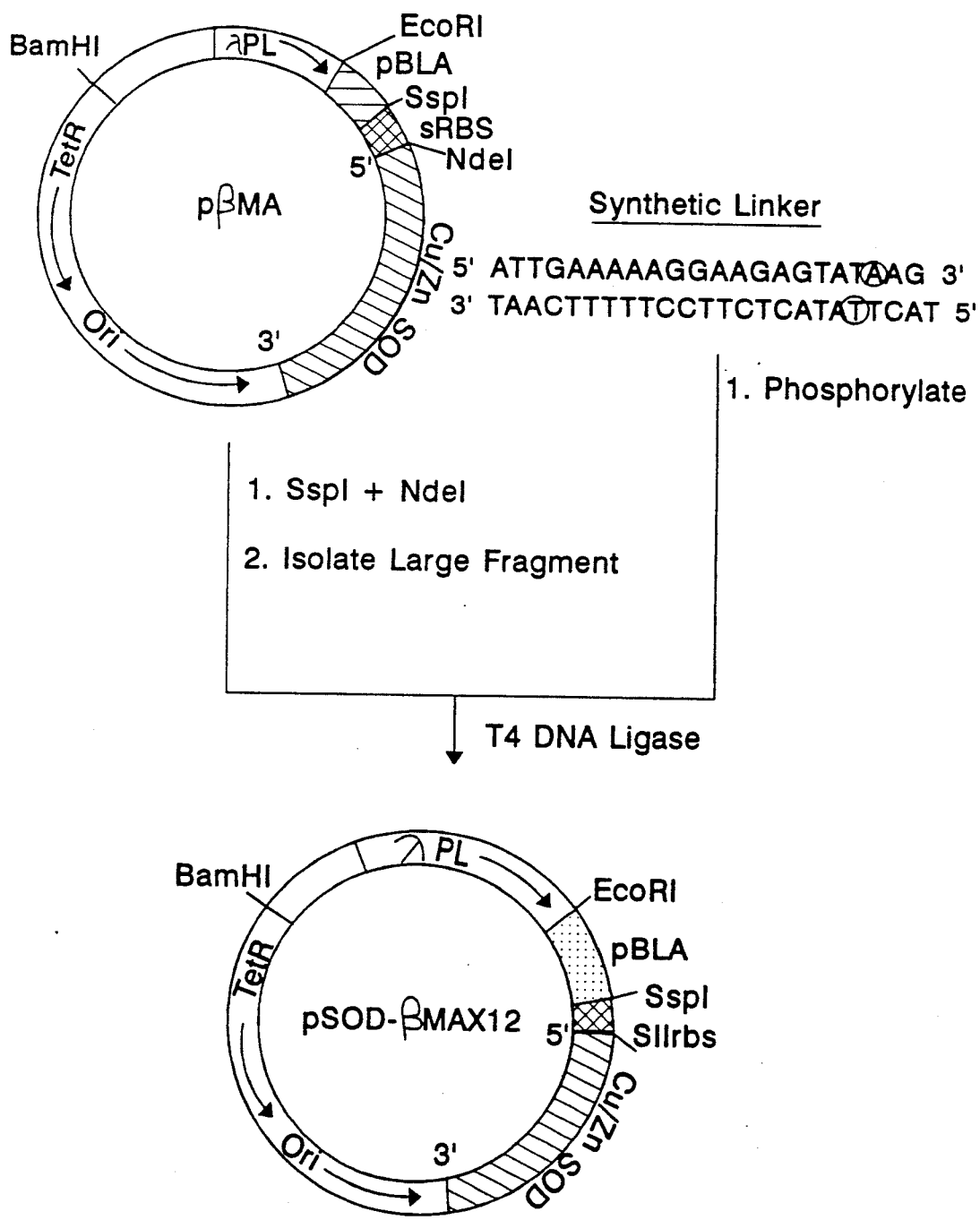

Construction of pβUN, a general purpose expression vector, containing the λ P$_L$ promoter and β-lactamase promoter and RBS is shown in FIG. 27. Unique NdeI site followed by SmaI, XbaI and BglII sites were introduced downstream of the β-lactamase RBS for insertion of any desired gene. It should be pointed out that 3 nucleotide changes were made at the 3' end of the β-lactamase RBS-, one to eliminate the first possible ATG (C instead of G) and two other changes to form the NdeI site (CA instead of AG).

FIG. 28

Construction of pSODβMA

The entire coding region of human CuZn SOD on a NdeI-BamHI fragment isolated from pSODα13, was inserted between the unique NdeI and BglII sites of pβUN as depicted in FIG. 28. The resulting vector, pSODβMA, is an intermediate plasmid used in the construction of the expression plasmids pSOD-βMAX$_{12}$ and pSOD-βMAX$_{10}$.

FIG. 29

Construction of pSOD-βMAX$_{12}$

The plasmid pSOD-βMAX$_{12}$ was constructed from pSOD-βMA by replacement of part of the ribosomal binding site with synthetic DNA. This causes a single base change in the sequence of the ribosomal binding site. The plasmid directs exclusive high level expression of a non-acetylated SOD analog which has an amino acid sequence identical to that of natural SOD. The analog is also non-glycosylated. pSODβMAX$_{12}$ has been deposited with the American Type Culture Collection and assigned ATCC Accession No. 67177.

FIG. 30

Construction of pSOD-βMAX$_{10}$

The plasmid pSOD-βMAX$_{10}$ was constructed from pSOD-βMA by replacement of part of the ribosomal binding site with synthetic DNA. This causes a single base change in the sequence of the ribosomal binding site. The plasmid directs exclusive high level expression of a non-acetylated SOD analog which has an amino acid sequence identical to that of natural SOD. The analog is also non-glycosylated.

FIG. 31

Modification of hSOD cDNA at 5'End and Construction of pSODNH-10

Plasmid pS61-10 was digested with PstI and the small PstI-PstI 620 bp fragment containing hSOD DNA was isolated. The purified fragment was separated into two equal aliquots.

The first aliquot was treated with DNA polymerase (Klenow fragment) in order to obtain a blunt-ended fragment. The DNA fragment was ligated to HindIII phosphorylated linkers having the sequence:

```
CAAGCTTG
GTTCGAAC
``` and treated with HindIII. The fragment was then ligated to pBR322 DNA which had been digested with HindIII and treated with bacterial alkaline phosphatase. The DNA ligation mixture was used to transform E. coli strain 1061 and Amp$^R$ clones were selected. These clones were screened by in situ filter hybridization to a nicked translated radioactive probe containing the bSOD DNA sequences. One of the positive clones, pSODH3, was analyzed by restriction mapping.

The second aliquot of the 620 bp PstI-PstI fragment was digested with FokI and the 229 bp FokI-FokI fragment was isolated and ligated to a synthetic phosphorylated DNA linker having the sequence:

```
  TATGGCTACTAAA
    ACCGATGATTTCGGC
```

The DNA was then digested with NdeI and StuI. The newly formed 127 bp fragment with the synthetic linkers was ligated with T4 DNA ligase to the large DNA fragment of plasmid pSODH3 which was obtained by digestion with NdeI, StuI and SalI. The NdeI-NdeI fragment of about 2560 bp was isolated. The DNA ligation mixture was used to transform E. coli strain 1061 and Amp$^R$ transformants were selected. The clones were screened for the right plasmid construction by NdeI and HindIII double digestion. One of these clones (pSOD NH-10) was sequenced and used for the expression of the human CuZn hSOD.

DETAILED DESCRIPTION OF THE INVENTION

A plasmid has been developed which enables the achievement of enhanced levels of gene expression and polypeptide roduction. The plasmid is a double-stranded DNA molecule. Upon introduction into a suitable bacterial host cell containing the thermolabile repressor $C_I$ the plasmid renders the host cell capable, upon increasing the temperature of the host cell to a temperature at which the repressor is inactivated, of effecting expression of a desired gene inserted into the plasmid and production of a polypeptide encoded by the gene.

The plasmid includes in 5' to 3' order the following:
a DNA sequence which contains the promoter and operator $P_LO_L$ from lambda bacteriophage;
the N utilization site for binding antiterminator N protein;
a first restriction enzyme site permitting replacement of the DNA sequence containing the ribosomal binding site which follows thereafter;
a DNA sequence which contains a ribosomal binding site for rendering the mRNA of the desired gene capable of binding to ribosomes within the host cell;
an ATG initiation codon or a DNA sequence which is converted into an ATG initiation codon upon insertion of the desired gene into the vector;
a second restriction enzyme site for inserting the desired gene into the plasmid in phase with the ATG initiation codon; and
a gene encoding the desired polypeptide.

The plasmid also includes a DNA sequence which contains an origin of replication from a bacterial plasmid capable of automomous replication in the host cell and a DNA sequence which contains a gene associated with a selectable or identifiable phenotypic trait which is manifested when the plasmid is present in the host cell. The distance between the 3' end of the $P_LO_L$ promoter and operator sequence and the 5' end of the N utilization site is less than about 80 base pairs and the distance between the 3' end of the N utilization site and the 5' end of the ribosomal binding site is less than about 300 base pairs.

Another component of the plasmid is a first restriction enzyme site permitting replacement of the DNA sequence containing the ribosomal binding site which follows thereafter. Numerous such sites may be used. Suitable sites include EcoRI.

Yet another component of the plasmid is a second restriction enzyme site for insertion of the desired gene into the plasmid in phase with the ATG initiation codon. Numerous such sites may be used. Suitable sites include NdeI, ClaI, HindIII, SmaI, BglII, XbaI, SacI and AluI.

Generally it is desirable that the second restriction enzyme site also functions as the second restriction site necessary to permit replacement of the DNA sequence containing the ribosomal binding site. If the second restriction site is not also used for this purpose then the vector of this invention must also include a third restriction enzyme site after the ribosomal binding site but prior to the second restriction site.

Preferably, the plasmid contains two unique restriction enzyme sites. The first site permits replacement of the DNA sequence containing the ribosomal binding site. The second site permits insertion of the desired gene into the plasmid in phase with the ATG initiation codon. The term "unique restriction enzyme" site as employed herein means a restriction enzyme site which occurs only once in the plasmid. In a presently preferred embodiment, EcoRI is the first restriction enzyme site and NdeI is the second restriction enzyme site.

The preferred host for use with the plasmid is Escherichia coli. The presently preferred strains are A1637, A1645, A2602, A2097 and A1563. A1637 was obtained from C600 by inserting transposon containing tetracycline resistance gene within the galactose operon as well as the lambda system for expression which is close to galactose operon. c600 is available from the American Type Culture Collection, as ATCC Accession No. 23724.

A1645 was obtained from A1637 by selection for Gal+ (Ability to ferment galactose) as well as loss of tetracycline resistance. It still contains the lambda expression system but part of the transposon has been removed by selection. Its phenotype is C600 r⁻ m⁺ gal⁻ thr⁻ leu⁻ lacZ⁻ b1 (λcI857 ΔH1 ΔBamH1 N⁺).

A1645 is presently a more preferred strain for expression of superoxide dismutase or an analog thereof. It has been deposited with the American Type Culture Collection in Rockville, Md., U.S.A. containing various plasmids as described more fully hereinafter. All deposits were made pursuant to the Budapest Treaty on the International Recognition of the Deposit of Microorganisms except that pBR322 and pBRM are fully available from the American Type Culture Collection as ATCC Accession Nos. 37017 and 37283, respectively, and D4 was deposited under ATCC Accession No. 31826 in connection with the filing of a U.S. patent application.

A2602 and A1563 are derived from SA500. Their phenotypes are SA500 his⁻ ile⁻ gal⁺ Δ8 (λcI857 ΔH1Δ Bam N⁺) and SA500 his⁻ ile⁻ gal⁺Δ8 lacZ⁻ A21 (λcI857 int2 xis1 nutL₃ Δ H1), respectively. A2097 is derived from A1645. Its phenotype is A1645 lacΔ₁₀₂ A21 proC::Tn10.

Prototrophic strains of *Escherichia coli* which enable high level polypeptide expression even when grown in a minimal media may also be used as hosts for the vectors of this invention. Preferred prototrophic strains include A4200 and A4255. Strain A4255 containing the plasmid p9200 has been deposited with the ATCC under Accession No. 53215. Even more preferred are biotin independent prototrophic strains such as A4346 containing the plasmid pGH44 which has been deposited with ATCC under Accession No. 53218.

Lytic strains of *Escherichia coli* may also be used as hosts for the vectors of this invention. Suitable lytic strains include those which produce, at the temperature at which the polypeptide is produced but at a rate slower than that at which the polypeptide is produced, a substance e.g., an enzyme like endolysin which will cause the cell to lyse. This permits the cell to produce relatively large amounts of the desired polypeptide before the amount of the lysing substance produced reaches the level which causes cell lysis. Examples of suitable lytic strains include those containing the PlcI$^{ts}$ plasmid such as strain A4048 containing pGH44 which has been deposited with the ATCC under Accession No. 53217.

Preferably, the plasmid is a covalently closed circular double-stranded molecule. However, it is not essential that the plasmid be covalently closed.

The plasmid achieves its enhanced expression levels after the host cell is heated to a temperature at which the $C_I$ repressor protein is destroyed. A temperature above about 38° C. is effective for this purpose and since it is desired that unnecessary heat damage to the host cells be avoided to as great an extent as possible, it is generally desirable that the temperature not exceed 42° C. by more than a few degrees.

One important component of the vector is the ribosomal binding site. Suitable sites are $C_{II}$ from lambda bacteriophage having the sequence:

TAAGGAAATACTTACAT
ATTCCTTTATGAATGTA;

a mutant of $C_{II}$ from lambda bacteriophage having the sequence:

TAAGGAAGTACTTACAT
ATTCCTTCATGAATGTA;

the major head protein gene of bacteriophage lambda having the sequence:

TTTTTTTACGGGATTTTTTTATG
AAAAAAATGCCCTAAAAAAATAC;

the natural β-lactamase ribosomal binding site derived from pBR322;

a synthetic oligonucleotide having the sequence:

AATTCGAGCGCAAGGAAACAGGCTCA
GCTCGCGTTCCTTTGTCCGAGTAT;

a synthetic oligonucleotide having the sequence:

AATTCAATAATATTGAAAAAGGAAGAG
GTTATTATAACTTTTTCCTTCTCAT; and a natural ribosomal binding site derived from *Bacillus thurengensis*.

The plasmid also includes an origin or replication from a bacterial plasmid capable of autonomous replication in the host cell. Suitable such origins of replication may be obtained from a number of sources, e.g., from pBR322 or pR1.

A DNA sequence which contains a gene associated with a selectable or identifiable phenotypic trait which is manifested when the plasmid is present in the host cell is also a component of the plasmid. Suitable genes include those associated with temperature sensitivity or drug resistance, e.g., resistance to ampicillin, chloroamphenicol or tetracycline.

Relative to plasmids described previously, the plasmids of this invention may be used to obtain enhanced expression of a wide variety of genes encoding desirable polypeptide products. Suitable genes include those encoding growth hormones, e.g, bovine, porcine, chicken or human growth hormones; superoxide dismutase; apolipoprotien E or analogs of any of the preceding. By analog is meant a polypeptide having the same activity as the naturally occurring polypeptide but having one or more different amino acids added or deleted, or both, at the N-terminus of the polypeptide. However, some SOD analogs described have an amino acid sequence identical to that of mature human SOD.

The plasmid may be formed by methods well known to those of ordinary skill in the art to which the invention relates. Such methods are described in greater detail in various publications identified herein, the contents of which are hereby incorporated by reference into the present disclosure in order to provide complete information concerning the state of the art.

Figure 2:
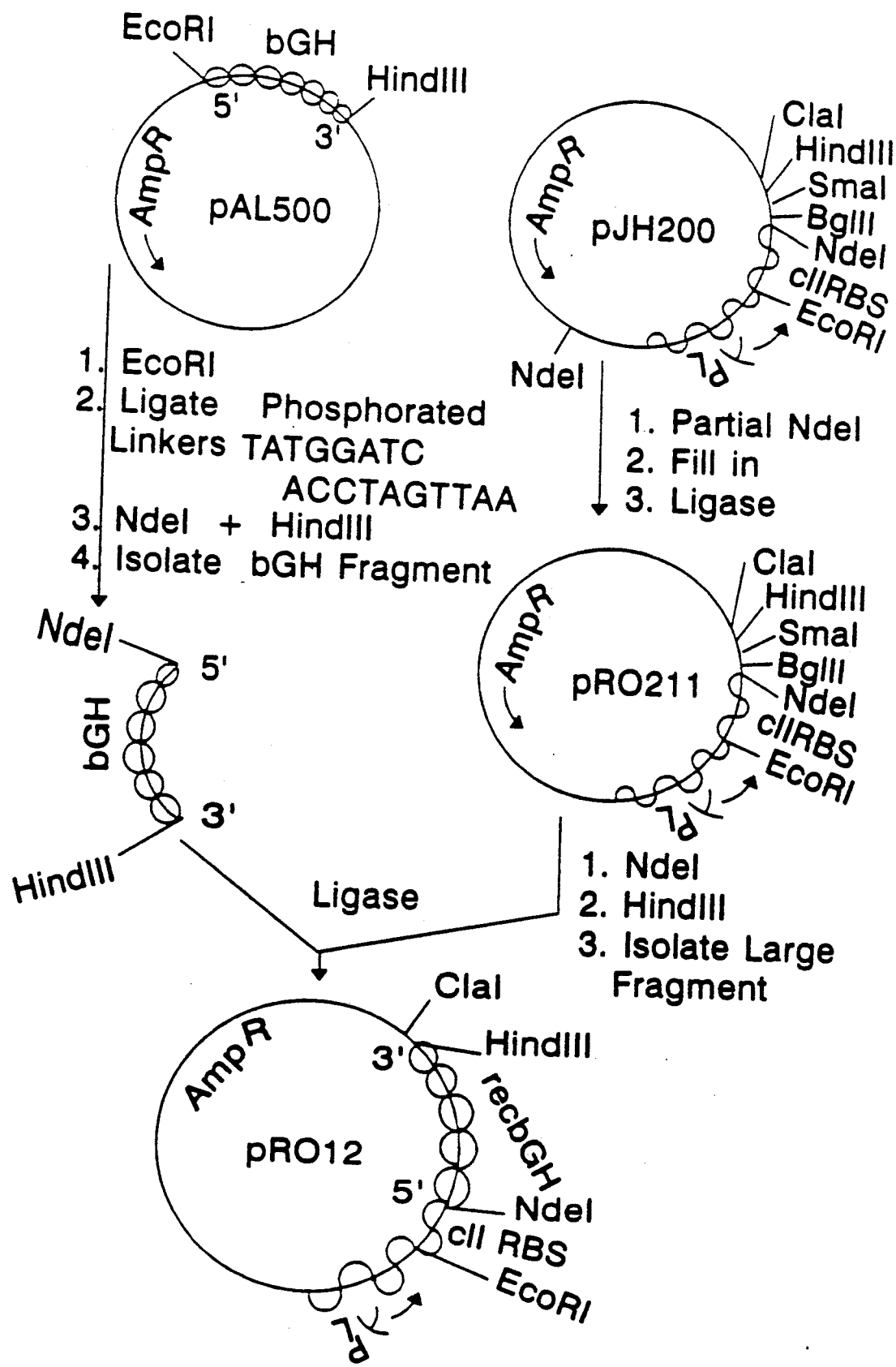

One presently preferred plasmid is pJH200 which has the restriction map shown in FIG. 2. This plasmid was introduced into *Escherichia coli* using a strain A1645 conventional transformation method. The resulting host vector system has been deposited under ATCC Accession No. 39783. A gene encoding a desired polypeptide, e.g. bovine growth hormone, may be inserted into pJH200.

A second preferred plasmid, pR0211, was constructed from a partial NdeI digest of pJH200. pR0211 has the restriction map shown in FIG. 2. Bovine growth hormone cDNA has been inserted into pRO211 by digesting the vector with NdeI and H indIII, isolating the large fragment and ligating to it bGH cDNA obtained from pAL500 (ATCC Accession No. 39782). The resulting plasmid is designated pRO12. Its restriction map is also shown in FIG. 2.

Plasmid pRO12 has been partially digested with PvuII followed by NdeI. A synthetic DNA fragment coding for the first 24 amino acids of the N-terminus of authentic bGH has been ligated to the digested pRO12. The resulting plasmid, designated pSLA 5200-6, has the restriction map shown in FIG. 3.

Figure 13:
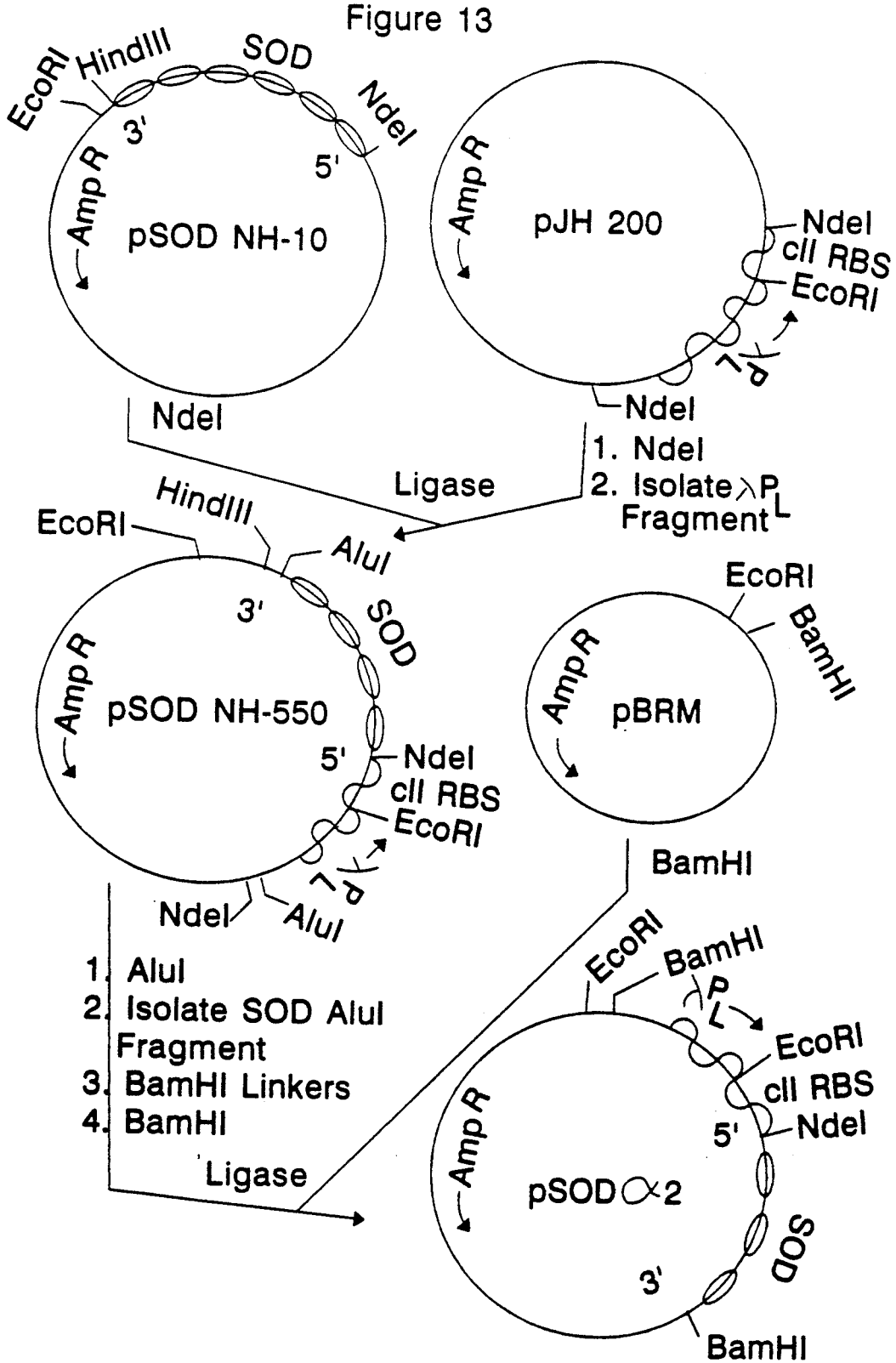

The plasmids of this invention may also be engineered to produce human superoxide dismutase (SOD) analogs thereof or mixtures of SOD analogs. A fragment of pJH200 (ATCC Accession No. 39783) containing the $\lambda P_L$ promoter and $C_{II}$ ribosomal binding site was isolated and then inserted into a plasmid pSOD NH-10 which contains the gene for human SOD to form a plasmid designated pSOD NH-550 as shown in FIG. 13. A fragment containing both the $\lambda P_L$ promoter and the SOD gene was isolated from pSOD NH-550 following digestion with AluI. After the addition of BamHI linkers and subsequent restriction with BamHI, the fragment was inserted into the unique BamHI site of pBRM. pBRM is a high copy number plasmid which has been deposited under ATCC Accession No. 37283. The resulting plasmid is designated pSODα2. It has the restriction map shown in FIG. 13. This plasmid has been deposited in E. coli strain A2097 under ATCC Accession No. 39786.

Figure 14:
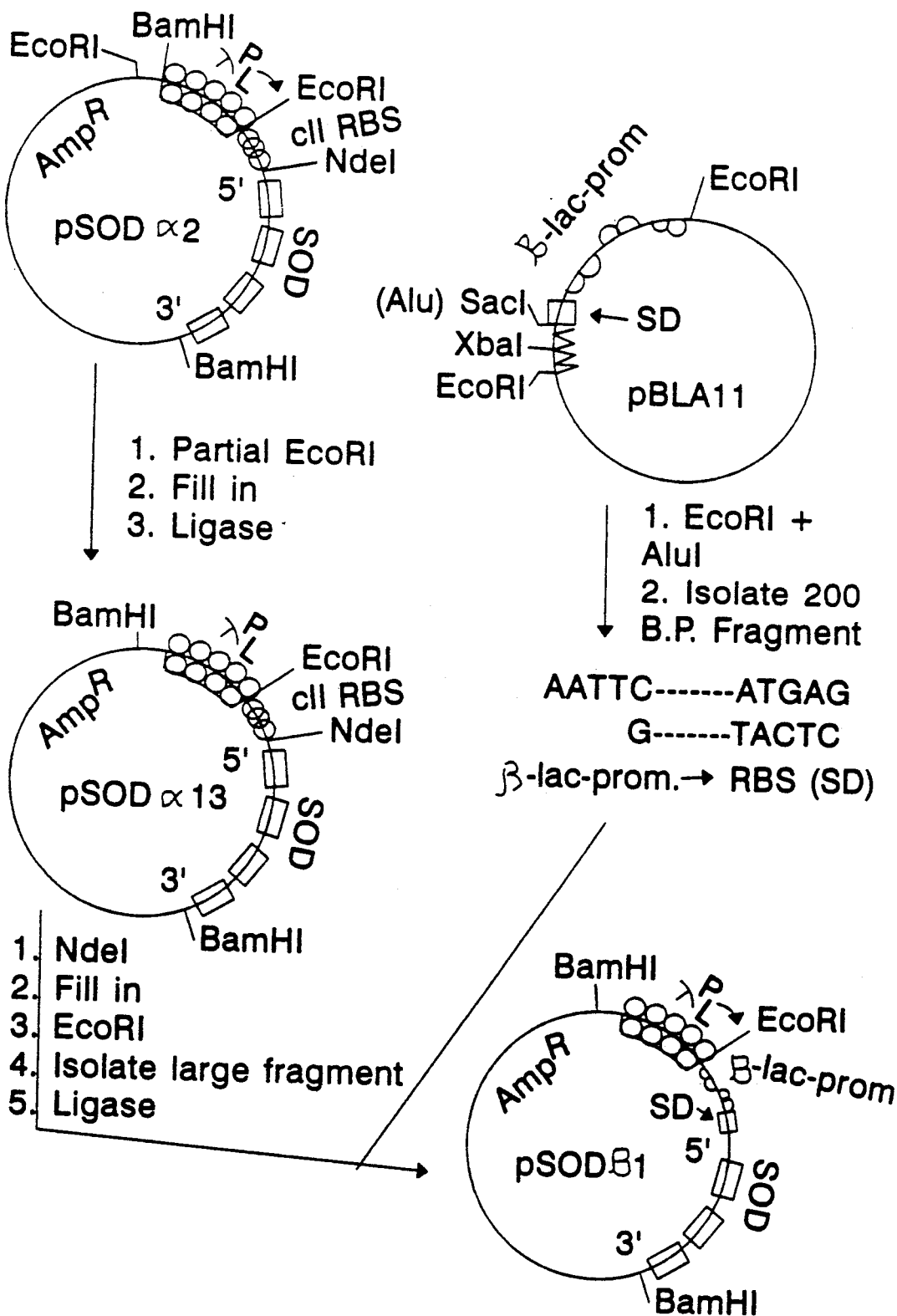

Plasmid pSODα2 (ATCC Accession No. 39786) contains the $C_{II}$ ribosomal binding site. This ribosomal binding site has been replaced with a fragment containing the β-lactamase promoter and Shine-Dalgarno ribosomal binding site isolated from an EcoRI-AluI digest of pBLA11. (Plasmid pBLA11 has the restriction map shown in FIG. 14 and has been deposited in *Escherichia coli* strain A1645 under ATCC Accession No. 39788.) The $C_{II}$ ribosomal binding site is removed from plasmid pSODα2 as shown in FIG. 14. pSODα2 is partially restricted with EcoRI, filled in with DNA polymerase I (Klenow) and religated, so that the only remaining EcoRI site in the plasmid is located at the 5' end of the $C_{II}$ RBS. The resulting plasmid, designated pSODα13 was digested with NdeI, filled in with DNA polymerase I (Klenow) and then digested with EcoRI. The large fragment was isolated and ligated to the fragment containing the β-lactamase promoter and ribosomal binding site isolated from pBLA11 to form plasmid pSODβ1.

pSODβ1 may be modified to include a tetracycline resistance gene fragment ($Tet^R$) instead of an ampicillin resistence gene fragment ($Amp^R$). the $Amp^R$ fragment was removed from pSODβ1 by digestion with PstI followed by partial BamHI. The resulting plasmid was filled in with DNA polymerase I (Klenow). The $Tet^R$ gene fragment was separately isolated from an EcoRI-AvaI digest of pBR322, filled in and ligated to the filled in plasmid. (Plasmid pBR322 is widely available, e.g. from the American Type Culture Collection as ATCC Accession No. 37017). The then resulting plasmid is designated pSODβ1T11. It has the restriction map shown in FIG. 15 and has been deposited with the American Type Culture Collection and assigned Accession No. 53468. The plasmid pSOD $\beta_1 T_{11}$ produces a mixture of two hSOD analogs: (1) the non-acetylated analog of human SOD having an amino acid sequence identical to that of natural human CuZn superoxide dismutase (non-acetylated hCuZn SOD analog); and (2) the non-acetylated analog of human SOD having the amino acid sequence identical to that of natural human CuZnSOD and having the amino acid sequence ser-met attached to the amino terminus (non-acetylated ser-met hCuZnSOD analog).

The composition of the mixture may range from about 90% to about 95% by weight of the non-acetylated hCuZnSOD analog and from about 5% to about 10% by weight of the non-acetylated ser-met hCuZnSOD analog. A preferred composition is one wherein the non-acetylated hCuZnSOD analog is greater than about 93% by eight of the mixture and the non-acetylated ser-met hCuZnSOD analog is less than about 7% by weight of the mixture. A more preferred composition is one wherein the non-acetylated hCuZnSOD analog is approximately 95% by weight of the mixture and the non-acetylated ser-met hCuZnSOD analog is approximately 5% by weight of the mixture.

Other plasmids which may be used to produce human superoxide dismutase or analogs thereof are pSODβ-$MAX_{12}$ and pSODβ$MAX_{10}$. The construction of these plasmids is shown in FIGS. 26–30. Each of these plasmids exclusively produces the non-acetylated hSOD analog having an amino acid sequence identical to that of natural human hCuZnSOD.

Figure 17:
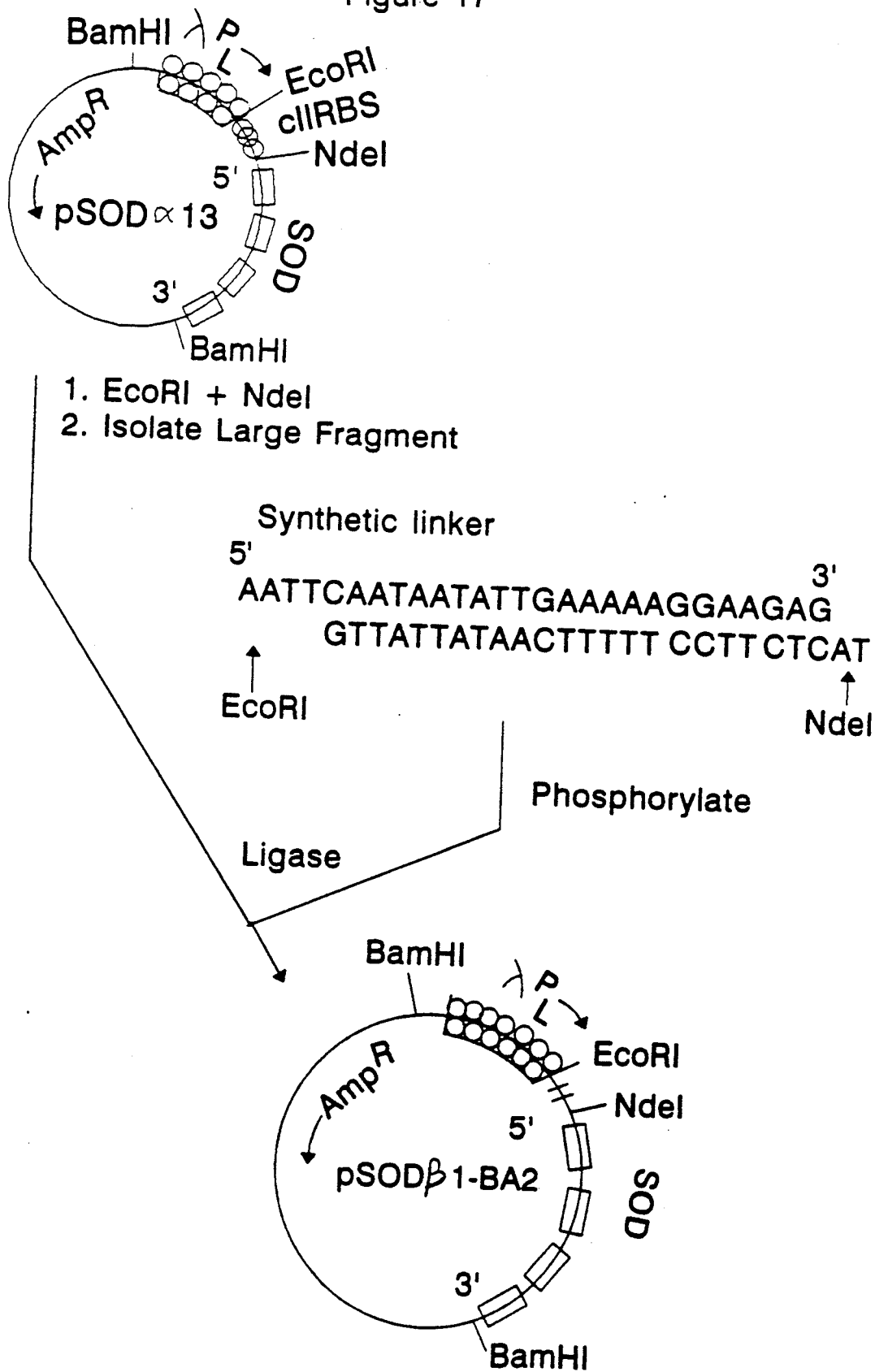

One further plasmid which may be used to produce human superoxide dismutase is designated pSOD $\beta_1$-BA2. Its construction from pSODα13 is shown in FIG. 17.

The vector of this invention, e.g. pRO211 may also be engineered to produce porcine or chicken growth hormones. Thus, as shown in FIG. 4, porcine growth hormone cDNA was isolated from an NdeI digest of ppGH-NdeI/RI. The resulting fragment containing the pGH gene was ligated to an NdeI digest of pRO211. The resulting plasmid, designated p3008, has been deposited in E. coli strain A2097 under ATCC Accession No. 39804.

Figure 5:
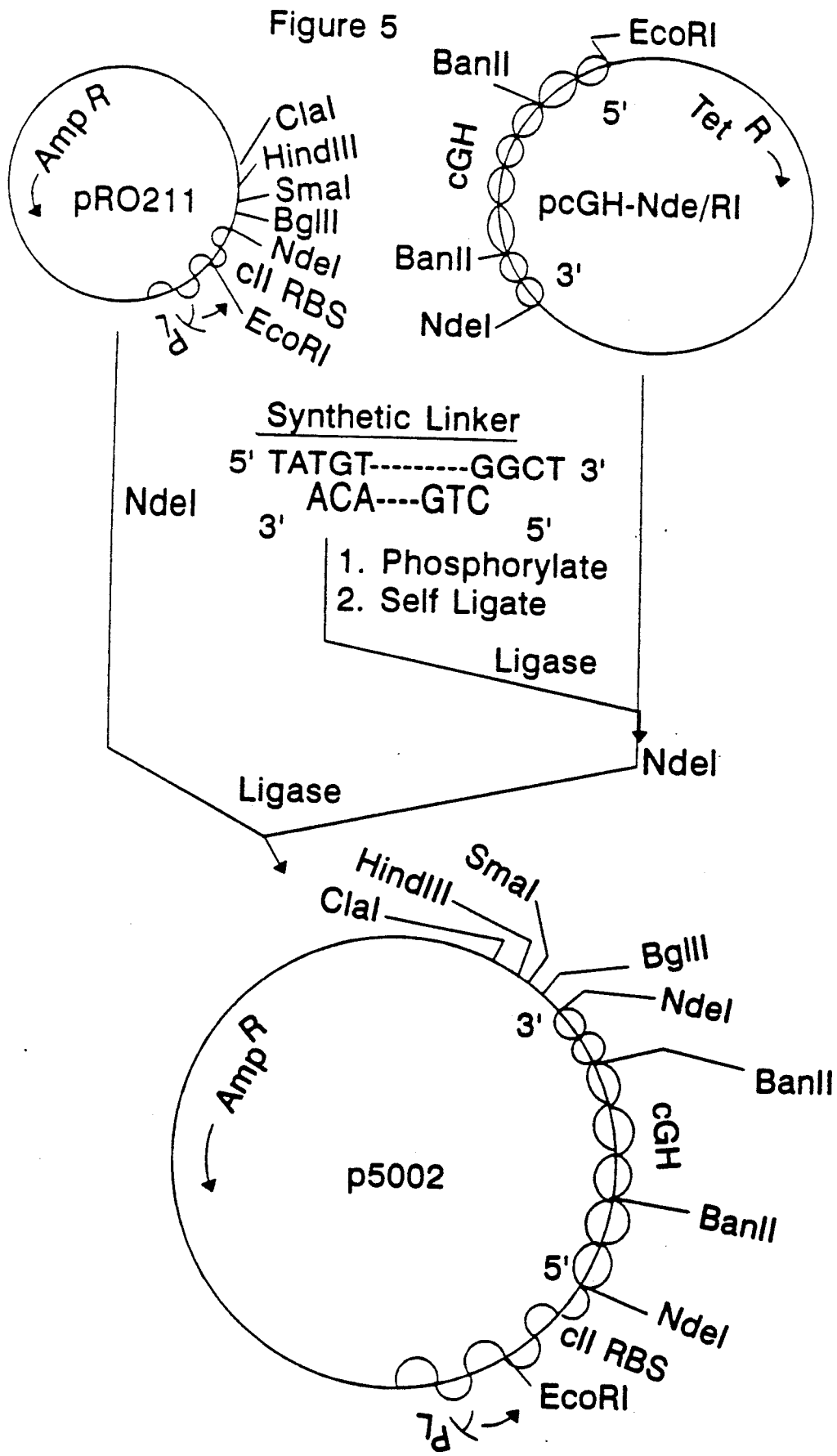
Figure 6:
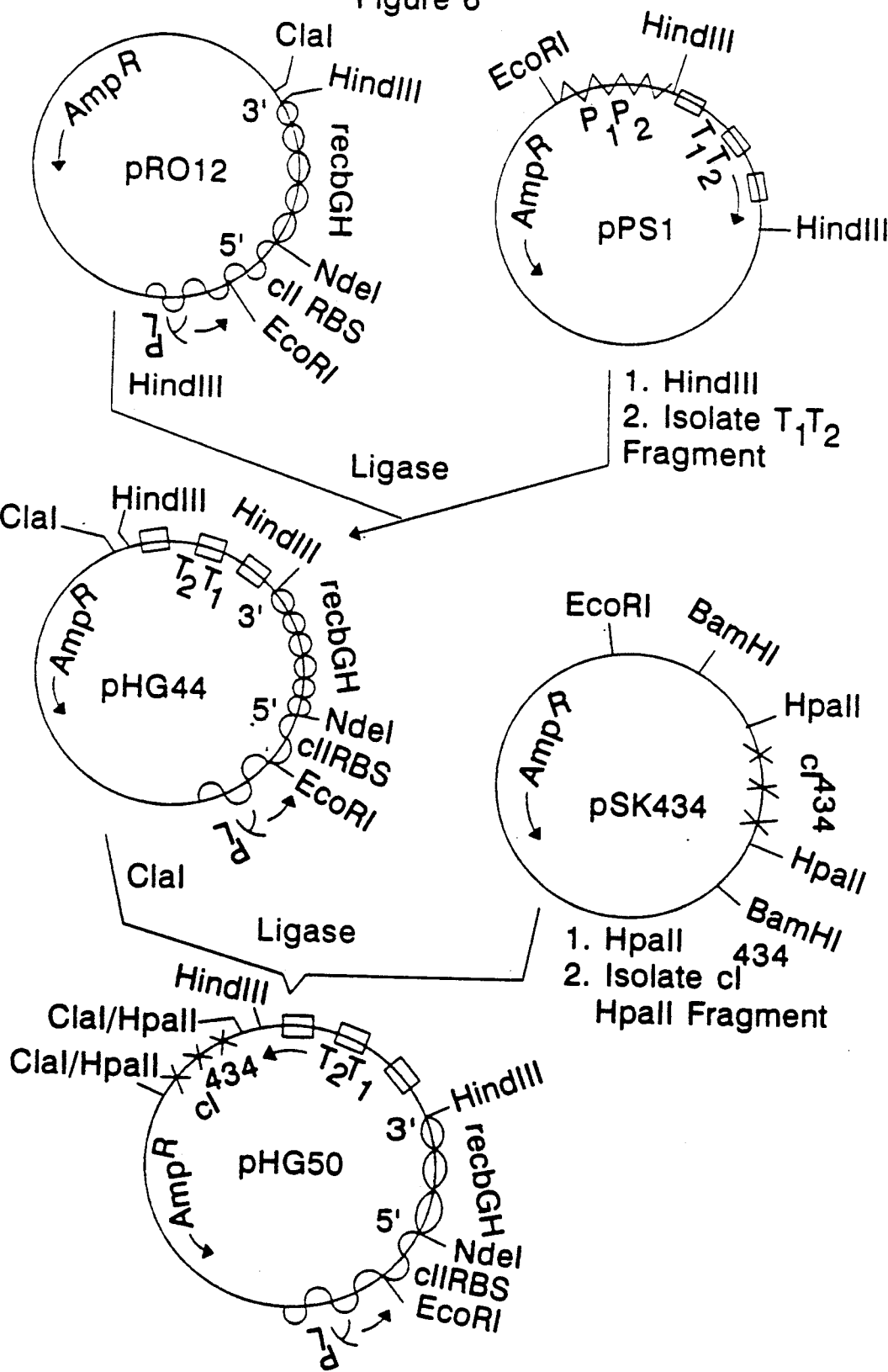
Figure 7:
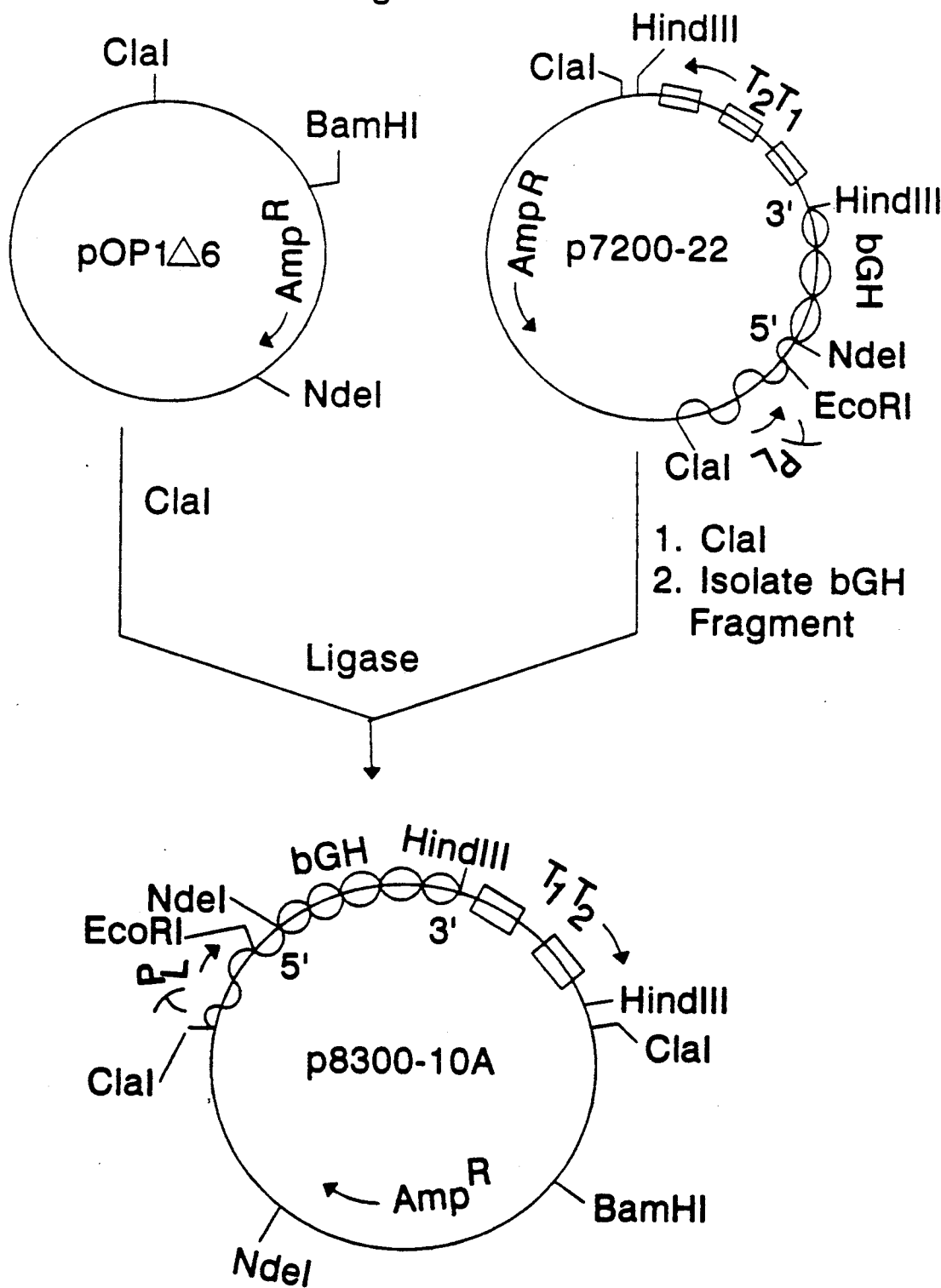
Figure 8:
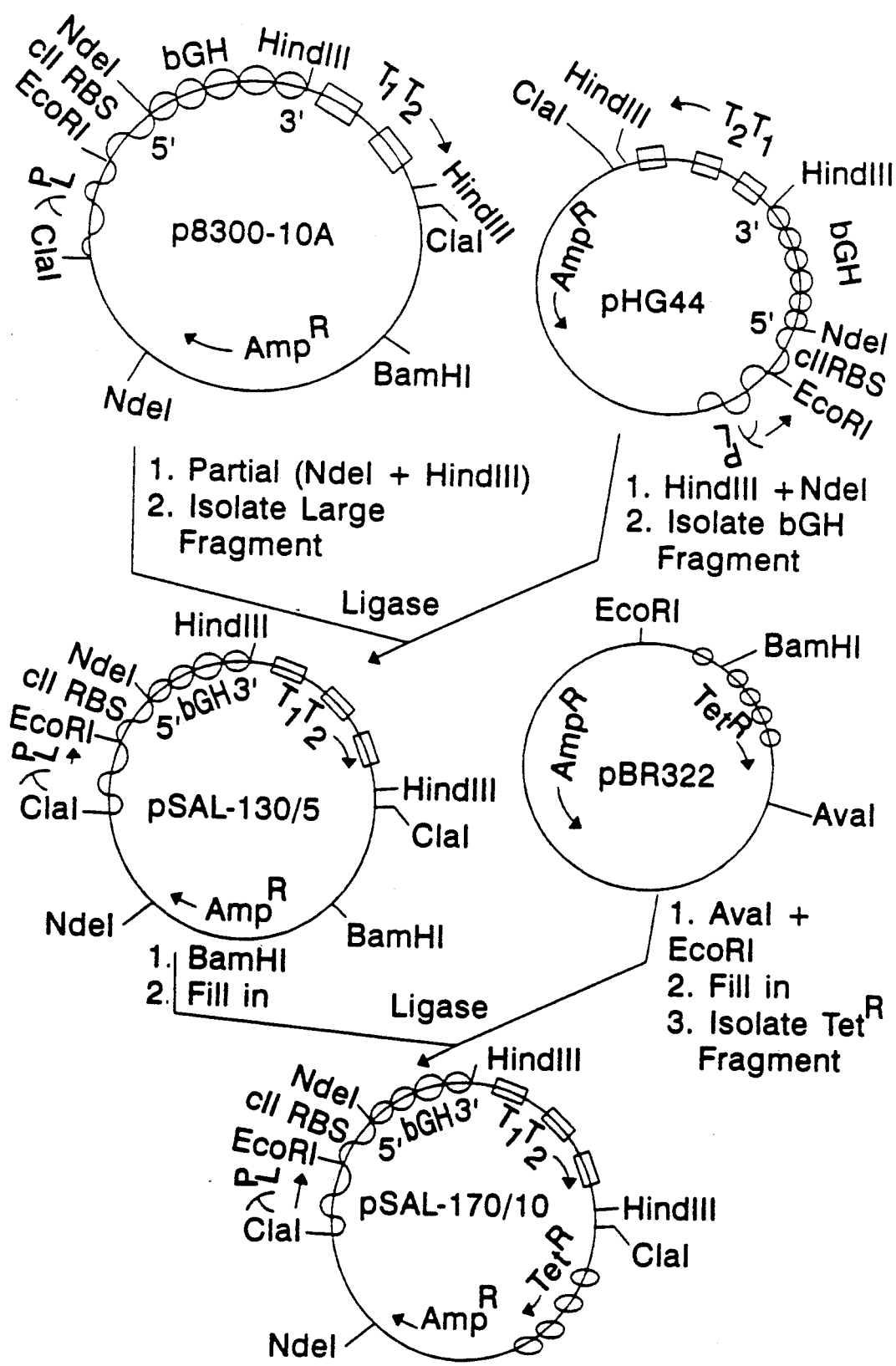
Figure 9:
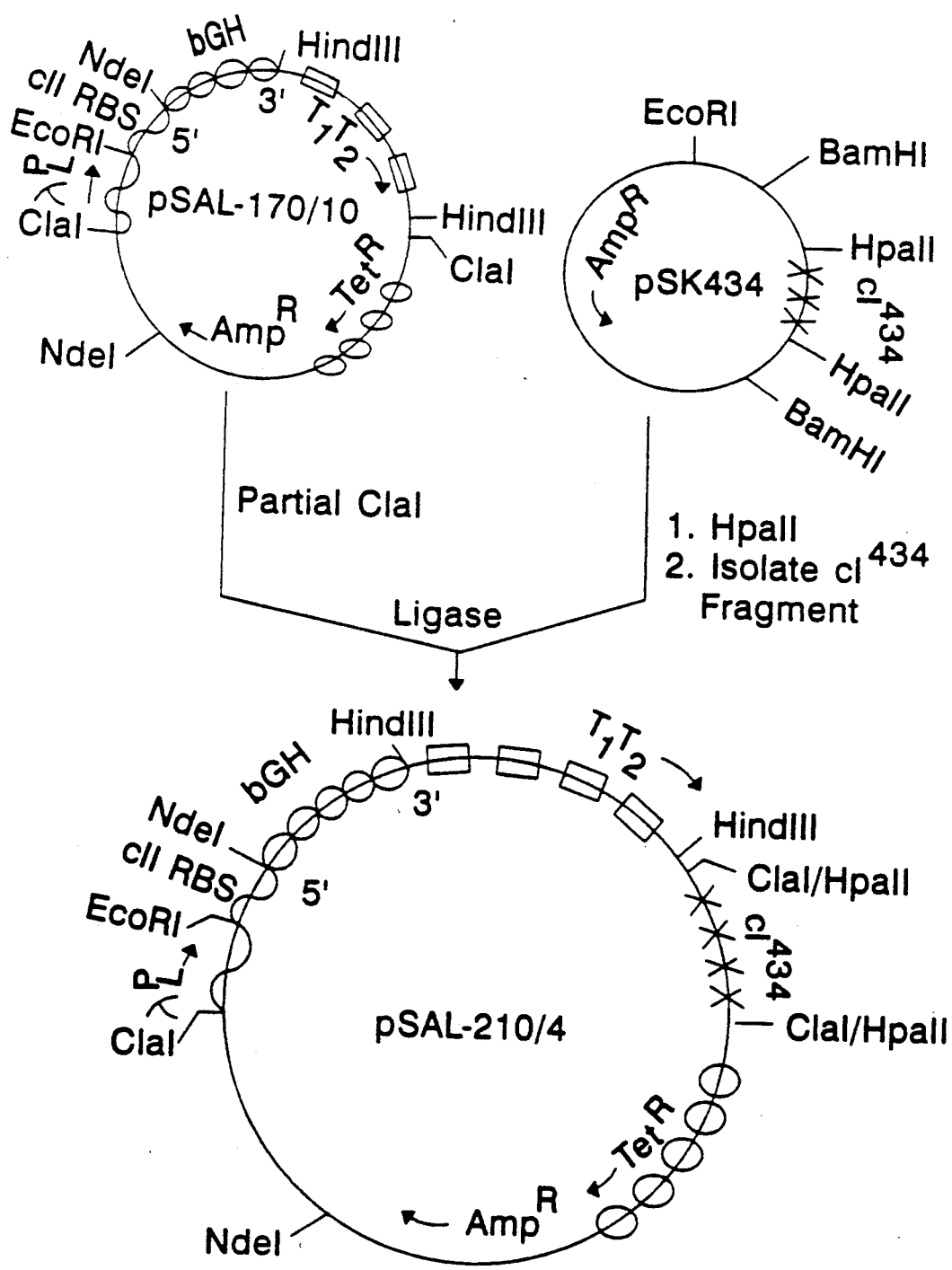
Figure 10:
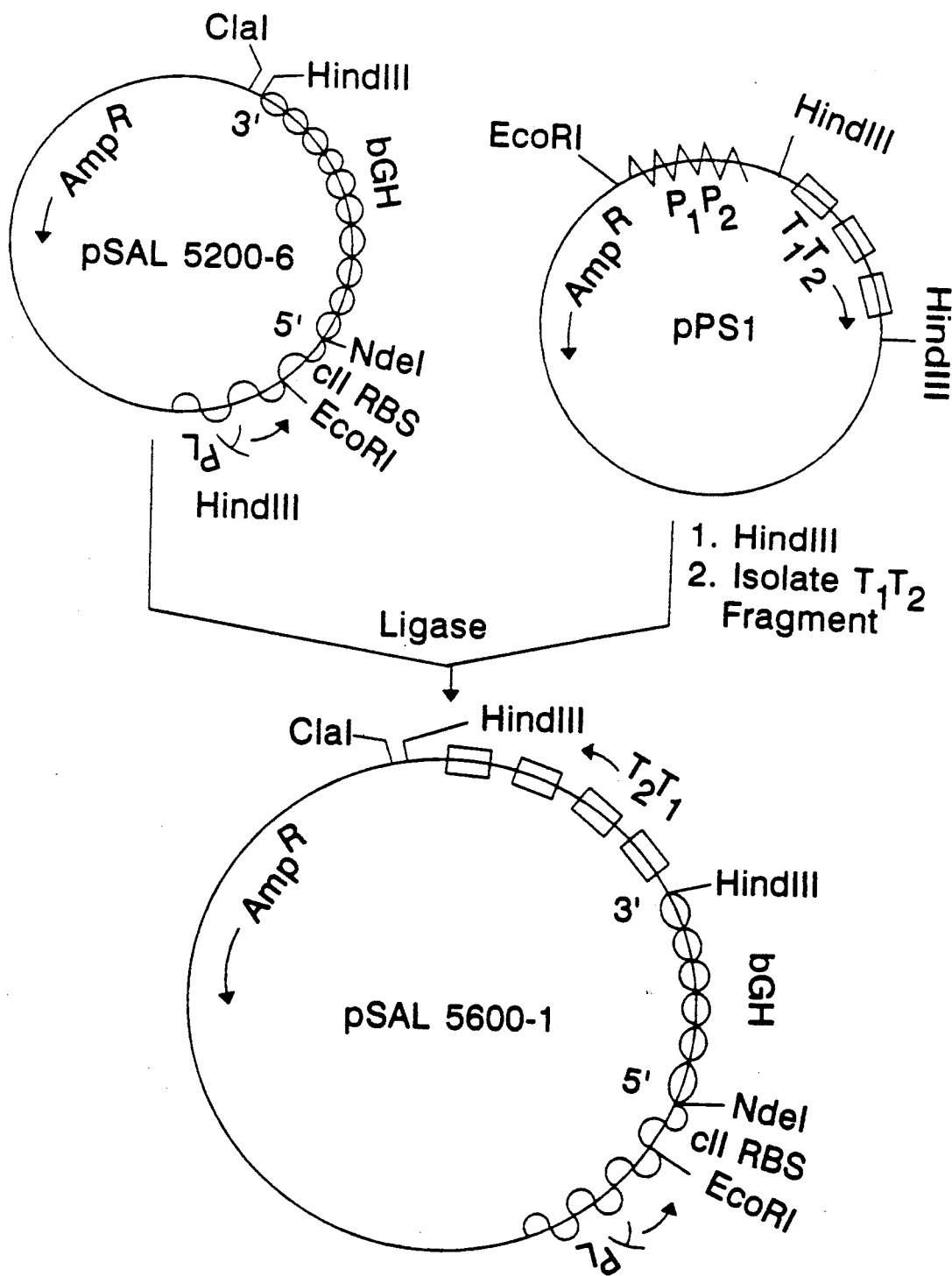
Figure 12:
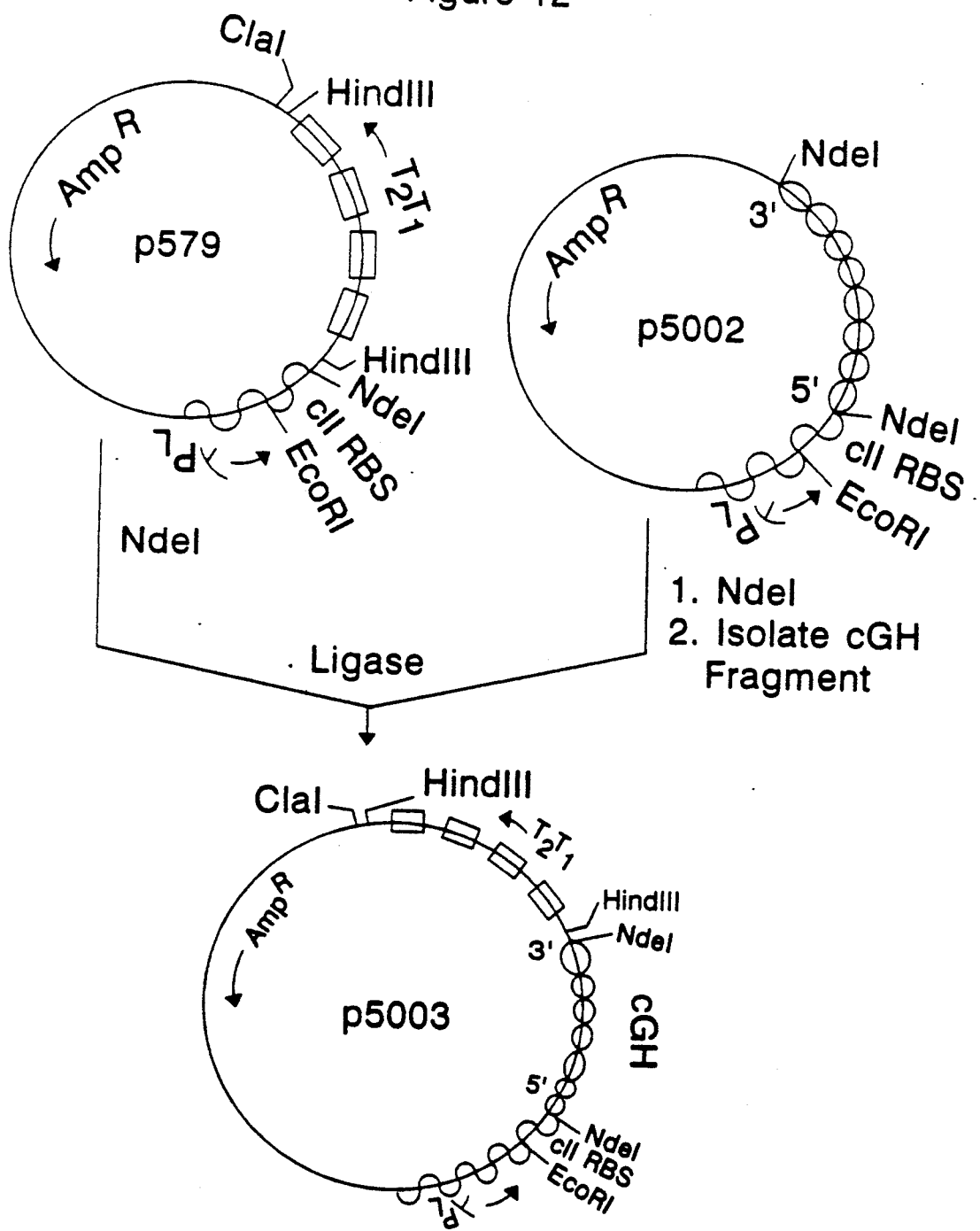

In another embodiment of the invention two chicken growth hormone fragments were isolated from NdeI-BamII digest of pcGH-NdeI/RI as shown in FIG. 5. The two cGH fragments were ligated to a phosphorylated synthetic linker which codes for the first 18 amino acids of the N-terminus of authentic cGH. The sequence of the linker was:

```
TATGTTCCCTGCCATGCCCCTCTCCAACCTGTTTGCCAACGCTGTGCTGAGGGCT
   ACAAGGGACGGTACGGGGAGAGGTTGGACAAACGGTTGCGACACGACTC.
```

The resulting fragment was then ligated to a NdeI digest of pRO211 to form the plasmid designated p5002 which has the restriction map shown in FIG. 5.

The vectors of this invention may also be engineered to produce human apolipoprotein E. The gene for human apoplipoprotein E (ApoE) may be isolated from plasmid pApoE-EX2 by NdeI digestion. pApoE-Ex2 has the restriction map shown in FIG. 18. It has been deposited in E. coli strain A1645 under ATCC Accession No. 39787.

The ApoE gene (cDNA) may be placed in various plasmids. Among the preferred embodiments is plasmid pTV-188 which has the restriction map shown in FIG.

18. pTV-188 was constructed by ligation of the ApoE gene isolated from pApoE-Ex2 to a StuI digest of plasmid pSODβ₁T₁₁. pTV-188 contains the Tet$^R$ fragment, the λP$_L$ promoter sequence, the β-lactamase promoter and Shine-Dalgarno sequence. This plasmid expresses an ApoE fused protein.

Figure 20:
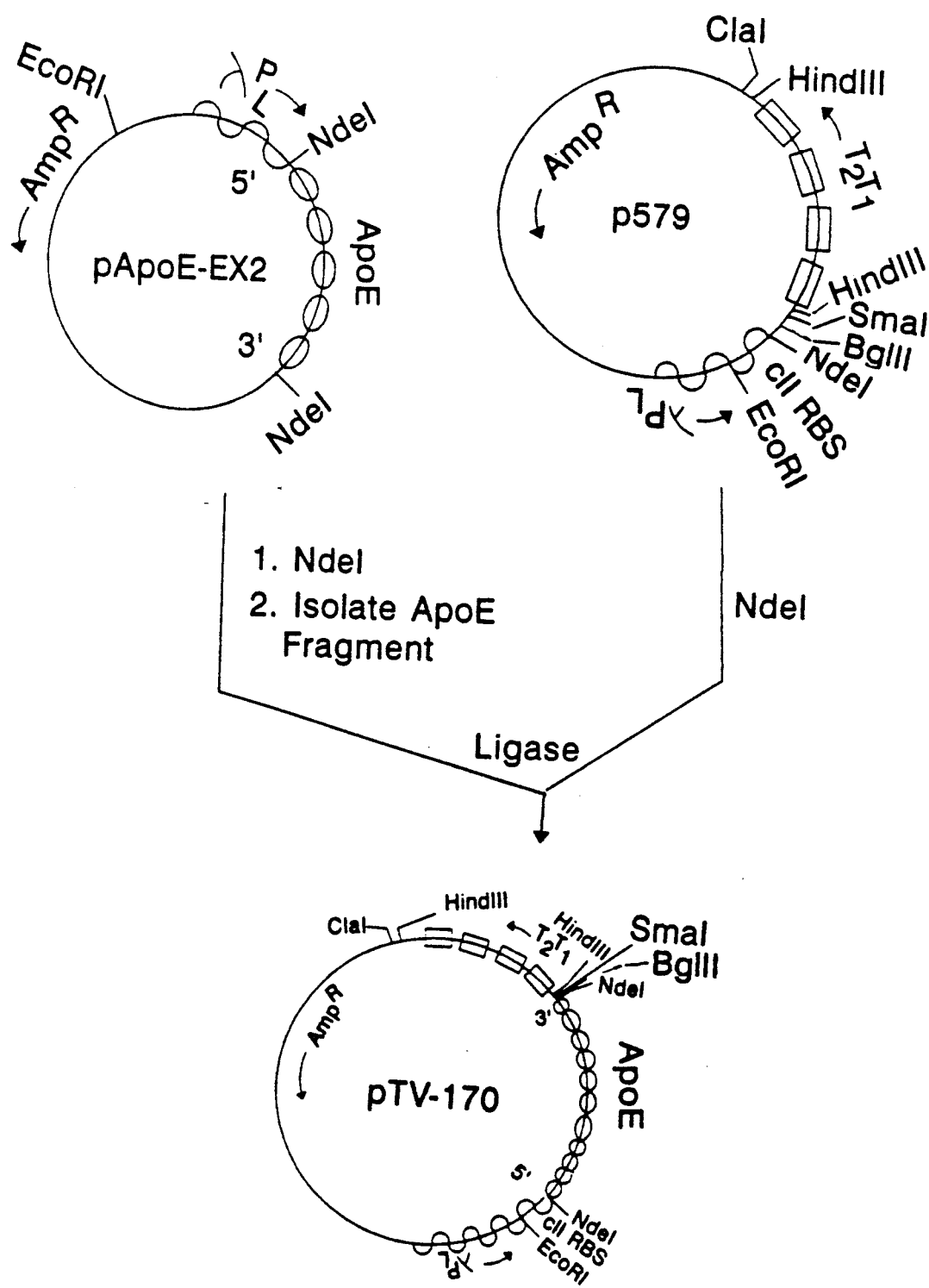
Figure 22:
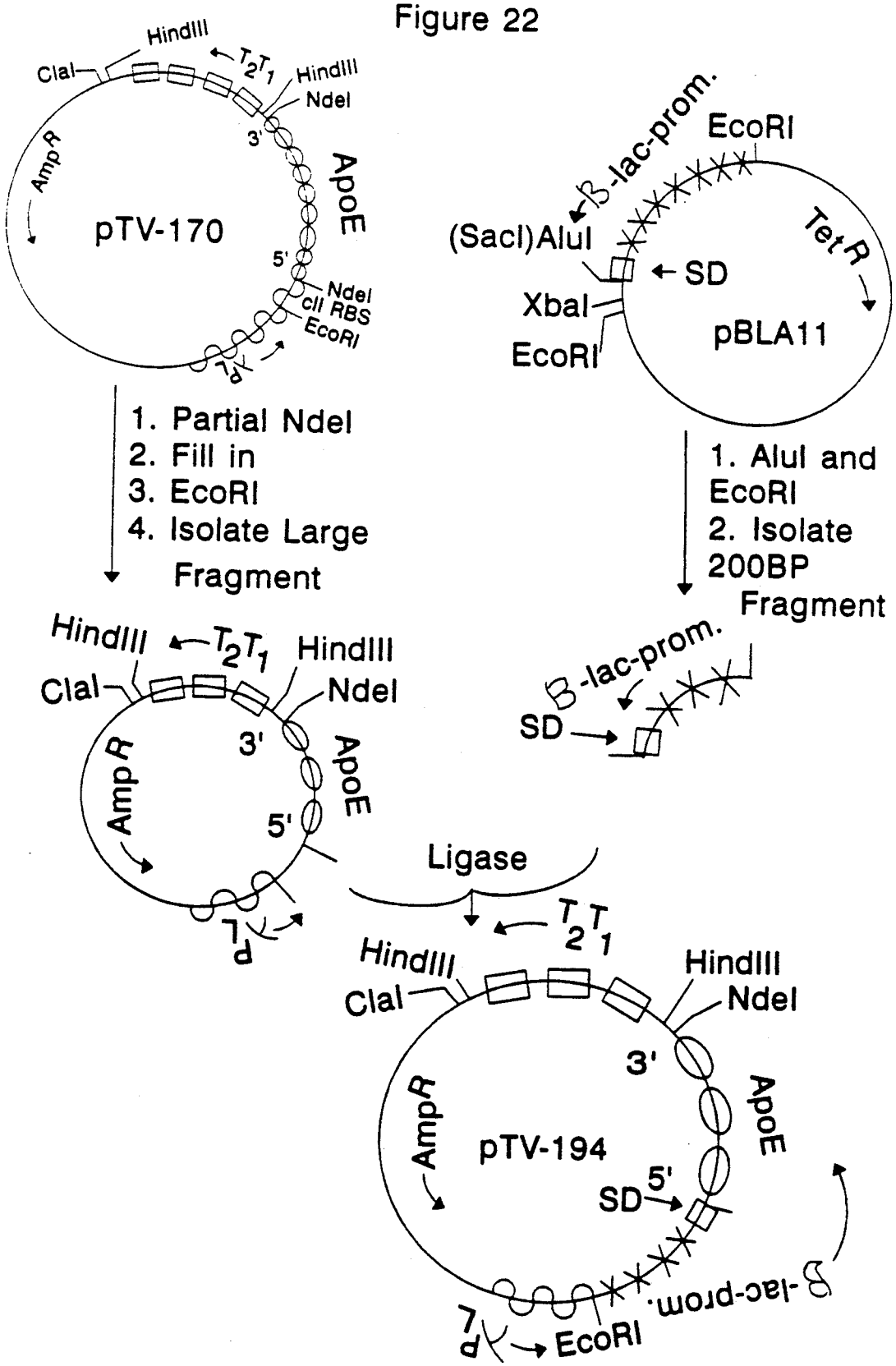
Figure 23:
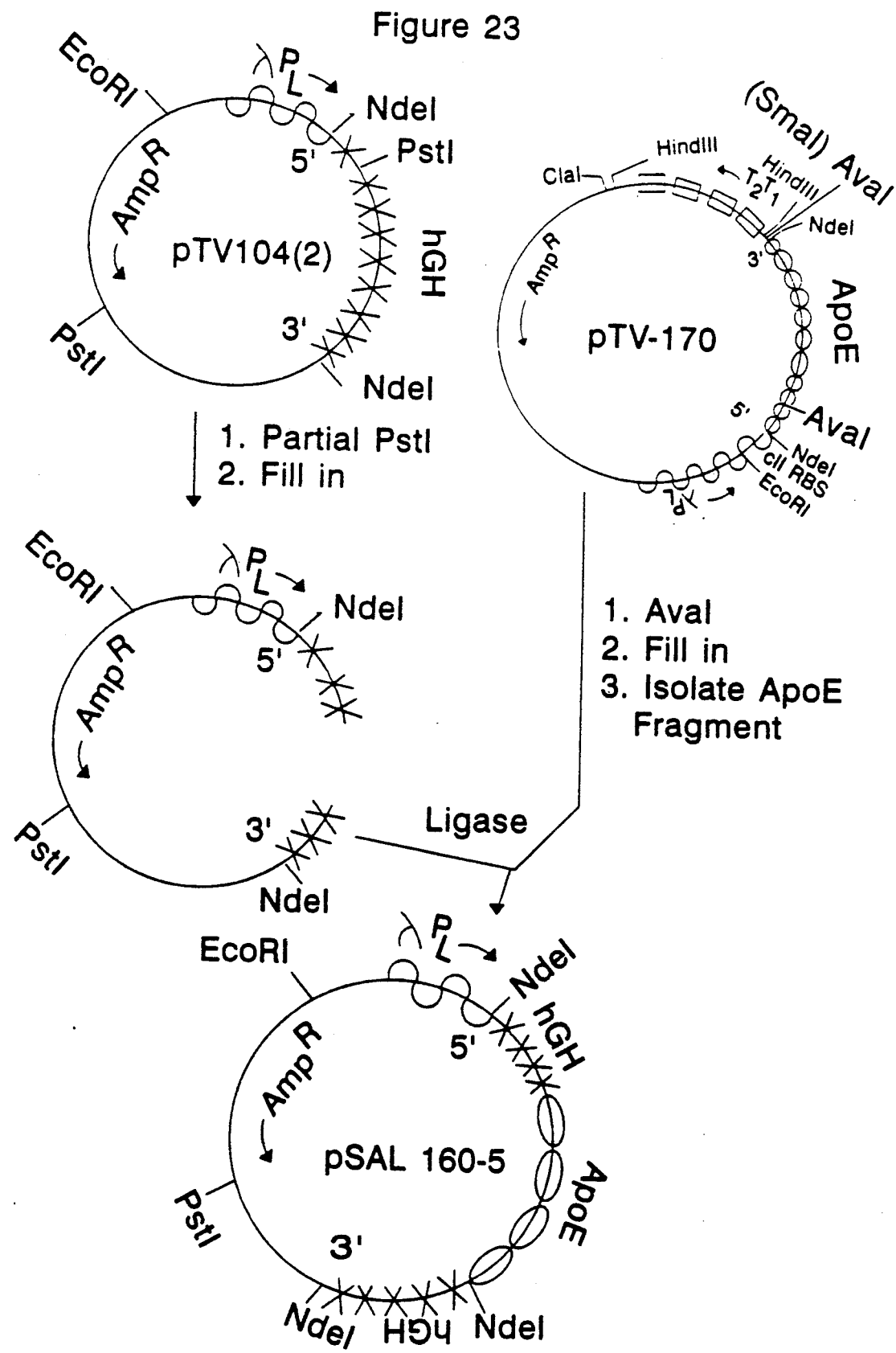
Figure 24:
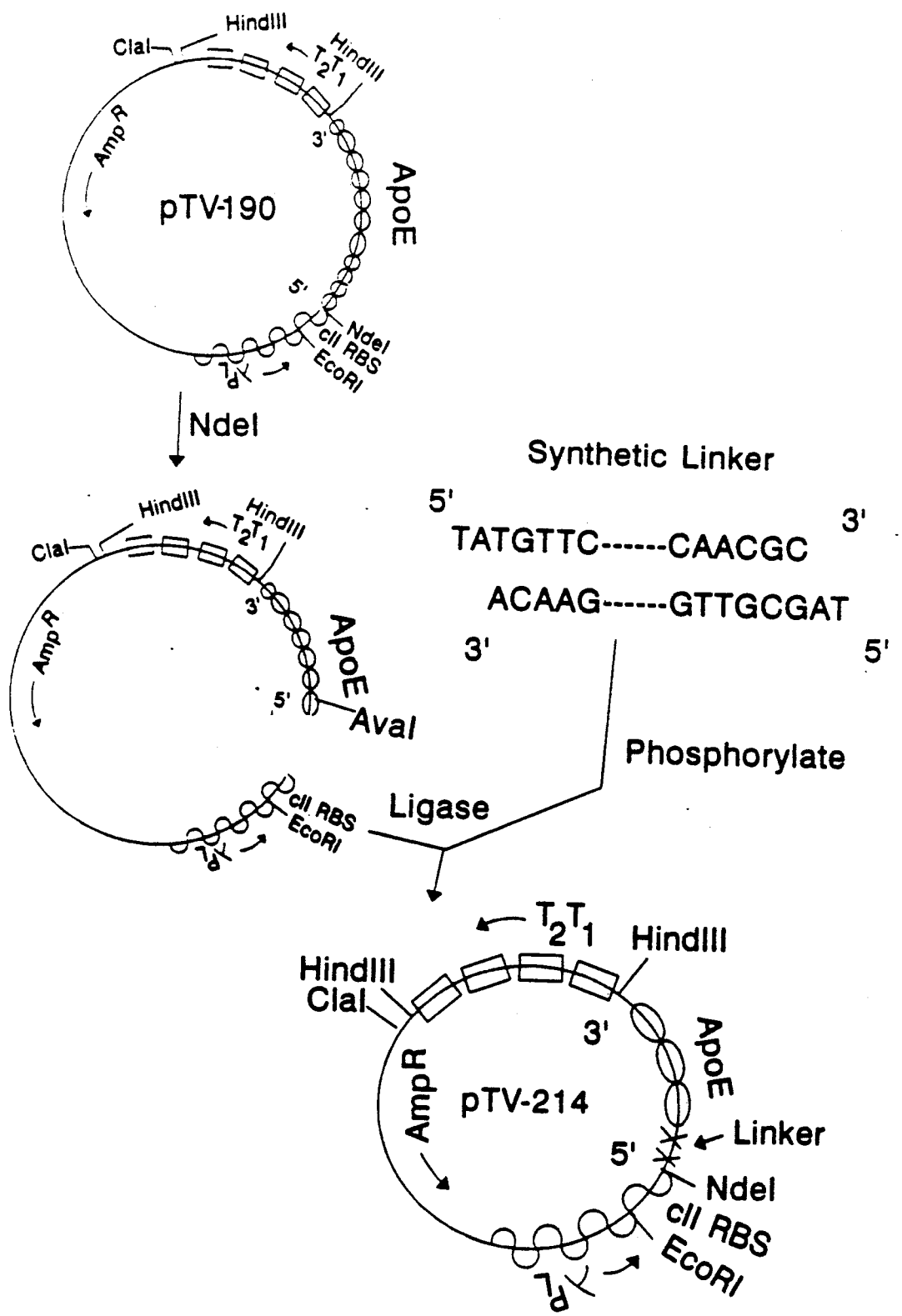

Another preferred embodiment of a plasmid which contains the ApoE gene is pSAL 160-5 which has the restriction map shown in FIG. 23. pSAL 160-5 was constructed from pTV 104(2) (ATCC No. 39384) and plasmid pTV-170, (see also FIG. 20). The ApoE gene was isolated from pTV-170 and inserted into pTV 104(2) at the PstI site within the human growth hormone gene sequence. The resulting plasmid pSAL 160-5 contains the Amp$^R$ fragment and the λ P$_L$ promoter sequence.

Using the same approach other plasmids may be prepared by replacing the gene encoding the desired polypeptide at the second restriction enzyme site of the plasmid.

Various host vector systems involve *E. coli* A1637, A1645, A2606, A2097, A1563, A4200, A4255 and A4048 and the plasmid described herein may be used to produce different polypeptides such as bovine, porcine, chicken and human growth hormones, human superoxide dismutase and human apolipoprotein E. To do so, the host vector system is grown under suitable conditions permitting production of polypeptide which is then recovered.

Suitable conditions involve growth of the host vector system for an appropriate period of time at about 42° C. Desirably, the period of growth at 42° C. is about 1 to 5 hours. Suitable media include casein hydrolysate.

By means of the preceding method a number of bGH, pGH, cGH, ApoE and SOD analogs have been prepared.

ApoE analogs have been prepared which have an amino acid sequence identical to that of natural ApoE except for variations at the N-terminus. Examples include the following:
1) amino acid methionine added to N-terminus of natural human apolipoprotein E;
2) natural human apolipoprotein E to the N-terminus of which is attached the 42 amino acid N-terminal sequence of human superoxide dismutase and then methionine; and
3) natural human apolipoprotein from which the 11 N-terminal amino acids have been deleted and replaced by the 45 amino acid N-terminal sequence of mature human growth hormone followed by methionine.

A pGH analog has been prepared in which the amino acid methionine is added to the N-terminus of natural porcine growth hormone.

A cGH analog has been prepared in which the amino acid methionine is added to the N-terminus of natural chicken growth hormone.

SOD analogs have been prepared which have an amino acid sequence identical to that of natural SOD except for variations at the N-terminus. Examples include the following:
1) natural human SOD which is non-acetylated;
2) natural human SOD which is non-acetylated and non-glycosylated;
3) natural human SOD which is non-acetylated and has the ser-met amino acid sequence attached to the amino terminus; and
4) natural human SOD which is non-acetylated and non-glycosylated and has the ser-met amino acid sequence attached to the amino terminus.

These SOD analogs or a mixture of same may be used to catalyze the dismutation or univalent reduction of the superoxide anion in the presence of proton to form hydrogen peroxide as shown in the following equation:

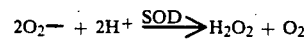

$$2O_2^- + 2H^+ \xrightarrow{SOD} H_2O_2 + O_2$$

Veterinary compositions may be prepared which contain effective amounts of one or more bGH, cGH or pGH analogs and a suitable carrier. Such carriers are well known to those of ordinary skill in the art. The analogs may be administered directly or in the form of a composition to a cow in order to increase milk or meat production, to a chicken in order to increase meat production or to a pig in order to increase meat production.

Pharmaceutical compositions may be prepared which contain effective amounts of one or more ApoE analogs and a suitable carrier. Such carriers are well known to those skilled in the art. The analogs may be administered directly or in the form of a composition to a human subject, e.g., to treat deficiencies in ApoE production by the subject, or to treat arteriosclerosis.

Veterinary and pharmaceutical compositions may also be prepared which contain effective amounts of SOD or one or more SOD analogs and a suitable carrier. Such carriers are well-known to those skilled in the art. The SOD or analog may be administered directly or in the form of a composition to the animal or human subject, e.g., to treat a subject afflicted by inflammations or to reduce injury to the subject by oxygen-free radicals on reperfusion following global ischemia or organ transplantation e.g., kidney transplantation. The SOD or analog may also be added directly or in the form of a composition to the perfusion medium of an isolated organ, e.g., to reduce injury to an isolated organ by oxygen-free radicals on perfusion after excision, thus prolonging the survival period of the organ, e.g., cornea. Additionally, the SOD or analog may be used to reduce spinal injury and for bronchial pulmonary dysplasia.

EXAMPLES

The examples which follow are set forth to aid in understanding the invention but are not intended to, and should not be construed to, limit its scope in any way. The examples do not include detailed descriptions for conventional methods employed in the construction of plasmids, the insertion of genes encoding polypeptides of interest into such plasmids or the introduction of the resulting plasmids into bacterial hosts. Such methods are well known to those of ordinary skill in the art and are described in numerous publications including by way of example the following:

T. Maniatis, E. F. Fritsch and J. Sambrook, *Molecular Cloning; A Laboratory Manual*, Cold Spring Harbor Laboratory, New York (1982).

*Methods in Enzymology*, vol. 65, "Nucleic Acids (Part 1)," edited by Lawrence Grossman and Kivie Moldave, Academic Press, New York (1980).

*Methods in Enzymology*, vol. 68, "Recombinant DNA," edited by Ray Wu, Academic Press, New York (1981).

*Methods in Enzymology*, vol. 100, "Recombinant DNA (Part B)," edited by Ray Wu, Lawrence Grossman and Kivie Moldave, Academic Press, New York (1983).

*Methods in Enzymology*, vol. 101, "Recombinant DNA (Part C)," edited by Ray Wu, Lawrence Grossman and Kivie Moldave, Academic Press, New York (1983).

*Principles of Gene Manipulation, An Introduction to Genetic Engineering*, 2nd Edition, edited by R. W. Old an S. B. Primrose, University of California Press (1981).

H. V. Bernard, et al., Gene (1979) 5, 59.

A. B. Oppenheim, et al., J. Mol. Biol. (1982) 158, 327.

E. Remaut, et al., Gene (1981) 15, 81.

EXAMPLE 1

Expression Vectors

As used herein the term "expression vector" refers to a group of plasmids useful for expressing desired genes in bacteria, particularly in *E. coli*. The desired gene may be inserted into the expression vector or alternatively, the promoters on the expression vector may be excised and placed in front of the desired gene.

pJH200 pJH200, shown in FIG. 2, is composed of a DNA inserted into the multicopy plasmid pBR322. The salient features of the $\lambda$DNA are that it contains the $\lambda P_L$ promoter, the leftward N utilization site (nut$_L$), an EcoRI restriction site, the t$_{RI}$ termination site, followed by the C$_{II}$ ribosomal binding site and an ATG initiation codon which is part of the NdeI restriction site. One hundred and sixteen (116) base pairs downstream of the NdeI restriction site are four unique restriction sites as shown in FIG. 2. The restriction sites enable facile insertion of the desired gene. The C$_{II}$ ribosomal binding site differs from the natural ribosomal binding site by a single point mutation.

pJH20 was constructed from pOG11 (A. Oppenheim, et al., J. Mol. Biol. (1982) 158; 327) and contains the $\lambda P_L$ promoter and the C$_{II}$ ribosomal binding site found in pOG11. However, 346 bp of $\lambda$DNA located between the $\lambda P_L$ promoter and the C$_{II}$ ribosomal binding site have been deleted, and an EcoRI restriction site has been introduced at the junction between these two elements. Also, a multi-restriction site linker was introduced "downstream" of the ribosome binding site. pJH200 has been deposited with the American Type Culture Collection under ATCC No. 39783.

pRO211 pRO211, shown in FIG. 2 and described in detail in the Description of Figures, was derived from pJH200 by eliminating one of the two NdeI restriction sites.

pJH200, pRO211 and derivatives thereof containing eucaryotic genes may be maintained in suitable *E. coli* hosts. The most important feature of a suitable host is that it provide the thermosensitive repressor cI857 and the anti-termination N protein. (M. E. Gottesman, et al., J. Mol. Biol. (1980) 140; 57-75).

pRO211 has numerous advantages over previously described expression vectors including:

1. extremely high levels of expression

The vector is capable of directing expression of foreign proteins in *E. coli* at levels as high as 35% of the total cellular protein.

2. replaceable ribosomal binding site pRO211 contains a unique EcoRI site which is located "upstream" of the ribosomal binding site, and an NdeI site located "downstream" of the ribosomal binding site. Thus, the ribosomal binding site is bounded by two unique restriction sites. This enables facile excision of the present ribosomal binding site (the $\lambda C_{II}$ ribosomal binding site) and substitution of virtually any other natural or synthetic ribosomal binding site without altering other features of the plasmid. This greatly facilitates optimal expression of desired polypeptides.

3. thermoinducible regulation of expression

The $\lambda P_L$ promoter is inactive when the C$_I$ repressor is bound to it. The cI857 repressor is thermosensitive, that is, it binds to the promoter at 30° C. but is inactivated at 42° C. Thus, by increasing the temperature of fermentation to 42° C. the host bacteria are induced to produce the desired protein.

The advantages of such a system include the following:

(a) A foreign protein which is toxic to *Escherichia coli* can be produced late in the fermentation process thus avoiding early cell death, (b) Overproduction of a protein may stabilize the protein and prevent proteolytic degradation. (Cheng, Y. E., et al., Gene (1981) 14, 121). Thus, "instantaneous" overproduction using a tightly regulated promoter such as $\lambda P_L$ may be preferable to continuous low level production.

4. simplified induction protocol

Protein production by the plasmids described in this patent application and in copending, coassigned U.S. patent application Ser. No. 514,188 is regulated by the thermosensitive cI857 repressor.

The induction protocol required by the plasmids described in the copending, coassigned application involved induction at 42° C. followed by growth at 38° C. In contrast, the optimal induction of protein synthesis when using the vectors pJH200, pRO211 or their plasmid derivatives involved induction at 42° c. followed by growth at the same temperature, i.e. 42° C. This eliminates the need to cool the fermentor.

5. copy number

The $\lambda P_L$ promoter in pJH200 and pRO211 is found on a plasmid with a copy number higher than the $\lambda$ transducing phage vectors which are present in *E. coli*. This increases expression levels.

6. ribosome binding site and initiation codon

This expression vector contains a strong procaryotic ribosomal binding site (RBS) as well as a translation initiation codon (ATG). Thus, any eucaryotic gene may be cloned without adding the initiation codon. Furthermore, the efficient RBS increases levels of expression. The ribosome binding site is the $\lambda C_{II}$ ribosomal binding site. The sequence of the ribosomal binding site is:

```
TAAGGAAGTACTTACAT
ATTCCTTCATGAATGTA
```

One base pair is different from the ribosomal binding site found in the wild type $\lambda$.

7. convenient restriction site

The expression vector has a unique NdeI restriction site which contains within the site the ATG initiation codon. This permits proper positioning of the desired gene. The unique NdeI site is found immediately after the ribosomal binding site.

8. convenient restriction sites for gene insertion

Located 116 base pairs downstream of the NdeI restriction site are 4 other unique restriction sites in the following order: BglII, SmaI, HindIII and ClaI. The multiplicity of unique restriction sites enables facile insertion of desired genes.

9. nut site

N protein, which is provided by the host, binds the Nut site on the expression vector and thereby prevent termination of transcription at the $t_{RI}$ site or premature transcription termination within the cloned gene.

Strains

Suitable hosts for the described vectors and plasmids are strains of E. coli suitable for transformation, including A1637, A2602, A1563, A1645 (C600 r⁻m⁺ gal⁺ thr⁻ leu⁻ lac⁻ bl (λcI847 ΔH1 ΔBamHI N⁺)) and A2097 (A1645 lac Δχ21 proC::Tn 10).

EXAMPLE 2

Animal Growth Hormones

I. pRO12

The construction of pRO12 is shown in FIG. 2 and described in the Description of the Figures. bGH cDNA from pAL500 whose construction is shown in FIG. 1, was manipulated prior to insertion into pRO211 to provide the correct reading frame and an NdeI restriction site.

pRO12 was introduced into Escherichia coli strain A1645 by transformation using methods known to those of ordinary skill in the art. This strain produces upon growth and induction an analog of bovine growth hormone (bGH) having the amino acid sequence met-asp-gln added to the N-terminus of the phenylalanine form of natural bGH. The amount of bGH analog produced by pRO12 was about 30–36% of the total protein produced by the bacteria as calculated by scanning Coomasie blue-stained SDS polyacrylamide gels (Table I).

II. pSAL 5200-6

Figure 3:
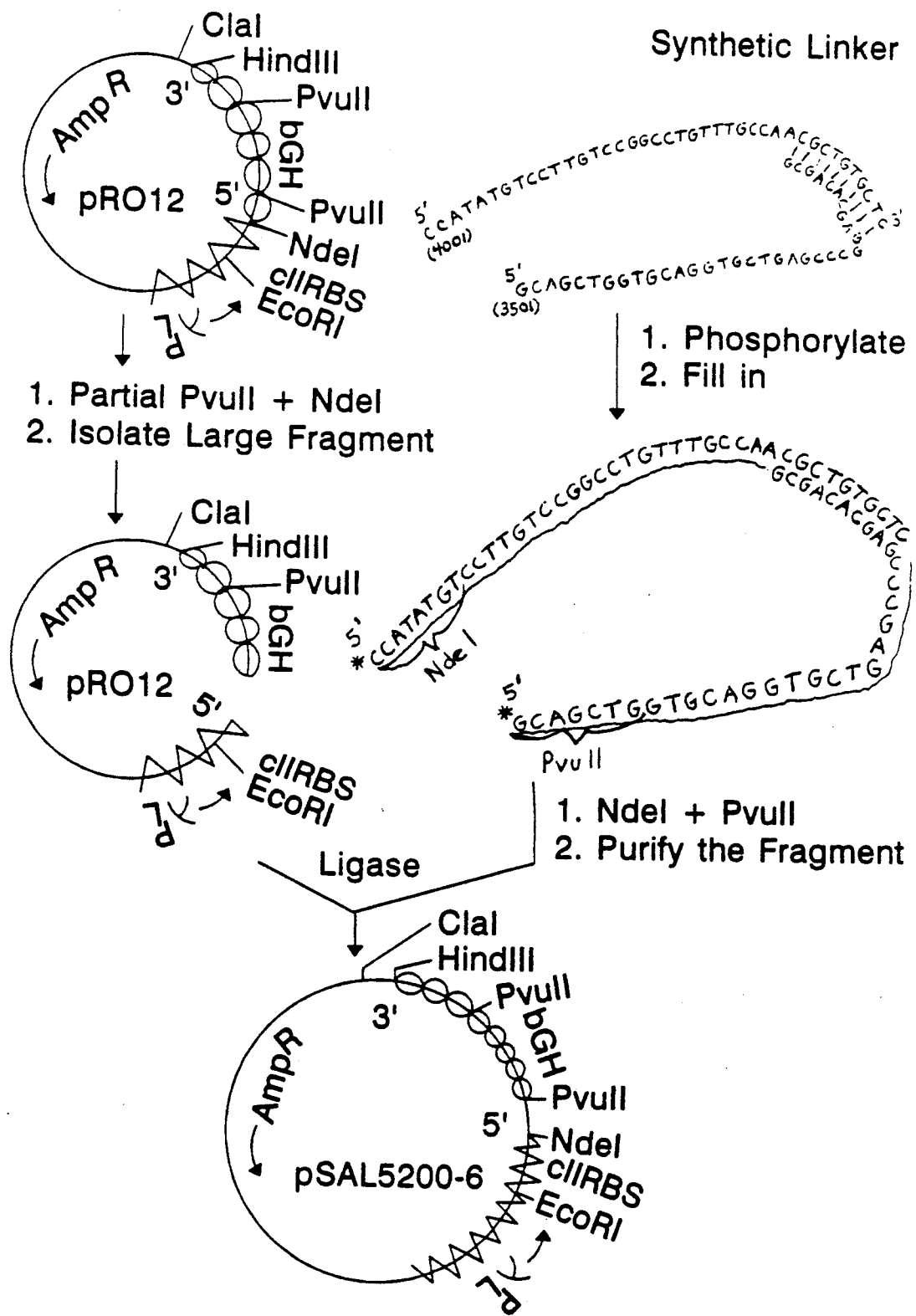

The construction of pSAL 5200-6 is shown in FIG. 3 and described in the Description of the Figures. The DNA sequence coding for met-phe bGH was obtained by restricting pRO12 with PvuII and NdeI and inserting a synthetic DNA fragment formed from two single-stranded synthetic oligonucleotides having 10 base pair overlapping segments.

pSAL 5200-6 was introduced into Escherichia coli strain A1645 by transformation using known methods. This strain produces upon growth and induction an analog of bGH having a methionine added to the amino terminus of phe bGH. The amount of the met-phe bGH analog produced by pSAL 5200-6 was about 18–20% of the total protein produced by the bacteria as calculated from scanning Coomasie-stained SDS polyacrylamide gels. The methods used to grow the strain, recover the bGH produced and purify the bGH are the same as those described hereinafter in Example 5 for bGH production from pRO12.

III. p3008

The construction of p3008 is shown in FIG. 4 and described in the Description of the Figures. p3008 has been deposited with the American Type Culture Collection under ATCC No. 39804. The DNA sequence coding for met-phe pGH (porcine growth hormone) was obtained by inserting pGH cDNA into pRO211.

p3008 was introduced into Escherichia coli strain A1645 by transformation using methods known to those of ordinary skill in the art. This strain produces upon growth and induction pGH having a methionine added to the amino terminus of phe pGH. The amount of the met-phe pGH analog produced by p3008 was about 18–20% of the total protein produced by the bacteria as calculated from scanning Coomasie-stained SDS polyacrylamide gels. The methods used to grow the strain, recover the pGH produced and purify the pGH are the same as those described hereinafter in Example 5 for bGH production from pRO12.

IV. p5002

The construction of p5002 is shown in FIG. 5 and described in the Description of the Figures. The DNA sequence coding for met-phe cGH (chicken growth hormone) was obtained by inserting cGH cDNA into pRO211 and completing the 5' end of the gene with synthetic oligonucleotide linkers.

p5002 was introduced into Escherichia coli strain A1645 by transformation using known methods. This strain produces upon growth and induction cGH having a methionine added to the amino terminus of phe cGH. The amount of the met-phe cGH analog produced by p5002 was about 18–20% of the total protein produced by the bacteria as calculated from scanning the Coomasie-stained SDS polyacrylamide gels. The methods used to grow the strain, recover cGH produced and purify the cGH are the same as those described hereinafter in Example 5 for bGH production from pRO12.

TABLE I[1]

| Plasmid | Host | % bGH[2] | Remarks |
| --- | --- | --- | --- |
| pRec ₹ | A1637 | 23 | Amp$^R$ |
| pRO11 | A1637 | 28 | Amp$^R$ |
| pRO12 | A1645 | 30–36 | Amp$^R$ |
| pHG44 | A2097 | 37–42 | Amp$^R$,T$_1$T$_2$ |
| pHG50 | A1645 | 37–42 | Amp$^R$,T$_1$T$_2$;cI$^{434}$ |
| pSAL-130/5 | A1645 | 39–44 | Amp$^R$;CHCN;T$_1$T$_2$ |
| pSAL-170/10 | A1645 | 40–46 | Tet$^R$;CHCN;T$_1$T$_2$ |

[1]The table summarizes the bGH expression levels of various plasmids derived from pRO211 and also of plasmids pRec ₹ and pRO11 both of which are described in copending, coassigned U.S. Pat. application Ser. No. 514,188, filed July 15, 1983.
[2]Amount of bGH produced as percentage of total bacterial protein.
ABBREVIATIONS
CHCN = Constitutive high copy number
Amp$^R$ = Ampicillin resistance
Tet$^R$ = Tetracycline resistance
T$_1$T$_2$ = Transcription termination sequences
cI$^{434}$ = Plasmid stabilization cI$^{434}$ system

EXAMPLE 3

Human Cu-Zn Superoxide Dismutase (SOD)

The starting point for Cu-Zn SOD cDNA modifications is the plasmid pS61-10 described in Leiman-Hurwitz, J., et al., PNAS (1982), 79: 2808. The SOD cDNA is also described in copending U.S. patent application Ser. No. 489,786, filed Apr. 29, 1983. The SOD cDNA was modified to introduced an NdeI restriction site at the 5' end of the gene and a HindIII restriction site at the 3' end of the gene. The resulting plasmid, pSOD NH-10, contains SOD cDNA bounded by unique restriction sites.

Modification of hSOD cDNA at 5'-End and Construction of pSODNH-10

Figure 31:
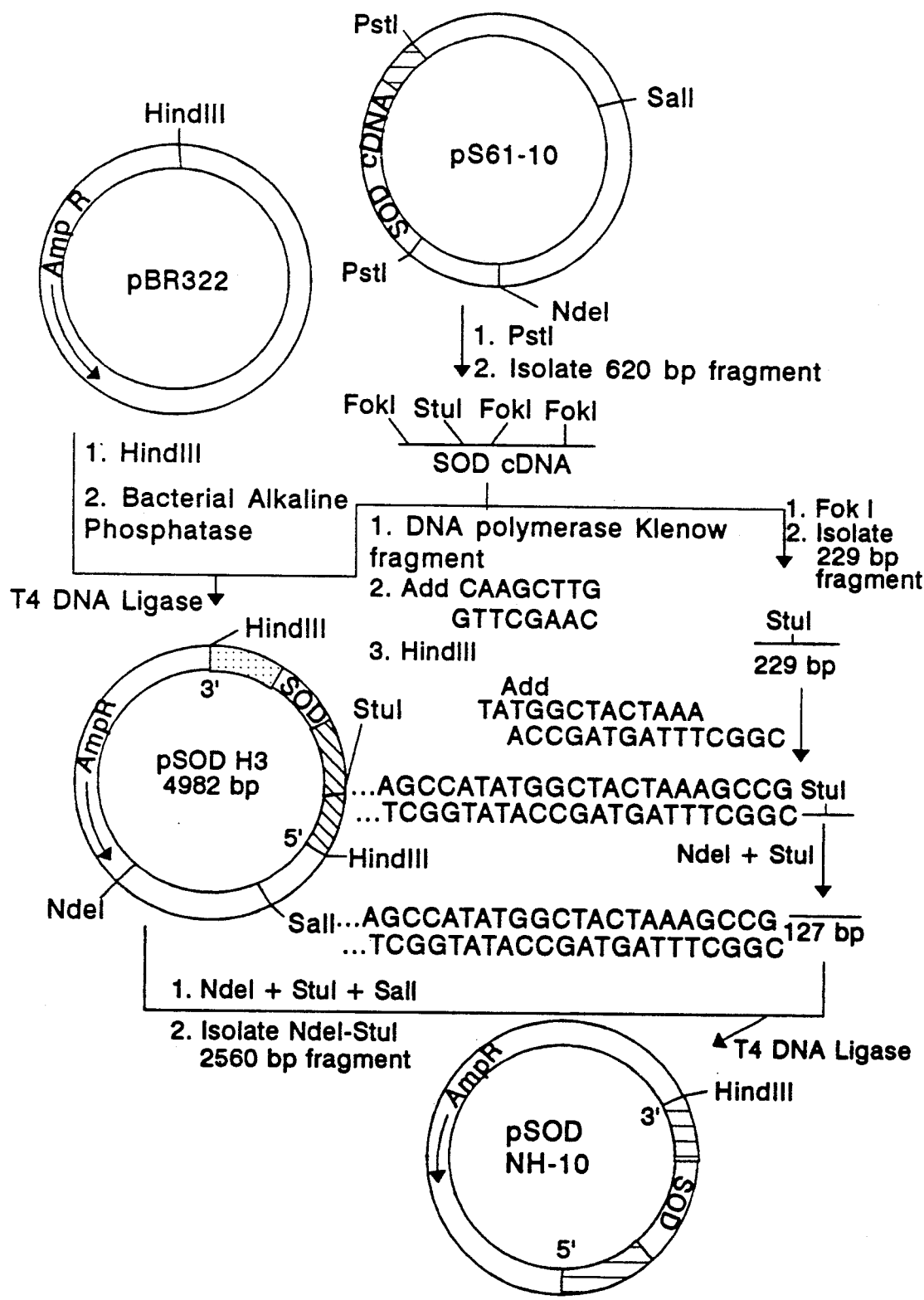

The modification of hSOD cDNA at the 5'-end and construction of pSODNH-10 is shown in FIG. 31 and described in the Description of the Figures.

Plasmid pS61-10 was digested with PstI and the small PstI-PstI 620 bp fragment containing hSOD DNA was isolated by electrophoresis on 1% agarose gel. The purified fragment was dissolved in 50 μl of TE buffer and separated into two equal aliquots. The first aliquot was treated with DNA polymerase (Klenow fragment) in the presence of all 4 dNTP's in order to obtain a blunt-ended fragment. The Klenow reaction was carried out at 16° C. for 30 minutes and the reaction was terminated by phenol-chloroform extraction and ethanol precipitation. The DNA fragment was dissolved in ligation buffer and was ligated to HindIII phosphorylated linkers with the sequence:

```
CAAGCTTG
GTTCGAAC
```

The reaction was terminated by heating at 70° C. for 5 minutes, and treated with HindIII (100 units). The fragment was then ligated to pBR322 DNA which was digested with HindIII (100 units). The fragment was then ligated to pBR322 DNA which was digested with HindIII and treated with bacterial alkaline phosphatase. The DNA ligation mixture was used to transform $E.$ $coli$ strain 1061 and $Amp^R$ clones were selected. These clones were screened by in situ filter hybridization to a nicked translated radioactive probe containing the hSOD DNA sequences. One of the positive clones, pSODH3, was analyzed by restriction mapping.

The second aliquot of the 620 bp PstI-PstI fragment was digested with FokI and the 229 bp FokI-FokI fragment was purified by electrophoresis on a 1% agarose gel redissolved in ligation buffer and ligated to a synthetic phosphorylated DNA linker with the sequence:

```
 TATGGCTACTAAA
 ACCGATGATTTCGGC
```

The reaction was stopped by heating at 70° C. for 5 minutes and then the DNA was digested with NdeI and StuI. The newly formed 127 bp fragment with the synthetic linkers was ligated with T4 DNA ligase to the large DNA fragment of plasmid pSODH3 which was obtained by digestion with NdeI, StuI and SalI: NdeI-StuI fragment of about 2560 bp was isolated. The DNA ligation mixture was used to transform $E.$ $coli$ strain 1061 and $Amp^R$ transformants were selected. The clones were screened for the right plasmid construction by NdeI and HindIII double digestion. One of these clones (pSOD NH-10) was sequenced and has been used for the expression of the human CuZn hSOD.

I. pSODα2

The construction of pSODα2 is shown in FIG. 13 and described in the Description of the Figures. pSODα2 has been deposited with the American Type Culture Collection under ATCC No. 39786. To construct pSODα2, the $\lambda P_L$ promoter, the $Nut_L$ and the $C_{II}$ ribosomal binding site were excised from the expression vector pJH200 and placed in front of the SOD gene of plasmid pSOD NH-10. Then, the fragment containing both the promoter, the RBS and the SOD gene was inserted into the vector pBRM (Hartman, J. R., et al., PNAS 79: 233-237 (1982). pBRM has been deposited with the American Type Culture Collection under ATCC No. 37283.

pSODα2 was introduced into $Escherichia$ $coli$ strain A2097 by transformation using known methods. The clones obtained produce upon growth and induction an SOD analog protein. The amount of SOD analog produced by pSODα2 was about 0.1-0.3% of the total protein produced by the bacteria as calculated from scanning of Coomasie-stained SDS polyacrylamide gels (Table II). The SOD analog produced is probably identical to that produced by pSODβ1 described in the following paragraph.

II. pSODβ1

The construction of pSODβ1 is shown in FIG. 14 and described in the Description of the Figures. To construct pSODβ1, the $C_{II}$ RBS of pSODα2 was replaced with the β-lactamase promoter and RBS derived from pBLA11. pBLA11 has been deposited with the American Type Culture Collection under ATCC No. 39788. pBLA11 contains the promoter and ribosomal binding site of the β-lactamase gene found in pBR322 between coordinates 4157 and 4353. An EcoRI linker was added upstream of the promoter and a multi-restriction site linker was added immediately after the initiation codon ATG. Thus, the sequence of the coding strand beginning with the initiation codon is ATGAGCTCTAGAATTC.

pSODβ1 was introduced into $Escherichia$ $coli$ strain A1645 by transformation using known methods. The clones obtained produce upon growth and induction an SOD analog. The human Cu-Zn SOD analog produced differs from natural human Cu-Zn SOD in that the amino terminus alanine is not acetylated, as demonstrated by amino acid sequencing stoichiometry while the natural human SOD is acetylated at the amino terminus alanine (Hartz, J. W. and Deutsch, H. F., J. Biol. Chem. (1972) 234:7043-7050; Jabusch, J. R., et al., Biochemistry (1980) 19:2310-2316; Barra, et al., FEBS Letters (1980) 120:53 and Oberley, L. W., $Superoxide$ $Dismutase$, Vol. I, (1982), CRC Press, Florida, p. 32-33.). Furthermore, the natural human SOD is glycosylated (Huber, W., U.S. Pat. No. 3,579,495, issued May 18, 1971) while bacterial-produced human SOD is almost certainly not glycosylated, because $Escherichia$ $coli$ does not glycosylate proteins which it produces. The amino acid sequence of the bacterial-produced SOD analog is identical to that of mature human SOD and does not contain a methionine residue at its N-terminus.

The amount of SOD produced by pSODβ1 was about 3-8% of the total protein produced by the bacteria as calculated from scanning of Coomasie-stained SDS polyacrylamide gels (Table II). The methods used to grow the strain, recover the SOD produced and purify the SOD are the same as those described hereinafter in Example 7 for pSOD β1T11.

III. pSOD$\beta_1$T$_{11}$

The construction of pSOD$\beta_1$T$_{11}$ is shown in FIG. 15 and described in the Description of the Figures. The gene coding for ampicillin resistance of pSOD$\alpha$1 was replaced with the gene coding for tetracycline resistance derived from pBR322. pSOD$\beta_1$T$_{11}$ has been deposited with the American Type Culture Collection and assigned ATCC Accession No. 67177. The amount of SOD analog produced by pSOD $\beta_1$T$_{11}$ was about 8–13% of the total protein produced by the bacteria as calculated from scanning of Coomasie-stained SDS polyacrylamide gels (Table II). The SOD produced by pSOD$\beta_1$T$_{11}$ is a mixture of SOD analogs. More than about 93% by weight of the SOD produced by pSOD$\beta_1$T$_{11}$ is the non-acetylated form of natural human superoxide dismutase having an amino acid identical to that of natural human CuZn superoxide dismutase and less than 7% by weight is the non-acetylated form of natural human superoxide dismutase having an amino acid sequence identical to that of natural human CuZn superoxide dismutase and having the amino acid sequence ser-met at the amino terminus. As used throughout this specification, the term SOD analog produced by pSOD$\beta_1$T$_{11}$ means a mixture of these SOD analogs.

IV. pSOD$\beta_1$-BA2

The construction of pSOD$\beta_1$-BA2 is shown in FIG. 17 and described in the Description of the Figures. The C$_{II}$ ribosomal binding site of pSOD$\alpha$13 was replaced by a synthetic DNA fragment with the sequence:

```
AATTCAATAATATTGAAAAAGGAAGAG
   GTTATTATAACTTTTTCCTTCTCAT
``` which is similar to the sequence of the natural $\beta$-lactamase RBS. pSOD $\beta_1$-BA2 was introduced into *Escherichia coli* strain A1645 by transformation using methods known to those of ordinary skill in the art. The clones obtained produce upon growth and induction an analog of human SOD. The amount of SOD produced by pSOD$\beta_1$-BA2 was about 2–4% of the total protein produced by the bacteria as calculated from scanning of Coomasie-stained SDS polyacrylamide gel (Table II). The SOD analog produced is identical to that produced by pSOD$\beta$1.

TABLE II

| Plasmid | RBS | Host | % SOD[3] | Remarks |
|---|---|---|---|---|
| pSOD$\alpha$2 | C$_{II}$ | A2097 | 0.1–0.3 | Amp$^R$ |
| pSOD$\beta_1$ | BLA[1] | A1645 | 3–8 | Amp$^R$ |
| pSOD$\beta_1$T$_{11}$ | BLA[1] | A1645 | 8–13 | Tet$^R$ |
| pSOD$\beta_1$TT-1 | BLA[1] | A1645 | 10–15 | Tet$^R$;T$_1$T$_2$ |
| pSOD$\beta_1$-BA2 | BLA[2] | A1645 | 2–4 | Amp$^R$ |

[1] Promoter and ribomosal binding site of $\beta$-lactamase gene.
[2] Synthetic ribosomal binding site corresponding to that of the $\beta$-lactamase gene.
[3] Amount of SOD analog produced expressed as percentage of total bacterial protein.

ABBREVIATIONS
Amp$^R$ = Ampicillin resistance
Tet$^R$ = Tetracycline resistance
T$_1$T$_2$ = Transcription termination sequences

EXAMPLE 4

Human Apolipoprotein E (ApoE3)

The starting point for ApoE3 cDNA modifications was the plasmid pNB178 provided by Dr. John Taylor of the Gladstone Foundation, San Francisco, Calif. This plasmid contains a full length cDNA copy of the human ApoE3 gene. The cDNA in pNB178 was modified to remove noncoding DNA at the 5' end of the gene and to add NdeI restriction sites at both ends of the gene. This ApoE3 cDNA fragment was inserted into the vector pND5 (described in copending, coassigned U.S. patent application Ser. No. 514,188, filed Jul. 15, 1983). The resulting plasmid, pApoE-Ex2, shown in FIG. 18, has been deposited with the American Type Culture Collection under ATCC No. 39787.

I. pTV-188

Figure 18:
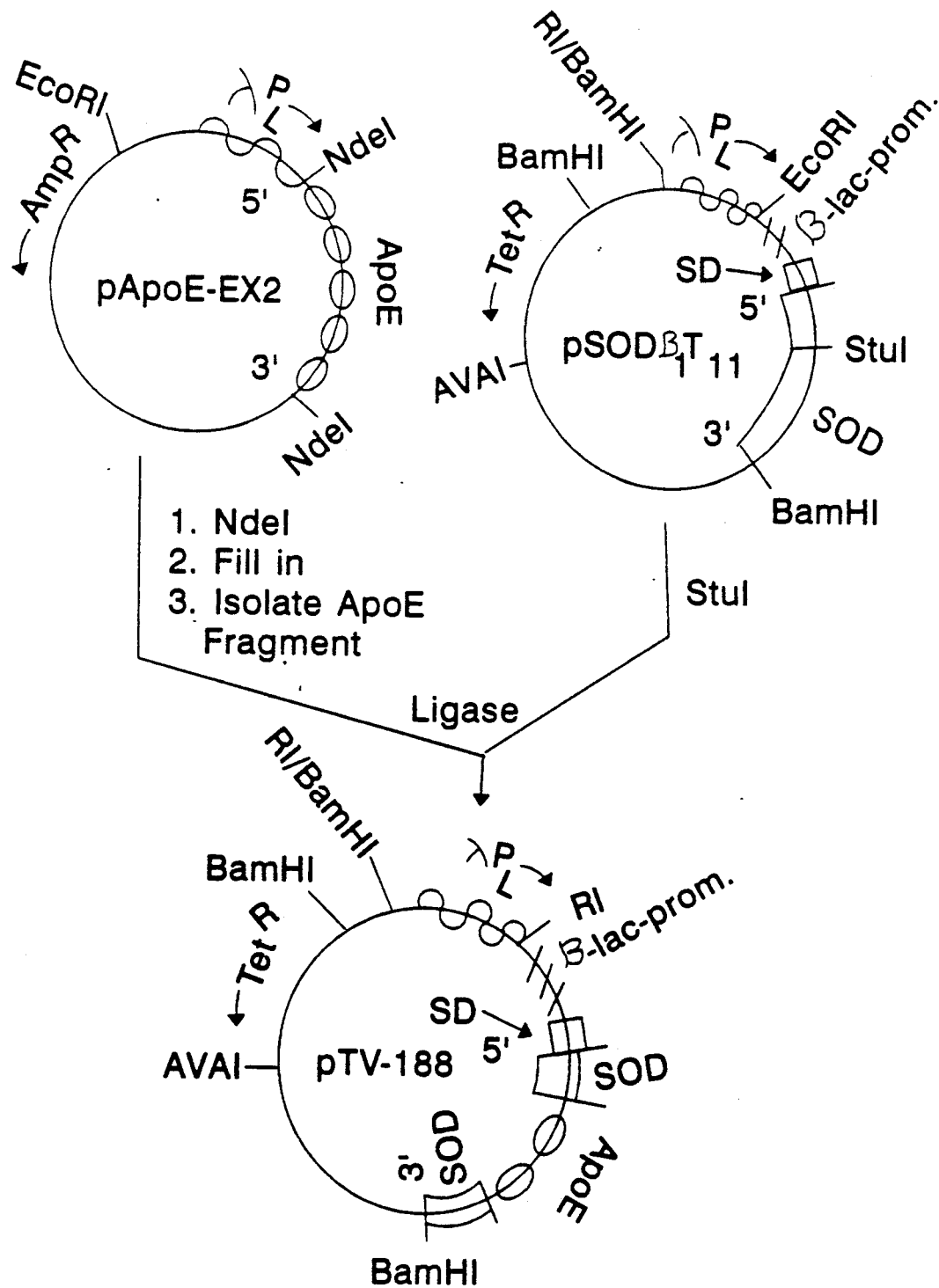

The construction of pTV-188 is shown in FIG. 18 and described in the Description of the Figures. The plasmid pTV-188 was obtained by insertion of the NdeI-NdeI filled-in, ApoE3 fragment into the unique blunt end Stu I site of pSOD$\beta_1$T$_{11}$ (shown in FIG. 14 and described in the Description of the Figures.)

pTV-188 was introduced into *Escherichia coli* strain A1645 by transformation using methods known to those of ordinary skill in the art. The clones obtained produce upon growth and induction an analog of human ApoE3 having 42 amino acids of the N-terminal sequence of human superoxide dismutase attached to the N-terminus of authentic human ApoE3 followed by methionine at the N-terminus of the analog. The ApoE3 analog produced was about 10% of the total protein produced by the bacteria as calculated by scanning Coomasie-stained SDS polyacrylamide gels. The method used to grow the strain is the same as that described in Example 5 for bGH production from pRO12 except that 12.5 mg/liter tetracycline is used instead of ampicillin.

II. pSAL 160-5

The construction of pSAL 160-5 is shown in FIG. 23 and described in the Description of the Figures. The plasmid pSAL 160-5 was obtained by insertion of the AvaI-AvaI ApoE3 gene fragment from pTV-170 (see FIG. 20).

pSAL 160-5 was introduced into *Escherichia coli* strain A1645 by transformation using methods known to those of ordinary skill in the art. The clones obtained produce upon growth and induction and analog of ApoE3 which contains at its amino terminus methionine and then 45 amino acids from the N-terminus of human growth hormone fused to ApoE3 from which the 11 N-terminal amino acids have been deleted. The amount of ApoE3 analog produced by pSAL 160-5 was about 5% of the total protein produced by the bacteria as calculated by scanning Coomasie-stained SDS polyacrylamids gels. The methods used to grow the strain is the same as that described in Example 5 for bGH production from pRO12.

EXAMPLE 5

Growth of pRO12

I. Stock Cultures

Stock cultures of pRO12 were grown on casein medium (see Inoculum), then diluted two-fold with freezing medium and stored at −80° C. Freezing medium contains per 500 ml:

| | |
|---|---|
| K$_2$HPO$_4$ | 6.3 gr |
| KH$_2$PO$_4$ | 1.8 gr. |
| Na Citrate | 0.45 gr |
| MgSO$_4$.7H$_2$O | 0.09 gr |
| (NH$_4$)$_2$SO$_4$ | 0.9 gr |

| | |
|---|---|
| Glycerol | 44.0 gr |

II. Inoculum

The inoculum was propagated in 20 g/l casein hydrolysate, 10 g/l yeast extract and 2 g/l NaCl. Sterile medium in a shake flask was inoculated from stock culture and incubated 15 hours on a shaker at 30° and approximately 200 r.p.m. As needed, subsequent stages in inoculum propagation were carried out in stirred aerated fermenters. Sterile medium was inoculated with 2–10% inoculum and incubated 15 hours at 30° C., pH 7±0.5 with agitation and aeration to maintain a dissolved oxygen level above 20% air saturation.

III. Production

The production medium contains:

| | |
|---|---|
| Casein hydrolysate | 20 g/l |
| Yeast extract | 10 g/l |
| $K_2HPO_4$ | 2.5 g/l |
| $MgSO_4.7H_2O$ | 1 g/l |
| NaCl | 5 g/l |
| Biotin | 0.1 mg/l |
| Thiamine | 1 mg/l |
| Trace elements solution | 3 ml/l |

The medium also contains 100 mg/liter ampicillin. The ampicillin is optional for production but is always found in the medium used for growing the inoculum.

Biotin, thiamine and ampicillin in concentrated solution were filter sterilized separately and added to the sterile production medium before inoculation. Sterile gulucose solution was added initially to supply 10 g/l. At the induction step another 10 g/l of glucose was added.

The trace elements solution contains

| | |
|---|---|
| $FeCl_3$ | 16 g/l |
| $ZnCl_2.4H_2O$ | 2 g/l |
| $CoCl_2.6H_2O$ | 2 g/l |
| $Na_2MoO_4.2H_2O$ | 2 g/l |
| $CaCl_2.2H_2O$ | 1 g/l |
| $CuCl_2$ | 1 g/l |
| $H_3BO_3$ | 0.5 g/l |
| Conc. HCl | 100 ml/l |

The medium is inoculated with 0.5–10% inoculum culture and incubated at 30° C. Agitation-aeration rates are set to maintain a dissolved oxygen level above 20% air saturation. The pH is maintained at 7±0.2 with $NH_3$. Once cell concentration reaches about 3.5 g/l ($OD_{660}=10$) induction is started.

The temperature is raised to 42° C. and maintained at 42° C. for 1–5 hours. The culture is then chilled and cells are recovered by centrifugation for hormone purification.

Recovery of bGH

Thirteen kilograms of bacterial cells (wet cake) are resuspended in 5 volumes of a solution containing 50 mM sodium phosphate buffer (pH 7.4), 50 mM EDTA and 100 mM NaCl, using a Polytron (Kinematica) blender, while controlling the blender's speed to minimize foaming. The homogenous suspension is continuously passed through a Dynomill cell disruptor KD5 (Willy A. Bacofen, Basel) at a rate of 80 liter per hour and the homogeneous suspension of disrupted cells clarified by centrifugation in a CEPA 101 centrifuge at a flow rate of 45 liter per hour. The precipitate from the centrifugation step is collected and resuspended in 15.5 liters of 50 mM sodium phosphate buffer (pH 7.4) containing 50 mM EDTA. Lysoszyme is added to a final concentration of 0.5 mg/ml and the suspension incubated for 16 hours at 37° C. Triton X-100 is added to a final concentration of 1%. The suspension is then incubated for 30 minutes at room temperature, sonicated in a continuous flow cell sonificator (Heat System) at a rate of 18 liters per hour and centrifuged in a CEPA 101 centrifuge. The precipitate is collected, resuspended in 50 mM sodium phosphate buffer (pH 7.4), sonicated as above, and centrifuged in a CEPA 101 centrifuge. The cells are resuspended in 15.5 liters of 50 mM sodium phosphate buffer (pH 7.4) containing 50 mM EDTA and 100 mM NaCl and twice precipitated and resuspended in 15.5 liters of distilled water. The precipitate is collected by centrifugation and stored at $-20°$ C.

Purification Of bGH

The precipitate is resuspended in 30–40 liters distilled water and solubilized by titration with 0.5N NaOH to pH 11.8. The solution is then continuously sonicated and clarified by centrifugation in CEPA 101 centrifuge if necessary, or filtered through Whatman No. 1 paper.

The clarified protein solution (32.6 liters containing 297,000 OD's at 280 nm) is divided into separate portions (6×5.4 liters) each containing 50,000–60,000 OD's. Each portion is ultrafiltered separately through a Millipore Pellicon ultrafilter equipped with three 100,000 molecular weight cutoff cassettes (type PTHK) of 5 ft$^2$ area each. A 5.4 liter portion is concentrated to 1 liter retentate volume. The ultrafiltrate is collected and saved. The retentate is diluted back to its original volume with fresh 10 mM Borate buffer, pH 11.8, and mixed well. The batch is concentrated again to 1 liter retentate volume. The ultrafiltrate is collected and combined with the first ultrafiltrate. When the running total of the OD's in the ultrafiltrates equals 20% of the OD's initially charged to the ultrafilter, the retentate volume on the next concentration steps is taken to 0.5 liters instead of 1 liter. The cycle of concentration and dilution with 10 mM Borate buffer is continued until the ultrafiltrate from a retentate volume of 0.5 liters has an absorbance at 280 nm (1-cm cell) of less than 0.1. This normally takes between 9 and 12 cycles of concentration an dilution. The final retentate is discarded.

All ultrafiltrates are combined and adjusted to pH 9.0 with 6N HCl. The other 5.4-liter portions are ultrafiltered in the same fashion, and all pH adjusted ultrafiltrates are combined. A typical run produces a total of 380 liters of ultrafiltrates with an absorbance of 0.26 equivalent to 100,000 OD's and requires 24 to 40 hours to complete.

The combined ultrafiltrates (380 liters containing 100,000 OD's at 280 nm) from the 100K ultrafiltration step are loaded onto a Sepharose CL-6B DEAE ion-exchange column at a linear flow velocity of 23 cm/hr (25 liter/hr). The 37-cm diameter 15-cm high column is washed with two bed volumes (32 L) of 10 mM Borate buffer at pH 9.0. The eluate from the loading and washing steps is discarded. A step change in eluent to 10 mM Borate, 100 mM sodium chloride, pH 9, displaces the bGH off the column. The elution flow velocity is 23 cm/hr. The progress of the run is monitored by following absorbance of the eluate at 280 nm. The bGH peak is collected in 4 to 5 bed volumes (84 liters containing 43,000 OD's at 280 nm) and then concentrated to approximately 10 mg/ml using a Millipore Pellicon ultrafiltration device with a 10,000 molecular weight cutoff cassette. The solution is then lyophilized. The yield is approximately 70 g of pure bGH.

EXAMPLE 6

Activity Of bGH Analog Produced By pRO12

1. Radioimmunoassay Comparison of bGH Analog with Natural bGH

A solution containing 100 ng/ml bGH analog was prepared in phosphate buffered saline including (1% BSA). This solution was diluted serially to concentrations of 50, 25, 12.5, 6.25, 3.12, 1.56 and 0.78 ng/l. Duplicate 0.1 ml aliquots of these solutions were submitted to RIA using a double antibody procedure. The dilution curve was comparable to that obtained with natural bGH.

2. Radioreceptor Binding Assay

A radioreceptor binding assay was performed with rabbit liver membranes as described by Tushima, T. and Freisen, H. G., (Y. Chin., Endocr. Metab. (1973), 37, 3) using $^{125}$I-bGH as the tracer and authentic bGH solutions for the construction of calibration curves. Samples were incubated in triplicate for two hours at room temperature in 0.3 ml of assay buffer (50 mM Tris, 15 mM $CaCl_2$ and 5 mg/ml bovine serum albumin, pH 7.6). The tubes contained $^{125}$I-bGH (20,000 cpm of preparation of 30–60 μci/μg), 150–250 μg liver membrane protein and either natural bGH (1–100 ng) or extracts of bacterial bGH. The result demonstratred that the bGH activity of the bGH analog is comparable to that of natural bGH.

3. Tibia Test

The bioactivity of the pRO12 produced bGH analog recovered from bacterial cells according to Example 5 was evaluated by a tibia test. (Parlow, A. F., et al., Endocrinology (1965) 77, 1126). Rats were hypophysectomized at 28–30 days of age, then kept for 10–14 days without treatment. Bovine growth hormone derived from bovine pituitaries or from recombinant *Escherichia coli* was dissolved in 0.15M NaCl+0.01M borate, pH 10.0. Rats (4–7 per group) received daily subcutaneous injections of bGH solutions (5–125 μg/day in 0.2 cc) for 5 days while kept on a normal diet (Purina Rat-Chow and water adlibitum). The animals were sacrificed on the 6th day, their foreleg knee-bones taken out, cut longitudinally, fixed with acetone and stained with 2% $AgNO_3$. The width of the epiphyseal plates was measured by observation through a dissecting binocular (Nikon). Mean values (40 readings per rat) were used for the constructon of long does-response curves. The results demonstrated that the bGH activity of the pRO12-produced bGH analog is comparable to that of natural bGH.

EXAMPLE 7

Growth Of SOD$\beta_1$T$_{11}$

1. Stock Cultures

Stock cultures of pSOD$\beta_1$T$_{11}$ were grown on casein medium (see Inoculum), then diluted two-fold with freezing medium and stored at −80° C. Freezing medium contains per 500 ml:

| | |
|---|---|
| $K_2HPO_4$ | 6.3 gr |
| $KH_2PO_4$ | 1.8 gr |
| Na Citrate | 0.45 gr |
| $MgSO_4.7H_2O$ | 0.09 gr |
| $(NH_4)_2SO_4$ | 0.9 gr |
| Glycerol | 44.0 gr |

II. Inoculum

The inoculum was propagated in 20 g/l casein hydrolysate, 10 g/l yeast extract and 2 g/l NaCl. Sterile medium in a shake flask was inoculated from stock culture and incubated 15 hours on a shaker at 30° C. and approximately 200 r.p.m. As needed subsequent stages in inoculum propagation were carried out in stirred aerated fermenters. Sterile medium was innoculated with 2–10% innoculum and incubated 15 hours at 30° C., pH 7±0.5 with agitation and aeration to maintain a dissolved oxygen level above 20% air saturation.

III. Production

The production medium contains:

| | |
|---|---|
| Casein hydrolysate | 20 g/l |
| Yeast extract | 10 g/l |
| $K_2HPO_4$ | 2.5 g/l |
| $MgSO_4.7H_2O$ | 1 g/l |
| NaCl | 5 g/l |
| Biotin | 0.1 mg/l |
| Thiamine | 1 mg/l |
| Trace elements solution | 3 ml/l |
| $CuSO_4$ | 0.8 g/l |
| $ZnSO_4$ | 10 mg/l |

The medium also contains 12.5 mg/liter tetracycline. The tetracycline is optional for production, but is always found in the medium used for growing the inoculum.

Biotin, thiamine and tetracycline in concentrated solution were filter sterilized separately and added to the sterile production medium before inoculation. Sterile glucose solution was added initially to supply 10 g/l. At the induction step another 10 g/l of glucose was added.

The trace elements solution contains:

| | |
|---|---|
| $FeCl_3$ | 16 g/l |
| $ZnCl_2.4H_2O$ | 2 g/l |
| $CoCl_2.6H_2O$ | 2 gf/l |
| $Na_2MoO_4.2H_2O$ | 2 g/l |
| $CaCl_2.2H_2O$ | 1 g/l |
| $CuCl_2$ | 1 g/l |
| $H_3BO_3$ | 0.5 g/l |
| Conc. HCl | 100 ml/l |

The medium is inoculated with 0.5–10% inoculum culture and incubated at 30° C. Agitation-aeration rates are set to maintain a dissolved oxygen level above 20% air saturation. The pH is maintained at 7±0.2 with $NH_3$. Once cell concentration reaches about 3.5 g/l ($OD_{660}$=10) induction is started.

The temperature is raised to 42° C. and maintained at 42° C. for 1–5 hours. The culture is then chilled and cells are recovered by centrifugation for enzyme purification.

Recovery Of SOD

One and one-half kilograms of bacterial cells (wet cake) are suspended in 12 liters of 50 mM sodium phosphate (pH 7.8), in a Polytron (Kinematica) blender while controlling the speed to minimize foaming. The homogeneous suspension is continuously passed through a Dynomill cell disrupter KD5 (Willy, A. Bachofen, Basel). The homogeneous suspension of disrupted cells is sonicated using a continuous flow cell and centrifuged in a CEPA 101 centrifuge. The supernatant is heated for 2 hours at 65° C., cooled and centrifuged as before. The clear supernatant is concentrated to 1 liter in a Millipore Pellicon ultrafiltration device using 10,000 molecular weight cutoff cassettes (type PTGC). The concentrated protein solution is passed through a DEAE-Sepharose column (2 Kg DEAE Sepharose) equilibrated with 150 mM sodium phosphate buffer (pH 7.8). The flow through solution is collected, concentrated and dialyzed in a Pellicon ultrafiltration device against 20 mM Tris-HCl, pH 7.8, and then applied on to a QAE-Sepharose column equilibrated with 20 mM Tris-HCl buffer. The column is developed with a 20 mM Tris HCl buffer, pH 7.8, and a salt gradient (0-200 mM NaCl). SOD-containing fractions are collected, concentrated using a Pellicon ultrafiltration device, dialzed against distilled water and then brought to 100 mM sodium acetate by adding 1M sodium acetate buffer, pH 4.8. The protein solution is then further separated on a CM-Sepharose column equilibrated with 100 mM sodium acetate buffer, pH 4.7. The column is developed using the same buffer and a salt gradient (100-500 mM NaCl). SOD containing fractions are collected, concentrated using a Pellicon ultrafilter device and lyophilized.

EXAMPLE 8

Activity Of SOD Produced By pSOD$\beta_1$T$_{11}$

The enzymatic activity of the SOD analog produced by pSOD$\beta_1$T$_{11}$ prepared in Example 7 was assayed by monitoring the inhibition of reduction of ferricytochrome-c as described by McCord and Fridovich, J. Biol. Chem. (1969), 244:6049-6055. The results demonstrated that the activity of pSOD$\beta_1$T$_{11}$-produced SOD analog was comparable to that of natural human SOD (Sigma) and to that of bovine SOD (Orgotein: Grunenthal GMBH).

EXAMPLE 9

The yield and activity of human superoxide dismutase produced by the SOD host-vector systems described in Example 3 may be improved by modifying the growth conditions of the host-vector systems. As the following data demonstrates supplementing the growth medium for the host-vector system with Cu and Zn results in a greater yield of the enzyme in active dimer form.

Growth of Bacteria Containing pSOD$\beta_1$T$_{11}$

I. Stock Cultures

Stock cultures of pSOD$\beta_1$T$_{11}$ were grown on casein medium (see inoculum), then diluted twofold with freezing medium and stored at −80° C. Freezing medium contains:

| | |
|---|---|
| K$_2$HPO$_4$ | 6.3 gr |
| KH$_2$PO$_4$ | 1.8 gr |
| Na Citrate | 0.45 gr |
| MgSO$_4$.7H$_2$O | 0.09 gr |
| (NH$_4$)$_2$SO$_4$ | 0.9 gr |
| Glycerol | 44 gr |
| Per 500 ml | |

II. Inoculum

The inoculum was propagated in 20 g/l casein hydrolysate, 10 g/l yeast extract and 2 g/l NaCl. Sterile medium in a shake flask was inoculated from stock culture and incubated 15 hours on a shaker at 30° C., and approximately 200 r.p.m. If needed subsequent stages in inoculum propagation were carried out in stirred aerated fermenters. Sterile medium was inoculated with 2-10% flask culture, and incubated 15 hours at 30° C., pH 7±0.5 with agitation and aeration to maintain dissolved oxygen level above 20% air saturation.

III. Production

The production medium contains:

| | |
|---|---|
| Casein hydrolysate | 20 g/l |
| Yeast extract | 10 g/l |
| K$_2$HPO$_4$ | 2.5 g/l |
| MgSO$_4$.7H$_2$O | 1 g/l |
| NaCl | 5 g/l |
| Biotin | 0.1 mg/l |
| Thiamine | 1 mg/l |
| Trace elements solution | 3 ml/l |
| Tetracycline | 12.5 mg/l |

In some of the experiments we added:

| | |
|---|---|
| CuSO$_4$.5H$_2$O | 0.8 g/l |
| ZnSO$_4$.7H$_2$O | 10 mg/l |

Biotin, thiamine, and tetracycline in concentrated solutions were filter sterilized separately and added to the sterile production medium before inoculation. Sterile glucose solution was added initially to supply 10 g/l. At the induction step another 10 g/l of glucose was added.

The trace elements solution contains:

| | |
|---|---|
| FeCl$_3$ | 16 g/l |
| ZnCl$_2$.4H$_2$O | 2 g/l |
| CoCl$_2$.6H$_2$O | 2 g/l |
| Na$_2$MoO$_4$.2H$_2$O | 2 g/l |
| CaCl$_2$.2H$_2$O | 1 g/l |
| CuCl$_2$ | 1 g/l |
| H$_3$BO$_3$ | 0.5 g/l |
| Conc. HCl | 100 ml/l |

The medium is inoculated with 0.3-10% inoculum culture and incubated at 30° C. Agitation-aeration rates are set to maintain dissolved oxygen level above 20% air saturation. The pH is maintained at 7±0.2 with NH$_3$. Once cell concentration reaches about 3.5 g/l (OD$_{660}$=10) induction is started.

The temperature is raised to 42° C. and maintained at 42° C. for 1-5 hours. The culture is then chilled, and cells are recovered by centrifugation for enzyme purification.

RECOVERY OF SOD

One and one-half kilograms of bacterial cells (wet cake) are suspended in 12 liters of 50 mM sodium phosphate (pH 7.8), in a Polytron (Kinematica) blender while controlling the speed to minimize foaming. The homogeneous suspension is continuously passed through a Dynomill cell disrupter KD5 (Willy, A. Bachofen, Basel). The homogeneous suspension of disrupted cells is sonicated using a continuous flow cell and centrifuged in a CEPA 101 centrifuge. The supernatant is heated for 2 hours at 65° C., cooled and centrifuged as before. The clear supernatant is concentrated to 1 liter in a Millipore Pellicon ultrafiltration device using 10,000 molecular weight cuttoff casettes (type PTGC). The concentrated protein solution is passed through a DEAE-Sephacel column (2 Kg DEAE Sephacel) equilibrated with 150 mM sodium phosphate buffer (pH 7.8). The flow through solution is collected, concentrated and dialyzed in a Pellicon ultrafiltration device against 20 mM Tris-HCL, pH, 7.8 and then applied on to a QAE-Sepharose column equilibrated with 20 mM Tris-HCl buffer. The column is developed with a 20 mM Tris-HCl buffer, pH 7.8, and a salt gradient (0–200 mM NaCl). SOD containing fractions are collected, concentrated using a Pellicon ultrafiltration device, dialyzed against distilled water and then brought to 100 mM sodium acetate by adding 1M sodium acetate buffer, pH 4.8. The protein solution is then further separated on a CM-Sepharose column equilibrated with 100 mM sodium acetate buffer, pH 4.7. The column is developed using the same buffer and a salt gradient (100–500 mM NaCl). SOD containing fractions are collected, concentrated using a Pellicon ultrafiltration device and lyophilized.

EXAMPLE 10

Reduction in Reperfusion Injury with Recombinant Human Superoxide Dismutase Following Global Ischemia Human superoxide dismutase produced by the host-vector system pSOD$\beta_1$T$_{11}$ in *E. coli* A1645 described in Example 3, grown and purified under the conditions described in Example 9 has been shown to reduce reperfusion injury following global ischemia.

Isolated Perfused Rabbit Heart Preparation

Female New Zealand white rabbits, 1.2–2.0 kg were heparinized and anesthetized, their hearts removed and quickly placed into cold (4° C.) perfusate. The ascending aorta was cannulated and the hearts perfused under constant pressure (110 cm of water) with a modified Krebs-Ringers bicarbonate buffer solution containing 117 mM sodium chloride, 6 mM potassium chloride, 3.0 mM calcium chloride, 1.0 mM magnesium sulphate, 0.5 mM EDTA, and 16.7 mM glucose with the final pH adjusted to 7.40 by the addition of approximately 24 mM sodium bicarbonate. The perfusate was bubbled continuously with 95% oxygen and 5% carbon dioxide. Coronary flow was removed from the NMR sample tube by vacuum aspiration. The hearts were paced at 175 beats/minute by right ventricular pacing with a wick soaked in saturated potassium chloride, encased in polyethylene tubing, and connected to a Grass SD-9 stimulator. To quantitate left ventricular contractile function a latex rubber balloon was tied to the end of a 100 cm length of PE 190 tubing, carefully purged of air bubbles and connected via a three-way stopcock to a Statham P23Db transducer. Isovolumic pressure was recorded with a Brush two channel direct writing recorder. The balloon was initially inflated via a syringe with a volume of saline sufficient to produce an end diastolic pressure of 10 mm Hg. All subsequent measurements of developed pressure were at this end diastolic volume. All hearts were subjected to 30 minutes of global ischemia during which time the hearts were maintained at 37° C. by a flow of warm perfusate around the heart. Total interruption of aortic in-flow was accomplished by cross clamping the perfusion line. Forty-five minutes of normothermic reperfusion (37°±2° C.) followed the period of ischemia. Recovery of left ventricular developed pressure was calculated as a percentage of the pre-ischemic control. At the onset of ischemia the balloon as deflated and the pacer turned off. The balloon as reinflated 15 minutes after initiating reflow, just prior to the first measurement of function with the same volume removed at the onset of ischemia. Coronary blood flow was measured volumetrically by vacuum aspiration prior to ischemia, 5 minutes after reflow and after 15, 30 and 45 minutes of reperfusion.

Nuclear Magnetic Resonance Methods

Phosphorous-31 NMR spectra were obtained in a Brucker WH 180 spectrometer at 4.23 Telsa in a wide bore super-conducting magnet. At this field strength, phosphorus resonates at 72.89 MHz. The diameter of the phosphorus probe is 25 mm. This instrument was operated in the pulsed Fourier transform mode and interfaced to a Nocolet 1280 computer and the data collected on high density magnetic disks. Because of the field stability of the super-conducting magnet, field/frequency lock is not required. Five minute proton decoupled spectra were collected from transients following 45° pulses delivered to two second intervals, conditions previously documented to result in minimal spectral saturation. The data were accumulated with a 2K table at a 3,000 Hz spectral width.

Estimation of Tissue Intracellular pH from NMR Spectra

Measurement of intracellular pH was determined from the chemical shift ($\delta_o$) of the inorganic phosphate peak by the following equation:

$$pH_I = pK - \log \frac{\delta_o - \delta_B}{\delta_A - \delta_o}$$

In order to minimize tissue inhomogeneity effects, chemical shift values were measured relative to the resonance of phosphocreatine which is relatively pH independent over the range of pH to be encountered in these studies (pK$_A$=4.6). The constants used in this equation are pK=6.90, $\delta_A$=3.290 PPM and $\delta_B$=5.805 PPM, as previously reported.

Quantitation of Metabolites from NMR Spectra

Estimations of tissue phosphocreatine (PCr), adenosine triphosphate (ATP), as well as inorganic phosphate (Pi) were obtained by planimetric measurements of the areas under the individual peaks allowing for the computer determined normalization constant or scaling factor. A Hewlett-Packard digitizer was used to perform the area integrations. Quantitative data thus derived for PCr, ATP and Pi are expressed as percent of the pre-ischemia control content.

Experimental Protocol

Seventeen hearts were divided into two groups:

| | |
|---|---|
| Group I | (n = 8) The hearts in this group were treated with 60,000 units of human recombinant superoxide dismutase (hSOD, specific activity 3,200 IU/mg) administered as a 10 ml bolus just prior to reflow, followed by a continuous infusion of 60,000 units during the first 15 minutes of reflow; hSOD was dissolved in warm 37° C. Krebs-Ringers bicarbonate perfusate. |
| Group II | (n = 9) The hearts in this group received a 10 ml bolus of perfusate just prior to reflow followed by normothermic reperfusion. |

Results

Recovery of Left Ventricular Function

The experimental ischemic model employed in the present study was specifically chosen following a series of preliminary studies to provide hearts which having suffered a moderately severe irreversible insult, still retained the potential for improvement with a therapeutic intervention. At the end of 45 minutes of reflow, the recovery of left ventricular function (as measured by percent recovery of control developed pressure) was $47\pm5\%$ for the control group with an end diastolic pressure to $48\pm7\%$ mm Hg (compared to a pre-ischemic control value of 10 mm Hg). These parameters did not change appreciably between 30 and 45 minutes of reperfusion, suggesting that a relatively steady state of recovery had been achieved. The administration of hSOD just prior to reflow and for the initial 15 minutes of reperfusion resulted in significantly improved preservation of cardiac function and in a smaller increase in end diastolic pressure compared to control hearts; hSOD treated hearts recovered $71\pm6\%$ of control developed pressure at an end diastolic pressure of only $27\pm4$ mm Hg (both P. 0.01 vs control).

Myocardial Metabolism During Ischemia and Following Reperfusion

Myocardial high-energy phosphate contents were serially measured during ischemia and following reperfusion in both control and hSOD-treated hearts. During the 30-minute ischemic period progressive decreases in myocardial creatine phosphate and ATP content were observed. Phosphocreatine content fell by the end of the ischemic period to $8\pm3\%$ of the pre-ischemic baseline value in control hearts and to $10\pm5\%$ of control in those hearts which were subsequently to be treated with hSOD; ATP content reached $36\pm6\%$ of the baseline value in control hearts and $33\pm6\%$ in hSOD treated hearts. These data clearly indicate that both groups of hearts were subjected to an equally severe degrees of ischemia. These data also rule out the possibility the hearts receiving hSOD demonstrated better functional recovery due to better preservation of cellular metabolism during the ischemic period by some uncontrolled for mechanism.

At the end of 345 minute reflow period hSOD-treated hearts displayed a nearly normal content of phosphocreatine ($93\pm9\%$ of control) whereas control hearts recovered only $69\pm7\%$ of the original value (P<0.05). At the end of the reflow period ATP content was equal in both groups of hearts ($41\pm4\%$) in control vs $42\pm5\%$ in hSOD-treated hearts). This latter result might reflect increased energy demands of hearts recovering better left ventricular function, in the presence of a limited ability to increase rates of high energy phosphate production. In contrast, poorer recovery of function in control hearts would result in less utilization of high energy phosphate metabolites, possibly masking even more severe limitation in energy production.

In conclusion, these data demonstrate, in hearts subjected to a moderately severe ischemic insult and subsequent reperfusion, the administration of hSOD just prior to and during early reperfusion results in better recovery of systolic and diastolic function, as well as in higher myocardial content of phosphocreatine. These data also suggest that reperfusion of ischemic myocardium may result in a component of structural and/or functional damage which can be avoided or reduced by the administration of an oxygen free radical scavenger such as hSOD at the time of reperfusion. Thus, by limiting that component of reflow injury resulting from reoxygenation of previously ischemic myocardium, hSOD may provide a valuable addition to thrombolytic therapy and/or coronary angioplasty in patients treated early after acute myocardial infarction.

EXAMPLE 11

Reduction in Experimental Infarct Size by Recombinant Human Superoxide Dismutase Administration During Reperfusion Human superoxide dismutase produced by the host vector system pSOD$\beta_1$T$_{11}$ in *E. coli* A1645 described in Example 3, grown and purified under the conditions described in Example 9 has been shown to reduce infarct size in hearts.

Timely reperfusion of the ischemic myocardium reduces infarct size (IS); however, this beneficial effect may be blunted by the simultaneous occurrence of reflow injury, mediated through the generation of toxic oxygen free radicals. To test whether scavenging of free radicals by recombinant human superoxide dismutase (hSOD) could result in a reduction of IS compared to reperfusion alone, in 16 anesthetized dogs the circumflex coronary artery was occuluded before any marginal branch for 90 min.; at the time of reperfusion the animals were injected with either hSOD (400,000 units as a bolus into the left atrium, followed by 300,000 units as 1 hr. i.v. infusion; n=8), or with a similar amount of saline (controls, n=8). The chest was then closed and the animals were allowed to recover. After 48 hrs. the dogs were sacrificed and the hearts processed in a blinded fashion for the evaluation of IS by gross pathology and of the risk area by postmortem angiography. Proximal occlusion of the circumflex artery resulted in ischemia of $40.8\pm2.3\%$ of the left ventricle (LV) in controls and $41.8+2.0$ in treated dogs. In control dogs reperfusion was associated with infarction of $52.2+7\%$ of risk area; hSOD treatment, however, resulted in a significant reduction of necrosis, IS being $33.6+2.1\%$ of risk area (p<0.05). Control animals developed confluent, nontransmural infarcts which extended throughout most of the risk area, whereas in treated dogs the infarcts appeared more patchy and non-confluent. In conclusion, free radical scavenging by hSOD administered at the same time of reperfusion significantly reduced the extent of necrosis, possibly through a prevention of reflow injury.

EXAMPLE 12

The Role of Oxygen Free Radicals in Mediating the Reperfusion Injury of Cold Preserved Ischemic Kidneys[1]

[1] Abbreviations used in this example: $C_{CR}$, Crestinine clearance; ATP, adenosine triphosphate; ADP, adenosine diphosphate; AMP, adenosine monophosphate.

In a new indication, human superoxide dismutase can reduce reperfusion injury following transplantation of organs. The following Example demonstrates that superoxide dismutase ameliorates injury on reperfusion following the transplantation of a kidney. The human superoxide dismutase utilized in this example was produced by the host-vector system pSOD$\beta_1$T$_{11}$ in *E. coli* A1645 described in Example 3, and grown and purified under the conditions described in Example 9.

The parenthesized arabic numbers found throughout this Example refer to the articles listed in the Bibliography at the end of this Example.

Model of Renal Preservation and Transplantation Ischemia In Swine

Female, outbred pigs, weighing 15 to 18 kg were premedicated with acepromazine and atropine, and anesthetized with ketamine and halothane. In the donor pigs, diuresis was established 30 minutes prior to harvest by the intravenous administration of 1500 cc of Ringer's lactate, furosemide (20 mg) and mannitol (12.5 g). Phenoxybenzamine (50 mg) was given intravenously to prevent renal vasopasm, which can be seen frequently in pigs. Through a midline abdominal incision, the distal aorta and vena cava were mobilized, just proximal to their bifurcations. The ureters were dissected and divided at the level of the bladder. An inflow catheter was placed in the aorta, just above the bifurcation, and an outflow catheter was placed into the inferior vena cava. Heparin (5,000 units) was given intravenously and a continuous flush with Euro-Collins solution at 4° C. was initiated through the distal aorta, coincident with the cross-clamping of the aorta just above the renal artery. After the kidneys had been cooled in situ, they were removed en block. The kidneys were then separated and one was assigned to be the control and the other to be the test kidney, thus facilitating a paired design. Each kidney was then flushed again with 4° C. Euro-Collins solution. When called for by the protocol, test substances were added to the preservation fluid of the second kidney at this time. Both kidneys were packed sterilely and stored at 4° C. overnight.

After 24 hrs. of cold ischemia, a fresh recipient animal was anesthetized and the preserved kidneys were transplanted to its iliac vessels. The time required for each anastomosis was 25 to 30 min. the control (untreated) kidney was always transplanted first, the test kidney second. Reperfusion of the test kidney was therefore always delayed for a total of one hour after the reperfusion of the control kidney. This means that the control kidneys were subjected to 23 hours of cold ischemia, the test kidneys to 24 hours. Test drugs were administered systemically (allopurinol) or intraarterially (superoxide dismutase=SOD) beginning one hour after reperfusion of the control kidney at the time of reperfusion of the test kidney. Thus, the control kidney was exposed to the toxic effects of rewarming and reperfusion for one hour before exposure to any possible effects of agents provided to the test kidney. Following reperfusion of the second kidney, the native kidneys of the recipient pig were removed. Additional doses (10 g) of mannitol were given prior to reperfusion of first the control, and then again of the test kidney, to mimic clinical practice. This allowed evaluation of the effect of free radical modifying agents superimposed upon optimal conventional preservation/transplantation techniques. The ureter from each kidney was brought out separately as a cutaneous ureterostomy.

Two days following transplantation, the recipient was lightly anesthetized and urine was collected for one hour from each kidney (ureterostomy) separately and assayed for volume and creatinine concentration. Serum creatinine was also determined, allowing the calculation of creatinine clearance separately for each kidney.

All results are expressed as mean±SEM. Data were analyzed during the Student t-test (two-tailed). In most cases a paired test could be applied due to the paired design of the experiments.

Experimental Protocol

Superoxide Dismutase (SOD) and Catalase

Sigma bovine blood superoxide dismutase, a scavenger of oxygen free radicals, was administered to test kidneys in four pigs. A 5 mg bolus was given into the renal artery immediately prior to reperfusion, and a constant intraarterial infusion was maintained at 1 mg/min during the first 15 min. of reperfusion. This provided a total dose of 20 mg of SOD. In a second group of four pigs, the test kidneys received catalase (Sigma Co.), by the same dosage regimen, in addition to SOD. The other kidney in each of these pigs received no treatment, and thus served as a control.

Dose Response to SOD

In order to determine the minimal dosage for maximal protection, a dose response relationship was studied. At revascularization, one kidney received an infusion of a lesser of two doses of SOD and the other the next higher dose. Human recombinant SOD prepared as described in Example 9 was given as described above. Two comparisons were made at each dosage range. In the first, 0.2 mg of SOD was compared with saline solution as the control. Stepwise, 0.2 mg was compared to 2 mg, 2 mg as compared to 20 mg, and finally 20 mg to 100 mg. In each case, the kidney to receive the lesser dose was transplanted first, in order to avoid the possible problem of SOD retention in the circulation at the time of the second transplant.

Results

The Effect of Bovine SOD and Catalase

The creatinine clearance for a normal single kidney in pigs of the size we used, under the above conditions of anesthesia and hydration, was 25.5+6.3 ml/min. (n=8). The administration of SOD in a dose of 20 mg into the renal artery for the first 15 min. of reperfusion substantially ameliorated the renal functional impairment after cold ischemia. The four kidneys treated with SOD alone had a mean creatinine clearance of 23.2±4.5 ml/min.), almost three times that of the control kidneys (8.4±1.7 ml/min., p<0.05). A combination of SOD and catalase provided similar, but not greater, protection ($C_{CR}$=19.0±4.5 ml/min.). In early pilot experiments, a separate group of four pigs had undergone transplantation with anastomotic times in excess of 40 minutes. Although renal function was significantly increased by SOD and catalase, in these animals, both treated and control kidneys had very poor function ($C_{CR}=4.8\pm0.8$ vs. $1.6\pm0.4$ ml/min.). In these kidneys, presumably subjected to more severe injury due to ischemia per se prior to reperfusion, modification of free radical injury was unable to restore normal renal function.

Human SOD Analog Dose Reponse Relationships

Infusions of human SOD analog (0.2 mg and 2 mg) provided no improvement in renal function compared to the controls. However, the mean creatinine clearance of kidneys receiving 20 mg of SOD analog was $14.2+1.1$ ml/min., significantly better than in the pairs receiving 2 mg infusions ($7.7\pm1.0$ ml/min. $p<0.05$). No further benefit was obtained from 100 mg of SOD analog ($C_{CR}=16.1\pm1.2$ ml/min.). Therefore, the minimal effective dose of SOD analog proved to be greater than 2 and less than 20 mg when administered in this manner. The human SOD analog was as effective as the bovine SOD.

Discussion

The paired design was employed to maximize differences due to the treatment regimens employed, and to control for confounding variables which were related to the particular donor or recipient animal. It also provided for a paired statistical analysis of results, which allowed optimal use of small numbers of relatively expensive experimental animals.

The striking finding of these studies was the magnitude of the benefit provided by ablation of free-radical mediate reperfusion injury. Despite the fact that the control kidneys received the benefits of optimal conventional methods for organ preservation, including healthy donor kidneys and recipient animals, hydration, alpha adrenergic blockage, anticoagulation, and diuresis, they demonstrated a severe functional lesion, with creatinine clearance levels depressed to values less than a third of normal. This 24 hours period of ischemic preservation, as it often does in similar clinical circumstances, exceeds conventional organ preservation capabilities. Treatment with effective doses of bovine SOD or human SOD analog dramatically prevented this injury, preserving renal function at near normal levels. Indeed, there was not a single kidney so treated that did not have a creatinine clearance at least twice that of its paired, untreated control, when measured 48 hours after transplantation. The magnitude of this benefit was therefore quantitatively greater than that seen by others following 45-60 minutes of warm ischemia. This suggests that with optimal conventional preservation techniques, the injury due to ischemia per se has been minimized, allowing the injury produced at reperfusion to become predominant. This interpretation is further supported by the studies with kidneys preserved 18 hours prior to reperfusion. In these kidneys, function was excellent in both the control and the treatment groups, suggesting that sufficient time had not elapsed to allow the accumulation of enough metabolites to set up the conditions favoring free radical generation at reperfusion. On the other hand, when the kidneys were subjected to a more severe degree of ischemia per se, as in the early pilot experiments with prolonged anastomosis (i.e., warm ischemia) times, SOD was not able to restore function to near normal levels, although a significant improvement was still seen. These kidneys would therefore be more analogous to those studied following shorter periods of warm ischemia (7,8,9). As in other organs, the benefits of obviating free radical injury are primarily related to the relative proportions of the injury that are due to ischemia itself, compared to that due to reperfusion.

Furthermore, the achievement of this increment of benefit appears to be obtained either wholly, or not at all. The dose response studies with SOD showed either maximal protection, or no protection whatsoever. Catalase provided no additional benefit when added to SOD alone. Within the quantitative limits of resolution of this study, the prevention of reperfusion injury appears to have been an all-or-nothing phenomenon.

The findings of this study, however, appear to be particularly relevant to clinical application. The 24 hour period of cold ischemia chosen corresponds well with the periods of cadaveric graft preservation necessitated by clinical circumstances. Furthermore, these studies evaluated the efficacy of free radical reperfusion injury ablation in the face of optimal conventional preservation and transplantation methods. This includes the use of mannitol, itself a potent hydroxyl radical scavenger. These studies therefore suggest that a similar degree of benefit might well be obtained by superimposing free radical ablation on current clinical practices. As SOD is a nontoxic compound, this approach seems promising.

BIBLIOGRAPHY

1. Parks D.A., Bulkley G.B., Granger D.N., Hamilton S.R., McCord J.M. Ischemic Injury to the Cat Small Intestine: Role of Superoxide Radicals. Gastroenterology 82:9 (1982).

2. Manson P.N., Anthenelli R.M., Im M.J., Bulkley G.B., Hoopes J.E. The Role of Oxygen-Free Radicals in Ischemic Tissue in Island Skin Flaps. Ann Surg 198:87 (1983).

3. Shlafter M., Kane P.F., Kirsh M.M. Superoxide Dismutase Pluse Catalase Enhance the Efficacy of Hypothermic Cardioplegia to Protect the Globally Ischemic, Reperfused Heart. J Torac Cardiovasc Surg 83:830 (1982).

4. Stuart R.S., Baumgartner W.A., Borkon A.M., et al. Five-Hour Hypothermic Lung Preservation with Oxygen Free-Radical Scavengers. Transplant Proc 17:1454 (1985).

5. Sanfey H., Bulkley G.B., Cameron J.L. The Role of Oxygen Derived Free Radicals in the Patholgenesis of Acute Pancreatitis. Ann Surg 200:405 (1984).

6. Hansson R., Gustavsson B., Jonsson O., et al. Effect of Xanthine Oxidase Inhibition on Renal Circulation After Ischemia. Transplant Proc 14:51 (1982).

7. Ouriel K., Smedira N.G., Ricotta J.J. Protection of the Kidney After Temporary Ischemia: Free Radical Scavengers. J Vasc Surg 2:49 (1985).

8. Peller M.S., Hoidal Jr, Ferris T.F. Oxygen Free Radicals in Ischemic Acute Renal Failure in the Rat. J Clin Invest 74:1156 (1984).

9. Im M.J., Shen W.H., Pak C.I., Manson P.N., Bulkley G.B., Hoopes J.E. Effect of Allopurinol on the Survival of Hyperemic Island Skin Flaps. Plast Reconstr Surg 73:276 (1984).

10. Parks D.A., Bulkley G.B., Granger D.N. Role of Oxygen Free Radicals in Shock, Ischemia, and Organ Preservation. Surgery 94:428 (1983).

11. Toledo-pareyra L.H., Simmons R.L., Najarian J.S. Effect of Allopurinol on the Preservation of Ischemic Kidneys Perfused with Plasma or Plasma Substitutes. Ann Surg 180:780 (1974).

12. Vasco K.A., DeWall R.A., Riley A.M. Effect of Allopurinol in Renal Ischemia. Surgery 71:787 (1972).

13. Owens M.L., Lazarus H.M., Wolcott M.W., Maxwell J.G., Taylor J.B. Allopurinol nd Hypoxanthine Pretreatment of Canine Kidney Donors. Transplantation 17:424 (1974).

14. Granger D.N., Rutilli G., McCord J. Superoxide Radicals in Feline Intestinal Ischemia. Gastroenterology 81:22 (1981).

15. Roy R.S., McCord J.M. Superoxide and Ischemia: Conversion of Xanthine Dehydrogenease to Xanthine Oxidase. In: Greenwald R., Cohen G., eds. Oxyradical and Their Scavenger Systems (Vol. 2). Cellular and Molecular Aspects. New York: Elsevier Science 145 (1983).

16. Toledo-pareyra L.H., Simmons R.L., Olson L.C., Najarian J.S. Clinical Effect of Allopurinol on Preserved Kidneys: A randomized Double-Blind Study. Ann Surg 185:128 (1977).

17. Parks D.A., Granger D.N., Bulkley G.B. Superoxide Radicals and Mucosal Lesions of the Ischemic Small Intestine (Abstract). Fed Proc 41:1742 (1982).

18. Casale A.S., Bulkley G.B., Bulkley B.H., Flaherty J.T., Gott V.L., Gardner T.J. Oxygen Free-Radical Scavengers Protect the Arrested, Globally Ischemic Heart Upon Reperfusion. Surg Forum 34:313 (1983).

EXAMPLE 13

Survival of Isolated Rabbit Cornea and Free Radical Scavengers

Human superoxide dismutase produced by the host vector system pSOD$\beta_1$T$_{11}$ is $E.$ $coli$ A1645 described in Example 3, grown and purified under the conditions described in Example 9 was shown to prolong the survival period of excised isolated corneas.

The parenthesized arabic numbers found throughout this Example refer to the articles listed in the Bibliography at the end of this Example.

Previous studies established the beneficial effect of low concentration of adenosine on the rabbit corneal endothelial pump in vitro (1). Activation of the fluid pump was obtained by perfusing the isolated cornea with physiological concentration of glucose (5 mM) and adenosine ($10^{-6}$M) in a balanced salt solution; the survival time was about 7 hours.

Our next goal was to increase the survival time. Superoxide dismutase (SOD) (2), scavenges the superoxide free radicals by catalyzing the reaction $O_2^- + O_2^- + 2H^+ \rightarrow H_2O_2 + O_2$. Administration of SOD is known to significantly increase the survival of ischemic tissues after partial anoxia (3).

Substantial degree of tissue damage resulting from ischemia occurs during the period of reperfusion and reoxygenation of the isolated tissues. Most of that injury is mediated through the superoxide radical and its desif superoxide dismutase (SOD) or catalase are able to prolong the survival of the isolated cornea.

We isolated corneas from albino rabbit weighing 2.0-3.0 kg. The details of the techniques used have been previously described (1). Briefly, the eyes were excised and the corneal epithelia scraped off; then the corneas were isolated as described, and subjected to perfusion.

Results

The addition of 2 $\mu$/ml of SOD analog to the Basal Salt solution containing 5 mM glucose and 1 $\mu$M adenosine prolonged the survival time of the isolated cornea from 7 hours to 14 hours. If the adenosine was eliminated, the survival time was prolonged to only 12 hours.

In summary, the SOD analog was demonstrated to be useful in prolonging the survival time of isolated corneas. The SOD analog may be important in prolonging the survival of other isolated organs as well. Similar data using bovine SOD has been published in Experimental Eye Research 4:153-154 (1985).

BIBLIOGRAPHY

1. Neuwirth, O. and Dikstein, S. (1983). The effect of cyclic AMP on the rabbit corneal endothelial fluid pump. Current Eye Res. 2(8), 565-567.

2. Fridovich, I. (1975). Superoxide dismutases. Ann. Rev. Biochem. 44, 147-159.

3. Manson, P.N., Robert, M., Anthenelli, M.M., Michael, J., Bulkley, G.B. and Hoopes, J.E. (1983). The role of oxygen-free radicals in ischemic tissue injury in Island skin flaps. Ann. Surg. 198, 87-90.

4. Michaelson, A.M. and Puget, K. (1980), Cell penetration by exogenous superoxide dismutase. Acta Physiol. Scand. Suppl. 492, 67-80.

5. Perlman, M. and Baum, J.L. (1974). The mass culture of rabbit corneal endothelial cells. Arch. Ophthalmol. 92, 235-237.

6. Klyce, S. and Maurice, D.M. (1976). Automatic recording of corneal thickness in vitro. Invest. Ophthalmol. 15, 550-553.

7. Neuwirth Lux, O. (1984). Survival of rabbit corneal endothelial pump. Ph.D. thesis, submitted to the Senate of the Hebrew University of Jerusalem.

8. Baret, A. and Emerit, I. (1983). Variation of superoxide dismutase levels in fetal calf serum. Mutation Res. 121, 293-297.

9. Marklund, S., Holme, E. and Hellner, L. (1982). Superoxide dismutase in extracellular fluids. Clin. Chim. Acta 126, 41-51.

10. Packer, J.E., Mahood, J.S., Mora Arellano, V.D., Slater, T.F., Willson, R.L. and Wolgenden, B.S. (1981). Free radicals and singlet oxygen scavengers: reaction of a peroxy radical with $\beta$-carotene, Diphenyl Furan and 1,4,Diazobicyclo(2,2,2)-octane. Biochem. Biophys. Res. Commun. 98(4), 901-906.

11. Singh, A. (1978). Introduction: interconversion of singlet oxygen and related species. Photochem. Photobiol. 28, 429-433.

12. Khan, A. (1978), Activated oxygen singlet molecular oxygen and superoxide anion, Photochem. Photobiol. 28, 615-627.

EXAMPLE 14

Use of Recombinant SOD in Treating Spinal Cord Ischemia

In a new indication, demonstrated by the following example, human superoxide dismutase has been shown to reduce reperfusion injury following spinal ischemia. The human superoxide dismutase utilized in this example was produced by the host-vector system pSOD$\beta_1$T$_{11}$ in $E.$ $coli$ A1645 described in Example 3, and grown and purified under the conditions described in Example 9.

Anesthetized dogs were connected to the Nicolet Compact 4 evoked potential system, and we obtained the baseline SEP (Somatosensory Evoked Potentials) by applying 250 stimuli consecutively at the rate of 4.7 stimuli per second to the posterior tibial nerve. The evoked potential of 250 stimuli were recorded from 2 electrodes over the Fpz and Cz (two specific points over the scalp), averaged by signal averager to reduce the signal to noise ratio, and the SEP was displayed on a screen.

A left thoracotomy was then performed, the descending aorta just distal to the left subclavian artery was dissected and isolated in preparation for the application of the crossclamp. A purse string was inserted proximal to the proposed site of the aortic crossclamp and a size 20 gauge cannula inserted for monitoring the proximal aortic pressure and infusion of the medication as in the experimental group. A size 14 gauge cannula was inserted into the right femoral artery for BP monitoring and removal of blood to control BP after the aortic crossclamp is applied. Serial blood gases were taken and the respirator was adjusted to maintain the blood gases within normal limits.

The aortic crossclamp was then applied just distal to the left subclavian artery. SEP is repeated at one minute intervals. The proximal aortic hypertension was controlled by removing blood from the femoral artery to maintain BP at 90-110 mm Hg mean. The aortic crossclamp was maintained for 10 more minutes after the SEP disappear. Disappearance of the SEP tracing signifies that the ischemia within the spinal cord produced by the crossclamping of thoracic aorta is severe enough to compromise the conduction of afferent impulses within the dorsal column of the spinal cord. The crossclamp was removed 10 minutes after the disappearance of SEP. The dogs would become hypotensive which responded to infusion of blood, Ringer's lactate and sodium bicarbonate.

In control dogs (n=8), the animals did not receive any recombinant SOD. In the experimental animals, one group (n=8) received a bolus of 25,000 units of recombinant SOD prior to removal of the crossclamp followed by 5,000 units per minute for 10 minutes; the second experimental group (n=7) received 5,000 units of recombinant SOD prior to removal of the crossclamp followed by 10,000 units per minute for 10 minutes.

Postoperatively, the neurological status of the hind limbs was accessed by Tarlov's criteria: 0=no movement in hind limbs; 1=slight movement of hind limbs; 2=good movement of hind limbs, but unable to stand; 3=able to stand but not normally; and 4=complete recovery. On the seventh postoperative day, SEP were repeated and recorded for comparison to the baseline. The animals were then sacrificed.

The results are:

| Neurological status on the seventh postoperative day (POD): | |
|---|---|
| Control animals (n = 8) | - 4 animals were grade 0 |
| | - 4 animals were either grade 2 or 3 |
| Experimental animals (I) - 25,000 units SOD bolus and 5,000 units/minute × 10 minutes. | |
| | - 6 animals showed complete recovery |
| | - 2 animals were in either grade 2 or 3. |
| Experimental animals (II) - 50,000 units SOD bolus and 10,000 units/minute × 10 minutes. | |
| | - all 7 animals showed complete recovery. |

Time taken for SEP to disappear after application of aortic crossclamp varies from 12 to 19 minutes. Since the crossclamp was maintained for 10 more minutes after SEP disappear, the total crossclamp time will be more than 20 minutes.

In the immediate postoperative period after the closure of thoracotomy wound, repeat SEP were taken. In the control animals, there was no SEP tracing discernible, in contrast, the treated animals showed a return of SEP tracing with delay in the latency of the waveform.

In summary, recombinant SOD proved to be useful in preventing neurologic injury due to spinal cord ischemia. This method of treatment is especially important in surgery of the aneurysms of the thoracic aorta.

EXAMPLE 15

Construction of Prototrophic Strains and Production of bGH Using Prototrophic Hosts Prototropic strains of *E. Coli* have been constructed which enable high level protein expression by many of the previously described plasmids even when grown in a minimal media. The advantages of a bacterial growth protocol using minimal media are:

a) the bacteria can be grown to a higher cell density;
b) it is easier to duplicate growth conditions as the media components are "simpler" and therefore of a higher quality; and
c) the media is more economical.

The preferred prototrophic strains of this invention are designated A4200, A4255, and A4346. Strain A4255 containing the plasmid p9200 has been deposited with the ATCC under Accession No. 53215, and is referred to as A4320.

Selection and Construction of the Prototrophic Strains

The following strains were screened for high growth rates on minimal media, and sensitivity to phageλ, λ434 and phage P1:

| | Strain |
|---|---|
| 1. | ATCC 12435 |
| 2. | ATCC 23716 |
| 3. | ATCC 27662 |
| 4. | ATCC 25404 |
| 5. | ATCC 11775 |
| 6. | ATCC 25254 |
| 7. | HfrC = A4134 |
| 8. | W3350 = A2509 |
| 9. | A1645 |

Based on results of these studies, we focused the development of a prototrophic strain based on strains ATCC 12435 and ATCC 25404 which were sensitive to the above-listed phage and showed superior growth rates. Using these two strains, we constructed new strains containing the λcI857 repressor by transducing them with P1 containing λcI857 ΔH1 ΔBam H1:Tn10. Tetracycline resistant colonies were purified and cured of P1 if necessary.

The resulting strains and their genotypes are:

A4200=ATCC 12435 (λcI857 ΔH1 ΔBam H1):Tn10

A4206=ATCC 25404 (λcI857 ΔH1 ΔBam H1):Tn10

Both strains were transformed with pHG44 yielding strains A4202 and 4207 respectively.

Growth and Induction

Strains A4202 and A4207 were grown and induced under the following conditions and assayed for production of bovine growth hormone analog.

Media

| Component | Concentration |
|---|---|
| KH$_2$PO$_4$ | 13.6 gm/liter |
| (NH$_4$)$_2$SO$_4$ | 2 gm/liter |
| MgSO$_4$.7H$_2$O | 0.2 gm/liter |
| CaCl$_2$ | 0.01 gm/liter |
| FeSO$_4$.7H$_2$O | 0.5 g/liter |
| pH 7.4 | |
| Supplements | |
| Glucose 20% solution | 25 ml/liter |
| Ampicillin 20 mg/ml solution | 1 ml/liter |
| B1 0.3% solution | 1 ml/liter |
| Biotin 0.3% solution | 1 ml/liter |

Both A4202 and A4207 grow well in minimal media; however, only A4202 expresses significant levels of the bGH analog. A4202 expresses the bGH analog at roughly the same level as pHG44 grown in rich media.

Elimination of Tetracycline Resistance From A4200

In order to utilize the prototrophic strain A4200 with plasmids carrying only a tetracycline resistance marker, we constructed a strain cured of the Tn10 marker. Strain A4200 was streaked on MacConky galactose plates, gal+ revertants were selected and tested for sensitivity to tetracycline and immunity to lambda phage. This strain was designed A4255.

Construction of Biotin Independent Prototrophic Strains

All of the above prototrophic strains contain the lambda cI857 delta H1 delta Bam H$_1$1 deflective prophage. The delta H1 deletion extends to the bio uvr B region, removing the biotin biosynthetic operons. Thus the strains require the addition of biotin to the growth media.

To eliminate the biotin requirement of strains derived from A4200 and A4255, we have introduced an F' episome from strain A89 into these strains.

Strain A89 carries an F' gal plasmid. We have demonstrated that this F' plasmid carries all the genes necessary for the endogenous synthesis of biotin. Several properties make this plasmid a convenient source of the bio operons:

1. F' gal is a unit copy plasmid.
2. The plasmid is extremely stable in *E. coli*.
3. F' plasmids are compatible with colE1 plasmid, on which our expression vectors are based.
4. F' is a conjugative plasmid. It can, therefore, be easily transferred from cell to cell.
5. One can easily screen for biotin independent strain.

Strain A4202 was conjugated for 30 minutes with A89, and biotin independent colonies were selected. The resulting strain A4346 yields high levels of bovine growth hormone analog following induction in minimal glucose medium in the absence of biotin. No other growth factor is required.

A4346 can be cured of pHG44 using standard methods known to those skilled in the art. The resulting prototrophic host strain can be transformed by all the plasmids described in this application.

Minimal Media

The minimal media standardly used for production purposes with the prototrophic strains was:

| | For Fermenters | For Shake Flasks |
|---|---|---|
| K$_2$HPO$_4$ | 6 g/l | 6 g/l |
| KH$_2$PO$_4$ | 4 g/l | 4 g/l |
| NH$_4$Cl | 1 g/l | 1 g/l |
| MgSO$_4$.7H$_2$O | 3 g/l | 0.2 g/l |
| 10% FeNH$_4$ Citrate | 0.3 ml/l | 0.1 ml/l |
| Trace Elements Solution | 3 ml/l | 1 ml/l |
| Antifoam, Silicone Autoclave. | 0.5 ml/l | |

Ampicillin (100 ml/l) or tetracycline (12.5 mg/l) may be added to the media depending on whether the strain is ampicillin or tetracycline resistant, respectively.

50% glucose was autoclaved separately and added to 20 gm/l. 50% glucose was fed during the fermentation at a rate of approximately 1.08 gm/glucose per O.D. unit for strains without the F' episome, or at a rate of 1.8 gm/glucose per 2.0 unit for strain A4346. The pH was controlled by feeding 25% NH$_4$. Antifoam was added as needed. Biotin was added at 15 mg/l for strains based on A4200, A4255 and A4206. The trace elements solution contains (Biotechnol. Bio-eng. 16:933–941 (1974)):

| | g/l |
|---|---|
| H$_3$BO$_3$ | 0.57 |
| CuCl$_2$ (CuSO$_4$.5H$_2$O) | 1.0 (0.04) |
| CaCl$_2$.2H$_2$O | 1.0 |
| MnSO$_4$.4H$_2$O | 0.81 |
| Na$_2$MoO$_4$.2H$_2$O | 2.0 |
| CaCl$_2$.6H$_2$O | 2.0 |
| ZnCl$_2$.4H$_2$O (ZnSO$_4$.7H$_2$O) | 2.0 (2.78) |
| Concentrated HCl | 100 ml |

The compounds in parenthesis are alternate compounds which may be used in place of the compounds preceding them. The parenthesized amounts refer to appropriate amounts of such alternative compounds. Many of the previously described plasmids have been introduced into the prototrophs A4200 and A4255. A partial list of these strains is described in the table below:

| Strain Designation | | Host Strain/Plasmid |
|---|---|---|
| A4202 | = | A4200/pHG44 |
| A4256 | = | A4255/pHG44 |
| A4320 | = | A4255/p9200 |
| Z1803 | = | A4255/pSODβ$_1$T11 |
| A4500 | = | A4255/pTV 194 |
| A4346 | = | A4200/pHG44, F'Gal |

EXAMPLE 16

Construction of Lytic Hosts and Production of bGH Using These Lytic Hosts

1. Construction of Strains A4048 and A3111

The strain W3350 has been used extensively for growing phage lambda (see, for example, Oppenheim and Salomon (1970), 41 Virology, 151–159). Strain A2509, a prototrophic derivative of W3350, was transduced by PlcIts grown on A1637, and also transduced with a λcI857 ΔH1 ΔBam H1 defective prophage carrying the Tn10 marker. The resulting strain A4048 was selected as a tetracycline resistant clone carrying the defective prophage λcI857 ΔH1 ΔBam H1. This strain also carried a PlcIts plasmid. This strain was transformed by pHG44 to yield strain A3111.

Similarly, strain A4085 was also constructed from A2509 by the insertion of λcI857 ΔH1 ΔBam H1, the removal of the Tn10 transposon and the curing of the PlcIts plasmid prior to transformation with pHG44. Strain A4085 carries the defective prophage λcI857 ΔH1 ΔBam H1 and serves as a control for measuring bGH production and the autolysis affected without the presence of the P1 plasmid. Strain A3111 has been deposited in the ATCC under Accession No. 53217.

2. Synthesis of Bovine Growth Hormone (bGH).

Stock Cultures: Stock cultures of strain A3111 (pHG44 in A4048 cells) were grown overnight at 30° C. in LB medium containing 50 μg/ml ampicillin (Amp). The cultures were diluted two-fold with 50% glycerol and stored at −20° C.

Inoculum: The inoculum was obtained from a single colony of A3111 grown on an LB agar plate containing 100 μg/ml Amp. The LB plates, in turn, were spread with material taken from the stock cultures.

Sterile 3 ml LB medium containing 50 μg/ml Amp was inoculated with a single colony of A3111 and grown for 18 hours at 30° C. in a shaker bath.

Production: Production of bGH was carried out in BHI medium (37 μg/l brain heart infustion (Difco)) containing 50 μg/ml Amp. The inoculum was diluted 1:100 into a flask containing fresh BHI+50 μg/ml Amp, and grown in a shaker bath at 30° C. until the cell concentration reached about $4 \times 10^8$ cells/ml ($OD._{600}=0.5$).

For the induction of bGH production, the flask was transferred to a shaker bath set at 42° C. Cell samples were taken at time 0 and at 90 minutes after the beginning of induction.

Analysis of bGH Production: bGH production was analyzed on a 10-26% gradient acrylamide gel. The cell samples were spun in a microfuge, the supernatant was removed, and the pellets were dissolved in sample buffers (2%, SDS, 50 mM Tris pH 7.0, 3% sucrose, 5% β-Mercaptoethanol) and loaded on the gel. After electrophoresis at 200 volts for 2-1/2 hours, the gels were stained with Coomassie blue and the amount of bGH was determined by scanning with a gel scanner.

After 90 minutes of induction at 42° C., bGH comprises about 20% of the total protein of A3111.

3. Autolysis

Strain A3111 carries pHG44, the defective prophage λcI857 ΔH1 ΔBam H1, and a stable PlcIts plasmid. After prolonged induction at 42° C., the cells will start to lyse due to the production of endolysin directed by P1. Complete lysis of the culture was achieved after 2.5–3 hrs.

Test of Controlled Autolysis: 5 ml of A3111 culture were taken before and after induction at 42° C. (90 min.) and spun down in a Sorvall centrifuge at 7000 rpm for 7 minutes. The supernatants were removed and the pellets were frozen at −20° C. overnight. The pellets were then resuspended in 0.5 ml of T.E. buffer (10 mM Tris pH 8.0, 1 mM EDTA) and 0.1 ml was diluted 1:10 with T.E. and the $OD._{600}$ determined.

As a control for this experiment we used strain A4085 which, similarly to A3111, contains pHG44 and the defective prophage λcI857 ΔH1 ΔBam H1 but does not carry the PlcIts plasmid.

The results of such an experiment appear in Table III which shows that cells containing the PlcIts plasmid (A3111) lyse immediately upon thawing. Inspection of the thawed mixture revealed that over 95% of the cells were lysed following this treatment.

TABLE III

| Strain | PlcIts | $OD._{600}$ Before Freezing | After Thawing | % Loss |
|---|---|---|---|---|
| A4085 | − | 0.980 | 0.851 | 14 |
| A3111 | + | 0.543 | 0.08 | 86 |

The lysis procedure simplifies the extraction of bGH from the induced cells without affecting bGH production.

EXAMPLE 17

Toxicological Evaluation of hCuZnSOD

Toxicology studies of the hSOD prepared in Example 9 were carried out on the Macaca Fasicularis (Cynomolgus) monkey.

0.2 g/kg Study

Two males and two females were dosed with hSOD at 0.2 g/kg. The study was performed by intravenous bolus injection in physiological saline at a concentration of 150 mg/ml. The indices of safety evaluation were weight change, hematology, serum chemistry, urinalysis, daily observation, renal biopsy (pre-dose and 72 hr.), renal immunochemistry (IgM and IgG) and pathological evaluation. No essential test results were reported that could be attributed to test article administration in this study. More specifically, no evidence of pathology in the renal cortex at 72 hr. or at sacrifice (144 hr.) was observed. The serum chemistry induces of renal function remained normal throughout the study. The right or contralateral kidney which was evaluated at necropsy gave no evidence of test article related toxicity either by gross or histopathological examination. Immunochemistry or immunohistopathology for IgM or IgG was unremarkable as well.

0.3 g/kg Study

Two males and two females were dosed with hSOD prepared as described in Example 9. The dose injected in this study was 0.3 g/kg by intravenous bolus injection dissolved in physiological saline.

The parameters measured for both general health effects of hSOD and its nephrotoxicity included daily observations, serum and urine analysis, renal biopsy, renal immunohistopathology and histopathology. No evidence of transitory renal pathology or immunological reaction was observed. However, slight increase in serum BUN levels were observed, which returned to normal by sacrifice at 144 hr., creatinine levels showed mild elevation within normal range. In summary, there was no evidence of immunohistopathology in the kidney (or elsewhere) and no essential test results could at attributed to test article administration in this study.

The results of these two toxicology studies employing recombinant human SOD analog is in marked contrast to bovine-SOD (orgotein) whose $LD_{50}$ in monkeys

EXAMPLE 18

Activity of hCuZnSOD After Repeated Lyophylization

Human CuZnSOD as prepared according to the method described in Example 9 was dissolved 1 mg/ml in H₂O or in 10 mM NH₄HCO₃ and divided to 1 ml samples. Several vials were frozen and kept as a zero reference. The other samples were lyophilized then redissolved in 1 ml of H₂O or in 10 mM NH₄HCO₃ and lyophilized again. At each stage of lyophilization duplicate samples from the H₂O and from the NH₄HCO₃ treated samples were withdrawn and kept at 4° C. At the end of the experiment samples which had either not been lyophilized or lyophilized 1, 2, 3, 4, or 5 times (designated O, I, II, III, IV and V, respectively) were obtained for the H₂O and 10 mM NH₄HCO₃ treated samples. All four sets of lyophilized Cu-Zn-hSOD were assayed for activity in triplicates. Each of the following experiments was performed on a different day.

The experiments demonstrate that the hSOD analog produced in bacteria retains most of its activity even after repeated lyophilizations, unlike natural hSOD which loses most of its enzymatic activity after two lyophilizations. (See U.S. Pat. No. 3,637,640.)

TABLE IV

| $\mu$/mg | | mean | std. dev. | std. error | % activity as compared to fresh hCuZnSOD |
|---|---|---|---|---|---|
| hCuZnSOD Lyophilizations in H₂O | | | | | |
| Exp. 1 | | | | | |
| 0 | 2771 | 3036 | 247 | 142 | 106 |
| 0 | 3079 | | | | |
| 0 | 3259 | | | | |
| I | 2577 | 2832 | 221 | 128 | 99 |
| I | 2960 | | | | |
| I | 2960 | | | | |
| II | 2381 | 2465 | 145 | 84 | 86 |
| II | 2381 | | | | |
| II | 2632 | | | | |
| III | 2482 | 2569 | 151 | 87 | 90 |
| III | 2482 | | | | |
| III | 2743 | | | | |
| IV | 2353 | 2436 | 143 | 83 | 85 |
| IV | 2601 | | | | |
| IV | 2353 | | | | |
| V | 2393 | 2477 | 146 | 84 | 87 |
| V | 2393 | | | | |
| V | 2646 | | | | |
| fresh | 2570 | 2855 | 293 | 169 | 100 |
| fresh | 2840 | | | | |
| fresh | 3156 | | | | |
| Exp. 2 | | | | | |
| 0 | 3103 | 3368 | 252 | 145 | 95 |
| 0 | 3398 | | | | |
| 0 | 3604 | | | | |
| I | 3045 | 3229 | 186 | 108 | 91 |
| I | 3225 | | | | |
| I | 3418 | | | | |
| II | 3295 | 3197 | 143 | 82 | 91 |
| II | 3263 | | | | |
| II | 3033 | | | | |
| III | 3125 | 3238 | 99 | 57 | 92 |
| III | 3308 | | | | |
| III | 3281 | | | | |
| IV | 3111 | 3085 | 25 | 14 | 87 |
| IV | 3081 | | | | |
| IV | 3062 | | | | |
| V | 3050 | 2869 | 272 | 157 | 81 |
| V | 2556 | | | | |
| V | 3002 | | | | |
| fresh | 4017 | 3529 | 423 | 244 | 100 |
| fresh | 3281 | | | | |
| fresh | 3289 | | | | |
| hCuZnSOD Lyophilizations in 10 mM NH₄HCO₃ | | | | | |
| Exp. 3 | | | | | |
| 0 | 2938 | 3139 | 199 | 115 | 101 |
| 0 | 3141 | | | | |
| 0 | 3337 | | | | |
| I | 2764 | 3002 | 206 | 119 | 96 |
| I | 3130 | | | | |
| I | 3111 | | | | |
| II | 2782 | 3092 | 286 | 165 | 99 |
| II | 3345 | | | | |
| II | 3148 | | | | |
| III | 2697 | 2922 | 195 | 113 | 94 |
| III | 3035 | | | | |
| III | 3035 | | | | |
| IV | 2680 | 2908 | 282 | 163 | 93 |
| IV | 3224 | | | | |
| IV | 2820 | | | | |
| V | 2558 | 2680 | 211 | 122 | 86 |
| V | 2558 | | | | |
| V | 2923 | | | | |
| fresh | 2803 | 3110 | 287 | 166 | 100 |
| fresh | 3372 | | | | |
| fresh | 3155 | | | | |
| Exp. 4 | | | | | |
| 0 | 4495 | 4692 | 170 | 98 | 120 |
| 0 | 4790 | | | | |
| 0 | 4790 | | | | |
| I | 3842 | 3842 | 0 | 0 | 99 |
| I | 3842 | | | | |
| I | 3842 | | | | |
| II | 3965 | 3506 | 397 | 229 | 90 |
| II | 3277 | | | | |
| II | 3277 | | | | |
| III | 3210 | 3485 | 195 | 113 | 90 |
| III | 3372 | | | | |
| III | 3372 | | | | |
| IV | 3785 | 3671 | 199 | 115 | 94 |
| IV | 3442 | | | | |
| IV | 3787 | | | | |
| V | 3349 | 3419 | 121 | 70 | 88 |
| V | 3558 | | | | |
| V | 3349 | | | | |
| fresh | 3885 | 3885 | 0 | 0 | 100 |
| fresh | 3885 | | | | |
| fresh | 3885 | | | | |

EXAMPLE 19

Exclusive Expression of Non-Acetylated hCuZnSOD in E. Coli

Figure 25:
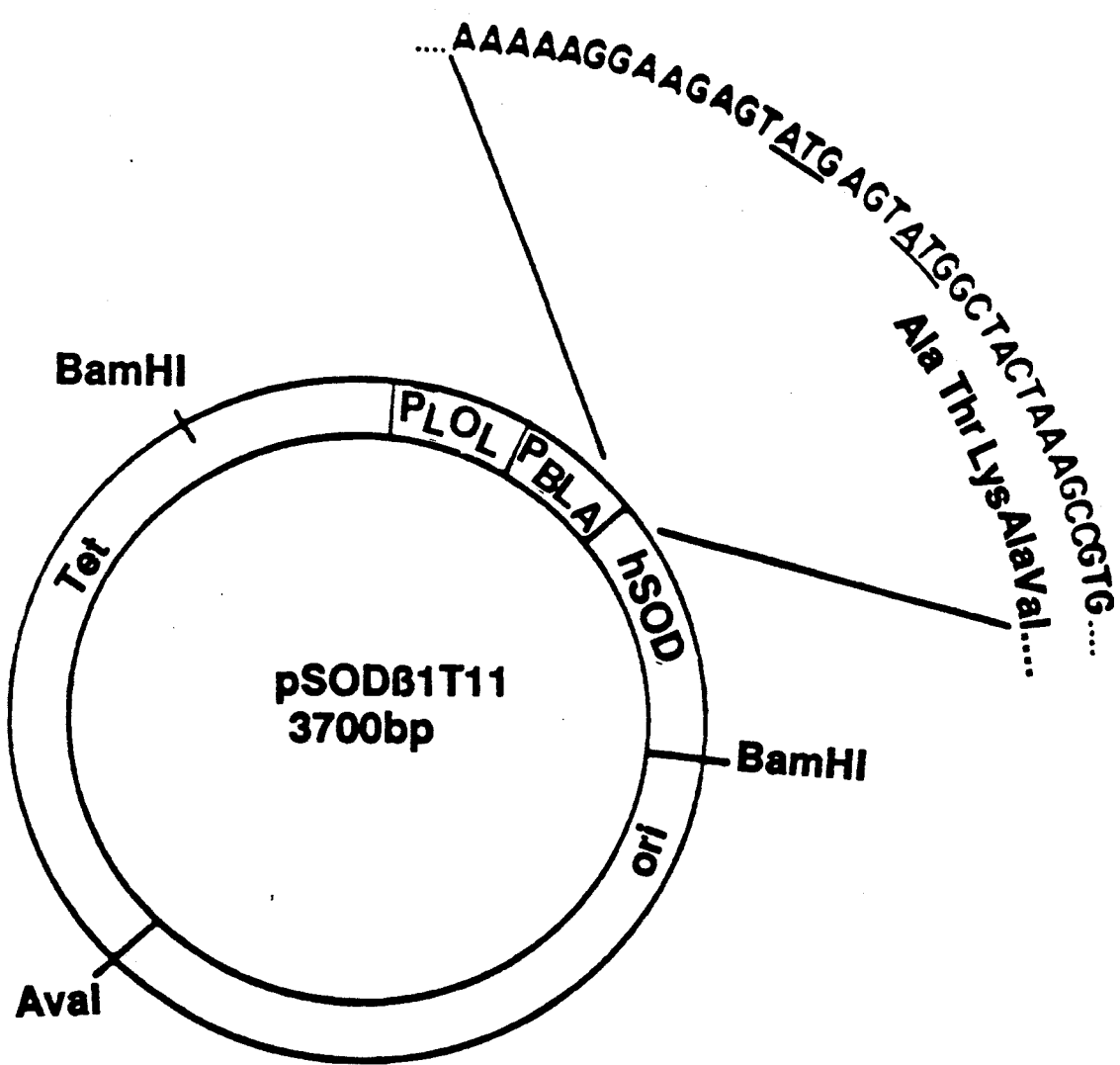

According to the DNA sequence of the cloned human CuZn SOD in pSOD$\beta_1$T$_{11}$, initiation of protein synthesis could start at either one of two ATG codons located at the 5' end of the gene (FIG. 25). Protein sequencing studies prove that hSOD isolated from E. coli lacks an N-terminal methionine and most of it begins with an alanine residue. This result suggests that protein biosynthesis is initiated at the second ATG and that the methionyl residue is removed by a bacterial peptidase. However, about 5% of the expressed enzyme contain Ser−Met−Ala at the amino terminus indicating that the first ATG can also be utilized to initiate translation. The following steps were undertaken in order to eliminate the first ATG, thus leading to the exclusive expression of non-acetylated hCuZnSOD analog having an amino acid sequence identical to that of natural human CuZn SOD.

Construction of pΔRB

Tet$^R$ expression vector, pΔRB, was generated from pSOD$\beta_1$T$_{11}$ by complete digestion with EcoRI folis reported to be 10 mg/kg (Grunenthal-Sales brochure describing Peroxinorm ® superoxide dismutase).

lowed by partial cleavage with BamHI restriction enzymes. The digested plasmid was ligated with synthetic oligomer.

```
5'-AATTCCCGGGTCTAGATCT-3'
3'-     GGGCCCAGATCTAGACTAG-5'
``` resulting in pΔRB containing the λ $P_L$ promoter. (FIG. 26).

Construction of pβUN

Construction of pβUN, a general purpose expression vector, containing the λ$P_L$. promoter and β-lactamase promoter and RBS is shown in FIG. 27. Unique NdeI site followed by SmaI, SbaI and BglII sites were introduced downstream of the β-lactamase RBS for insertion of any desired gene. It should be pointed out that 3 nucleotide changes were made at the 3' end of the lactamase RBS - , one to eliminate the first possible ATG (C instead of G) and two other changes to form the NdeI site (CA instead of AG).

Construction of pSODβMA

The entire coding region of human CuZn SOD on a NdeI-BamHI fragment isolated from pSODα13, was inserted between the unique NdeI and BglII sites of pβUN as depicted in FIG. 28. The resulting vector, pSODβMA, failed to express high levels of hSOD upon induction.

Construction of pSODβMAX

High level expression of authentic hSOD was achieved by a single base change in the β-lactamase RBS region as compared to the sequence present in pSODβ$_1$T$_{11}$1 (FIG. 25). The 22 bp long SspI-NdeI fragment of pSODβMA was replaced with 3 different synthetic fragments, each having a single base substitution which eliminates the first ATG (either C, T or A instead of G in the third position of the initiator codon). The construction of the pSODβMAX$_{12}$ and pSODβ-MAX$_{10}$ clones are described in FIGS. 29 and 30, respectively. pSODβMAX$_{12}$ in prototrophic E. coli host A4255 has been deposited with the American Type Culture Collection and ssigned ATCC Accession No. 67177. As shown in Table V only the G to C and G to A substitutions resulted in high level hSOD expression upon induction.

TABLE V

| SOD EXPRESSION VECTORS | SEQUENCE AT THE 5' END | % SOD BY GEL SCAN |
|---|---|---|
| β$_1$T$_{11}$ | AGGAAGAGT<u>ATG</u>AGT<u>ATG</u>GCT | 6.5 |
| βMA | AGGAAGAGTA<u>CC</u>AT<u>ATG</u>GCT | 0.1 |
| βMAX$_{10}$ | AGGAAGAGTA<u>C</u>AGT<u>ATG</u>GCT | 6.8 |
| βMAX$_{11}$ | AGGAAGAGTA<u>TT</u>AGT<u>ATG</u>GCT | 0.1 |
| βMAX$_{12}$ | AGGAAGAGTA<u>A</u>AGT<u>ATG</u>GCT | 8.3 |

What is claimed is:

1. A plasmid for the production of an enzymatically active polypeptide analog of human Cu-Zn superoxide dismutase having an amino acid sequence substantially identical to the amino acid sequence of, and the biological activity of naturally-occurring human Cu-Zn superoxide dismutase but an N-terminus which is not acetylated, which upon introduction into a suitable Escherichia coli host cell containing the thermolabile repressor $C_I$ renders the host cell capable, upon increasing the temperature of the host cell to a temperature at which the repressor is inactivated, of effecting expression of DNA encoding the human Cu-Zn superoxide dismutase polypeptide analog comprising:
   a double-stranded DNA molecule which includes in 5' to 3' order the following:
   a DNA sequence which contains the promoter and operator $P_LO_L$ from λ bacteriophage;
   an N utilization site selected from the group consisting of Nut$_L$ and Nut$_R$ for binding antiterminator N protein produced by the Escherichia coli host cell;
   a DNA sequence which contains the naturally-occurring β-lactamase ribosomal binding site present in pBR322;
   an ATG initiation codon;
   DNA encoding the human Cu-Zn superoxide dismutase polypeptide analog in phase with ATG initiation codon;
   and which additionally includes a DNA sequence which contains an origin of replication from the bacterial plasmid pBR322 capable of autonomous replication in the Escherichia coli host cell and a DNA sequence which contains a gene associated with a selectable or identifiable phenotypic trait which is manifested when the plasmid is present in the Escherichia coli host cell.

2. A host plasmid system comprising the plasmid of claim 1 in an Escherichia coli host cell capable of expressing the DNA encoding the human Cu-Zn superoxide dismutase present in the plasmid.

3. A method of producing an enzymatically active non-acetylated polypeptide analog of human Cu-Zn superoxide dismutase having an amino acid sequence substantially identical to the amino acid sequence of, and the biological activity of, naturally-occurring human Cu-Zn superoxide dismutase, which comprises growing the host plasmid system of claim 2 under conditions permitting production of the active superoxide dismutase analog and recovering the active analog so produced.

4. A host plasmid system according to claim 2, wherein the host is a prototroph.

5. A host plasmid system according to claim 4, wherein the host is Escherichia coli strain A4200, the host being deposited under ATCC Accession No. 53218.

6. A host plasmid system according to claim 4, wherein the host is Escherichia coli strain A4255, the host being deposited under ATCC Accession No. 53468.

7. A host plasmid system according to claim 2, wherein the host is a lytic strain.

8. A host plasmid system according to claim 7, wherein the host is Escherichia coli strain A4048, the host being deposited under ATCC Accession No. 53217.

9. The plasmid designated pSODβ$_1$T$_{11}$ having the restriction map shown in FIG. 15 and deposited under ATCC Accession No. 53468.

10. The plasmid designated pSOD-βMAX$_{12}$ having the restriction map shown in FIG. 29 and deposited under ATCC Accession No. 67177.

11. A host plasmid system comprising the plasmid of claim 10 in an *Escherichia coli* capable of expressing the DNA encoding the human Cu-Zn superoxide dismutase present in the plasmid.

12. The host plasmid system of claim 11, wherein the host is *Escherichia coli* A1645, the host being deposited under ATCC Accession No. 39783.

13. The host plasmid system of claim 11, wherein the host is *Escherichia coli* A4255, the host being deposited under ATCC Accession No. 67177.

14. A method of producing an enzymatically active non-acetylated polypeptide analog of human Cu-Zn superoxide dismutase having an amino acid sequence substantially identical to the amino acid sequence of, and the biological activity of, naturally-occurring human Cu-Zn superoxide dismutase, which comprises growing the host plasmid system of claim 11 under conditions permitting production of the active superoxide dismutase analog and recovering the active analog so produced.

15. The plasmid designed pSOD-βMAX$_{10}$ having the restriction map shown in FIG. 30.

16. A host plasmid system comprising the plasmid of claim 15 and an *Escherichia coli* host cell capable of expressing the DNA encoding the human Cu-Zn superoxide dismutase present in the plasmid.

17. The host plasmid system of claim 16, wherein the host is *Escherichia coli* A1645, the host being deposited under ATCC Accession No. 39783.

18. The host plasmid system of claim 16, wherein the host is *Escherichia coli* A4255, the host being deposited under ATCC Accession No. 53468.

19. A method of producing an enzymatically active non-acetylated polypeptide analog of human Cu-Zn superoxide dismutase having an amino acid sequence substantially identical to the amino acid sequence of, and the biological activity of, naturally-occurring human Cu-Zn superoxide dismutase which comprises growing the host plasmid system of claim 16 under suitable conditions permitting production of the superoxide dismutase analog and recovering the analog so produced.

20. A plasmid of claim 1, wherein the distance between the 3' end of the $P_LO_L$ promoter and operator sequence and the 5' end of the N utilization site is less than about 80 base pairs and the distance between the 3' end of the N utilization site and the 5' end of the ribosomal binding site is less than about 300 base pairs.

* * * * *